US009994464B2

(12) United States Patent
Dietz

(10) Patent No.: US 9,994,464 B2
(45) Date of Patent: Jun. 12, 2018

(54) METHOD AND DEVICES FOR DE-EMULSIFYING AND COMPLEXING ORGANIC COMPOUNDS IN EMULSIONS

(71) Applicant: Drei Lilien PVG GmbH & Co. KG, Wiesbaden (DE)

(72) Inventor: Max Dietz, Wiesbaden (DE)

(73) Assignee: Drei Lilien PVG GmbH & Co. KG, Wiesbaden (DE)

( * ) Notice: Subject to any disclaimer, the term of this patent is extended or adjusted under 35 U.S.C. 154(b) by 0 days. days.

(21) Appl. No.: 15/315,481

(22) PCT Filed: Jun. 1, 2015

(86) PCT No.: PCT/EP2015/062181
§ 371 (c)(1),
(2) Date: Dec. 1, 2016

(87) PCT Pub. No.: WO2015/185516
PCT Pub. Date: Dec. 10, 2015

(65) Prior Publication Data
US 2017/0260072 A1    Sep. 14, 2017

(30) Foreign Application Priority Data
Jun. 3, 2014    (DE) .................. 10 2014 007 859

(51) Int. Cl.
| C02F 1/52 | (2006.01) |
| B01D 17/04 | (2006.01) |
| B01D 17/02 | (2006.01) |
| C02F 1/68 | (2006.01) |
| C02F 1/38 | (2006.01) |
| C02F 1/00 | (2006.01) |
| C11B 3/00 | (2006.01) |
| C11B 3/02 | (2006.01) |
| C11B 3/16 | (2006.01) |
| C11B 1/10 | (2006.01) |
| C07F 9/117 | (2006.01) |
| C07F 9/10 | (2006.01) |
| C02F 101/30 | (2006.01) |
| C02F 103/22 | (2006.01) |
| C02F 103/26 | (2006.01) |
| C02F 103/32 | (2006.01) |

(52) U.S. Cl.
CPC ........ *C02F 1/5236* (2013.01); *B01D 17/0208* (2013.01); *B01D 17/0217* (2013.01); *B01D 17/047* (2013.01); *B01D 17/048* (2013.01); *C02F 1/001* (2013.01); *C02F 1/385* (2013.01); *C02F 1/681* (2013.01); *C07F 9/103* (2013.01); *C07F 9/117* (2013.01); *C11B 1/108* (2013.01); *C11B 3/006* (2013.01); *C11B 3/008* (2013.01); *C11B 3/02* (2013.01); *C11B 3/16* (2013.01); *C02F 2001/007* (2013.01); *C02F 2101/30* (2013.01); *C02F 2103/22* (2013.01); *C02F 2103/26* (2013.01); *C02F 2103/32* (2013.01)

(58) Field of Classification Search
CPC .......... C02F 1/40; C02F 1/681; C02F 1/5236; B01D 17/04; B01D 17/047; B01D 17/048; C11B 1/108; C11B 3/06; C11B 3/02
See application file for complete search history.

(56) References Cited

U.S. PATENT DOCUMENTS

| 1,911,839 | A | * | 5/1933 | Meinzer ............. B01D 17/0205 516/138 |
| 2,275,661 | A | * | 3/1942 | Steinle .................... C11B 11/00 209/10 |
| 4,436,643 | A | | 3/1984 | Burger et al. |
| 5,433,863 | A | | 7/1995 | Braden et al. |
| 5,973,005 | A | * | 10/1999 | D'Amelio, Sr. ....... C07C 277/08 514/565 |
| 7,750,119 | B2 | * | 7/2010 | Segall ....................... A23J 1/14 530/370 |
| 2013/0090488 | A1 | | 4/2013 | Dietz |
| 2015/0148555 | A1 | | 5/2015 | Hruschka et al. |

FOREIGN PATENT DOCUMENTS

WO    WO 2011/160857    * 12/2011    ............. C07B 63/04

OTHER PUBLICATIONS

Zadernowski,R., et al., Composition of Total Lipids in Rapeseed, 1978, Journal of the American Oil Chemists' Society, vol. 55, pp. 870-872 (Year: 1978).*
Irlyama, K., et al., A somple method for extraction and partial purificaiton of chlorophyll form plant material, using dioxane, 1974, J. Biochem, vol. 76, No. 4, pp. 901-904 (Year: 1974).*
Niciforovic, N., et al., Sinapic acid and its derivatives: Natural Sources and Bioactivity, 2103, Comprehensive Reviews in Food Science and Food Safety, vol. 13, issue 1, pp. 34-51 (Year: 2013).*
Toyama, N., et al., Solvation structure of arginine in aqueous solution studied by liquid beam technique, 2006, Chemical Physics Letters, vol. 419, pp. 369-373 (Year: 2006).*

(Continued)

*Primary Examiner* — Yate' K Cutliff
(74) *Attorney, Agent, or Firm* — Amin, Turocy & Watson LLP

(57) ABSTRACT

The invention relates to a method for aggregating and separating an organic material mixture which is provided in a dissolved form in an aqueous emulsion. The method is characterized by the following steps: a) providing an aqueous emulsion with organic compounds which are provided in the emulsion in a dissolved form, said organic compounds being carboxylic acids, phospholipids, glycolipids, glyceroglycolipids, phenols, sterols, chlorophyll, and/or sinapines, b) mixing the emulsion from step a) with an aqueous solution containing copper(II) ions and/or calcium ions until an aggregate formation is achieved, and c) separating the aggregates from step b) by means of a sedimentation, filtration, or centrifugation process after achieving an aggregated phase of the organic compounds from step b).

22 Claims, No Drawings

(56) References Cited

OTHER PUBLICATIONS

International Search Report for International Patent Application No. PCT/EP2015/062181 dated Sep. 25, 2015, 7 pages.
Written Opinion for International Patent Application No. PCT/EP2015/062181 dated Sep. 25, 2015, 6 pages.
International Preliminary Examination Report for International Patent Application No. PCT/EP2015/062181 dated Sep. 25, 2015, 7 pages.

\* cited by examiner

METHOD AND DEVICES FOR DE-EMULSIFYING AND COMPLEXING ORGANIC COMPOUNDS IN EMULSIONS

The present invention relates to the provision of a process for separating an organic material mixture from an aqueous emulsion.

BACKGROUND OF THE INVENTION

Emulsions are water- or oil-based solutions, in which the compounds are present in dissolved form, that are characterized as amphiphilic due to their structural properties, thus, enabling hydrophilic and hydrophobic interactions. Therefore, the emulsifying effect of such compounds in a liquid system is enhanced by providing optimal interaction between both the water molecules and the organic compounds. Methods and procedures are known from the prior art with which it is possible to prepare emulsions by mixing a water phase and an oil phase. Such emulsions will separate into an oil and water phase spontaneously if amphiphilic compounds are not present. Organic compounds that provide stabilization of water-oil mixtures in the form of an emulsion, in which they are present either as water droplets in oil or oil droplets in water, are called emulsifiers. Emulsions which are stabilized by emulsifiers are suitable for receiving further organic compounds, wherein they align at the phase boundaries according to thermodynamic principles. Therefore, emulsions are very well suited to split non-covalent bindings between organic and inorganic compounds and transfer organic compounds into the liquid emulsion phase. An emulsifier-stabilized emulsion leads to an improvement of the solution properties. In order to achieve a further improvement of dissolution characteristics, the phase boundary must be increased. Insofar solvation systems have been developed that are based on the formation of micro- and nano-emulsions, which exhibit an increased capacity to dissolve organic compounds due to a reduction of the surface tension of such emulsions. Because of the improved solubility of organic compounds that are stabilized by a solvation layer, those organic compounds do not or only to a very small extent aggregate or interact with other compounds that are dissolved. In such a way, dissolved organic compounds remain in a dissolved state for an indefinite duration, even in a predominantly water- or oil-based medium, in which they would not be soluble or dissolve poorly otherwise. The greater solvation potency of such amphiphilic emulsifiers, on the other hand, makes it more difficult to remove the dissolved organic compounds.

WO 2011/160857 A2 discloses methods and procedures to produce nano-emulsions which are suitable to dissolve a variety of organic compounds. In one aspect nano-emulsions are obtained by aqueous solutions of hydrophilic compounds with guanidino and/or amidino groups, which have a $K_{ow}$<6.3. $K_{ow}$ is referred to the partition coefficient and represents the relation of distribution of a substance between n-octanol and water. It is stated that carboxylic acids electrostatically adhere to guanidino or amidino groups up to an equimolar ratio and that thereby the hydrophobic carboxylic acids obtain a hydration shell, which makes them soluble in an aqueous medium. The electrostatic interaction can be terminated again by protonation of the carboxylic groups of the carboxylic acid. It was found that it is possible to use a solution of dissolved compounds carrying guanidino and/or amidino groups for separation of carboxylic acids from a lipophilic medium with a high separation efficiency.

The dimer that is produced by the interaction of the hydrophilic compounds carrying guanidino and/or amidino groups with carboxylic acids creates a hydration shell, which allows solubilization of this dimer in an aqueous medium and formation of nano-emulsions. In addition, compounds carrying guanidino and/or amidino groups cause detachment of other organic and inorganic compounds that interact with the carboxylic acid. Furthermore, the hydration shell of compounds carrying guanidino and/or amidino groups, on the one hand, and hydrophobic groups of the carboxylic acids, on the other hand, enable electrostatic interactions with complexed organic compounds, whereby they are partially hydrated. A high penetration efficacy of nano-emulsions into densely packed and also anhydrous mixtures of organic matter has already been described in the scientific literature. Nano-emulsions can also be used to separate compounds from the organic complexes in order to retrieve them.

It was shown that solutions of compounds carrying guanidino and/or amidino groups can be used to refine lipid phases. By doing so, concentrations of free carboxylic acids in the lipid phase can by lowered to the minimum values that are required to comply with industrial standards.

Furthermore, other organic compounds that are present in the lipid phases are solubilized and transferred into the aqueous phase forming an aqueous emulsion that can be separated by phase separation.

Those organic compounds can be, in particular, phospholipids, glycolipids but also colouring and flavouring agents. Furthermore, inorganic compounds, such as sodium, potassium, calcium, magnesium, copper, iron, and other compounds are simultaneously removed with the water phase. In addition, advantageous applications were also documented for purification methods and decomplexing methods. This is especially true for materials (e.g., press cake of plants, sewage sludge, fruit skins, or shells) having a relevant content of organic and/or lipophilic compounds, in which it is possible to achieve a high separation efficiency of those organic compounds that are complexed with lipids or inorganic compounds, by the use of solutions of compounds carrying guanidino and/or amidino groups or nano-emulsions consisting of solutions of compounds carrying guanidino and/or amidino groups and carboxylic acids. The enormous emulsion performance of nano-emulsions, consisting of dissolved compounds carrying guanidino and/or amidino groups and carboxylic acids, also leads to an extremely stable solubilization of lipophilic, hydrophilic, and amphiphilic compounds, so that separation of the solubilized organic compounds from such aqueous solutions/emulsions by means of centrifugation (e.g., by ultracentrifugation) is virtually impossible and can only be achieved under drastic conditions, such as a pH shift in a strongly acidic range (e.g., pH<3 [acidic work up]). Such emulsions, which have been cleared from any filterable solids, showed no visible changes over months, in particular, settling of solid components did not occur, provided that larger aggregates have previously been separated. Therefore, the special stability of an emulsion having a mixture of organic compounds prepared in such a manner becomes apparent. Thermal treatment of those emulsions had no effect; extraction tests with solvents, such as hexane, diethyl ether, dimethylformamide or chloroform, showed only a low separation performance for the dissolved organic compounds or the solvents remain partially or completely in the aqueous phase. Adsorptive techniques, such as chromatography, had virtually no separation effects.

A strong protonation of nano-emulsions, consisting of dissolved compounds carrying guanidino and/or amidino groups and carboxylic acids, liberates the carboxylic acids which can then be separated from the aqueous solution by phase separation. For the re-use of solutions containing compounds carrying guanidino and/or amidino groups for the solubilization and separation of carboxylic acids in a lipid phase, however, a pH>7.0 is required in order to achieve a sufficient dissolution capacity for carboxylic acids. Therefore, an acidic workup of said nano-emulsion would necessitate subsequent adjustment of the pH of the solution containing compounds carrying guanidino and/or amidino-groups by means of a base for a further recycling method, and thus the recycling method of the solution containing the compound carrying a guanidino or amidino group would be uneconomical. In addition, chemical reactions of dissolved organic compounds can occur under acidic conditions, leading to unwanted changes. Thus, the organic compounds that are obtained after an acidic workup can usually not be commercially used.

Another known method is based on displacement extraction of the carboxylic acids with an alcohol. It has been shown that lowering of the pH is also necessary here in order to allow a sufficient separation of nano-emulsified fatty acids. The additional presence of an alcohol in an acidic reaction mixture leads to chemical changes of many organic compounds. It was shown that such a method is not appropriate, if the solution containing guanidino- or amidino group carrying compounds should be reused for a renewed separation of carboxylic acids from a lipid phase compounds carrying, since the presence of an alcohol which has remained in the aqueous phase reduces the efficacy of those compounds to separate carboxylic acids. Thus, no methods or techniques are available or are known from the prior art with which the carboxylic acids and/or other organic compounds in nano-emulsions, consisting of compounds carrying guanidino- and/or amidino groups carrying compounds and dissolved carboxylic acids, can be separated under mild conditions as well as with simple and economic measures in order to retrieve the organic compounds and to purify the aqueous solution, so that it is applicable for reuse. In order to meet these requirement, an appropriate method and process technology and apparatus is mandatory, in particular for the processing of nano-emulsions, consisting of compounds carrying guanidino and/or amidino groups and carboxylic acids. Furthermore, it would be particularly advantageous to receive chemically and structurally unaltered organic compounds with high economic value.

OBJECT OF THE INVENTION

The object of the present invention is the provision of a method for gentle product treatment and inexpensive separation of a mixture of organic substances that is dissolved form in an aqueous emulsion.

This aim is achieved by the technical teaching of the independent claims. Further advantageous embodiments of the invention result from the dependent claims, the description, the figures and the examples.

DETAILED DESCRIPTION OF THE INVENTION

According to the invention, the object is achieved by means of water-soluble ionic copper and calcium compounds, which lead to an aggregation of carboxylic acids, as well as other organic compounds that are not compounds carrying guanidino and/or amidino groups, which are present in an aqueous solution containing compounds carrying guanidino and/or amidino groups. Thereafter, the aggregates can be separated from the aqueous solution that still comprises compounds carrying guanidino and/or amidino groups.

According to the invention the task is solved by a process for the aggregation and separation of a mixture of organic substances, which are dissolved in an aqueous emulsion, characterized by the steps of:
a) provision of an aqueous emulsion having organic compounds dissolved therein, wherein the organic compounds are carboxylic acids, phospholipids, glycolipids, glyceroglycolipids, phenols, sterols, chlorophylls, sinapines, peptides, proteins, carbohydrates, lipoproteins, waxes and/or fatty alcohols,
b) mixing the emulsion of step a) with an aqueous solution containing copper(II) ions and/or calcium ions until aggregate formation,
c) separating the aggregates from step b) by sedimentation, filtration, or centrifugation after obtaining an aggregated phase of organic compounds from step b).

In the course of investigations of aqueous emulsions and nano-emulsions obtained through a refining process or a cleaning- or decomplexation procedures with solutions or nano-emulsions consisting of dissolved compounds carrying guanidino and/or amidino groups, it turned out that in addition to carboxylic acids, phospholipids, glycolipids, glyceroglycolipids, phenols, sterols, squalene, plant dyes, such as chlorophylls and carotenes, sinapines, peptides, proteins, carbohydrates, lipoproteins, waxes and/or fatty alcohols are also separated. Thereby, the carboxylic acids, phospholipids, glycolipids, glyceroglycolipids, phenols, sterols, squalene, plant dyes, such as chlorophylls and carotenes, sinapines, peptides, proteins, carbohydrates, lipoproteins, flavoring agents, waxes and/or fatty alcohols may be present individually or as a mixture in the aqueous emulsions.

So it can be for example a mixture of peptides, sterols, and carbohydrates or a mixture of glycolipids and phospholipids. The aqueous solutions that have been used for refinement may contain also phospholipids, glycolipids, glyceroglycolipids, phenols, sterols, squalene, flavorings, vegetable dyes, such as chlorophylls and carotenoids, and/or sinapines apart from carboxylic acids, these substances are dissolved in the aqueous medium. This emulsion is hereinafter also referred as aqueous extraction mixture or aqueous emulsion. The aqueous extraction mixture can be an aqueous extraction solution or an aqueous extraction suspension.

Preferred is an emulsion containing carboxylic acids, phospholipids, glycolipids, glyceroglycolipids, phenols, sterols, chlorophylls, sinapines, peptides, proteins, carbohydrates, lipoproteins, waxes and/or fatty alcohols in each case individually or as a mixture.

The invention also relates to methods for the aggregation and separation of a mixture of organic substances, which are dissolved in an aqueous emulsion, characterized by the steps of:
a) provision of an aqueous emulsion having organic compounds dissolved therein, wherein the organic compounds are carboxylic acids, phospholipids, glycolipids, glyceroglycolipids, phenols, sterols, chlorophylls and/or sinapines,
b) mixing the emulsion of step a) with an aqueous solution containing copper(II) ions and/or calcium ions until aggregate formation, c) separating the aggregates from step b) by sedimentation, filtration, or centrifugation after obtaining an aggregated phase of organic compounds from step b).

The invention further relates to methods of aggregation and separation of a mixture of organic substances, which are dissolved in an aqueous emulsion, characterized by the steps of:
a) provision of an aqueous emulsion having organic compounds dissolved therein, wherein the organic compounds are carboxylic acids, phospholipids, glycolipids, glyceroglycolipids, phenols, sterols, chlorophylls and/or sinapines,
b) mixing the emulsion of step a) with calcium oxide, magnesium oxide, and/or zinc oxide, or with an aqueous solution containing copper(II) ions and/or calcium ions until aggregate formation,
c) separating the aggregates from step b) by sedimentation, filtration, or centrifugation after obtaining an aggregated phase of organic compounds from step b).

The calcium oxide, magnesium oxide, and/or zinc oxide is preferably added as a solid in powder form to the aqueous emulsion or is added as an aqueous dispersion to the aqueous emulsion or is added in suspended form to the aqueous emulsion.

The invention further relates to methods of aggregation and separation of a mixture of organic substances, which are dissolved in an aqueous emulsion, characterized by the steps of:
a) providing an aqueous emulsion having organic compounds dissolved therein, wherein the organic compounds are carboxylic acids, phospholipids, glycolipids, glyceroglycolipids, phenols, sterols, chlorophylls and/or sinapine,
b) mixing the emulsion of step a) with calcium oxide, magnesium oxide and/or zinc oxide until aggregate formation,
c) separating the aggregates from step b) by sedimentation, filtration, or centrifugation after obtaining an aggregated phase of organic compounds from step b).

The invention also relates to a process for the aggregation and separation of a mixture of organic substances, which are dissolved in an aqueous emulsion, characterized by the steps of:
a) providing an aqueous emulsion having organic compounds dissolved therein, wherein it the organic compounds are carboxylic acids, phospholipids, glycolipids, glyceroglycolipids, phenols, sterols, chlorophylls and/or sinapines,
b) mixing the emulsion of step a) with an aqueous solution containing copper(II) ions and/or calcium ions and/or with an aqueous dispersion containing calcium oxide, magnesium oxide and/or zinc oxide and/or adding calcium oxide, magnesium oxide and/or zinc oxide in solid form to the emulsion of step a) with mixing until aggregate formation
c) separating the aggregates from step b) by sedimentation, filtration or centrifugation after obtaining an aggregated phase of organic compounds from step b).

Thus, an aqueous solution containing copper(II) ions or an aqueous solutions containing calcium ions or an aqueous solutions containing copper(II) ions and calcium ions, or calcium oxide in solid form or in powder form, or magnesium oxide in solid form or in powder form, or zinc oxide in solid form or in powder form, or calcium oxide and magnesium oxide in solid form or in powder form, or magnesium oxide and zinc oxide in solid form or in powder form, or calcium oxide and zinc oxide in solid form or in powder form, or calcium oxide and magnesium oxide and zinc oxide in solid form or in powder form, or aqueous dispersions containing calcium oxide, or aqueous dispersions containing magnesium oxide, or aqueous dispersions containing zinc oxide, or aqueous dispersions containing calcium oxide and magnesium oxide, or aqueous dispersions containing calcium oxide and zinc oxide, or aqueous dispersions form or containing magnesium oxide and zinc oxide, or an aqueous dispersion containing calcium oxide and magnesium oxide and zinc oxide, or a combination of two or three of the aforementioned solutions, dispersions, or solids can thus be added to the emulsion of step a) as disclosed in the methods described herein (including the 14 methods described below). Preferably, the addition is carried out by mixing and/or preferably at a maximum temperature of 75° C. and/or preferably with a laminar agitator.

Aqueous extraction mixtures contain, besides the above-mentioned carboxylic acids, phospholipids, glycolipids, glyceroglycolipids, phenols, sterols, squalenes, and vegetable dyes, such as chlorophylls and carotenes, typically also relevant quantities of detached inorganic compounds such as sodium, potassium, magnesium, calcium, copper, iron and inorganic compounds encountered in plant extracts which are also liberated.

Surprisingly, it was found that despite the fact that copper ions were present in the aqueous emulsions containing dissolved compounds carrying guanidino and/or amidino groups and other organic compounds, the addition of solutions containing copper ions initiated a rapid and finally complete aggregation of the dissolved organic compounds; however, the dissolved compounds carrying guanidino and/or amidino groups did not aggregate and remained in the aqueous solutions.

The aggregation was already initiated by addition of very small amounts of dissolved ionic copper compounds and led to a very rapid formation of aggregates without further addition of copper ions: this process continued until complete separation of organic compounds was accomplished by spontaneous sedimentation of aggregates. The achievement of aggregate formation in step b) therefore signifies the beginning of the aggregation, which can be recognized with the eye.

The invention therefore relates to a method to aggregate dissolved organic compounds in an aqueous emulsion or nano-emulsion.

The invention pertains in particular a method to aggregate dissolved organic compounds in a neutral or basic aqueous emulsion or nano-emulsion.

In stage b) of the process according to the invention, the addition of an aqueous solution containing copper(II) ions and/or calcium (II) ions can be carried out while mixing the emulsion.

Alternatively, in step b) of the process according to the invention, the mixing can be performed after the addition of an aqueous solution containing copper(II) ions and/or calcium ions to the emulsion. If no aggregation takes place, the process is repeated until the desired aggregate formation begins.

Remarkably, the concentration of copper ions that was present in the resulting clarified aqueous phases with dissolved compounds carrying guanidino and/or amidino groups, after separation of the aggregated organic compounds, corresponded to the amount of bivalent cations that were already present in organic emulsions before initiating aggregation. Aggregation runs independently and without the need for a pH shift. The pH of the cleared process water is almost identical to that of the initial aqueous solutions with dissolved compounds carrying guanidino and/or amidino groups, i.e. before their use to refine a lipid phase. The cleared process water corresponds to the solution with compounds carrying guanidino and/or amidino groups after separating the carboxylic acid and other organic compounds.

Furthermore, it was found that the previously nano-emulsified carboxylic acids were separated along with the other organic compounds present in an aqueous emulsions consisting of compounds carrying guanidino and/or amidino groups. This is particularly advantageous since the obtained aqueous solution with compounds carrying guanidino and/or amidino groups is available now directly for re-use as an extraction medium, e.g., for refinement of a lipid phase.

It could be shown that if an optimal dosage of the copper is carried out by using the minimal amount of copper ions that is required for the inventive aggregation initiation, the obtainable clarified solution contains practically almost no other organic compounds besides the still dissolved compounds carrying guanidino and/or amidino groups and the concentration of copper ions therein does not interfere with or deteriorate the extraction efficiency of the extraction solution when used in a renewed application, e.g., for extraction of organic compounds from lipid phases. Thus, this is a very simple process by which in one step nano-emulsified carboxylic acids can be removed to a required minimum together with the dissolved organic compounds and the cleared or clarified aqueous solution with dissolved compounds carrying guanidino and/or amidino groups that is ready for immediate reuse is obtained. This allows a complete separation of dissolved organic compounds from the process water. Here, the concentration of dissolved organic compounds in the clarified process water is less than 1.0 mmol/l, with the exception of the concentrations of the compounds carrying guanidino and/or amidino groups.

The invention relates to methods by which a basic aqueous extraction medium can be cleared from organic compounds dissolved herein and is available for reuse.

The invention also relates to methods by which dissolved organic compounds present in a neutral or basic extraction medium can be aggregated and separated.

Furthermore, it was found that dissolved calcium compounds and undissolved calcium oxide compounds are appropriate to initiate aggregate formation of dissolved organic compounds, as has been found for the ionic copper compounds. However, it was found that the necessary amount of calcium ions or calcium oxides is considerably greater than in the case of ionic copper compounds. Furthermore, process control is more difficult with calcium compounds. Ionic calcium is not visually recognizable in the aqueous solution or emulsion since it does not lead to turbidity or colour change of the aqueous solutions/emulsions. Copper ions lead to a colouring of the aqueous medium which has a blue to green colour spectrum, depending on the pH of the solutions. This property is well suited for process control, while the concrete analysis of the actual calcium ion concentration is more problematic.

Unexpectedly, the addition of powdered calcium oxide compounds also initiated aggregation of organic compounds, although calcium oxide compounds are not soluble in water. The initialization of aggregate formation proceeds much slower than after addition of copper or calcium ions. Further, it has been found that there is an increase in the pH of the cleared process water with addition of calcium oxide compounds. The amount of copper ions required to initiate aggregate formation of the organic substance mixture is considerably less than the amount of dissolved calcium ions already present in the mixture of organic substances. Magnesium and zinc oxides also led to aggregate formation, while aluminium or copper oxides were not suitable for this purpose.

In a preferred embodiment the aggregation initializing process in step b) takes place by addition of oxide compounds of calcium, magnesium, or zinc.

Furthermore, the invention relates to a method, wherein the aqueous emulsion according to step a) contains at least one compound carrying guanidino and/or amidino groups, having a $K_{ow}$ of <6.3.

Particularly, the inventive process is suitable for aqueous emulsions that originate from the refining of a lipid phase.

The invention relates to methods in which the aqueous emulsion according to step a) originates from a refining a lipid phase.

Another particularly advantageous effect with the use of copper or calcium ions instead of calcium oxide compounds is that here removal of compounds carrying guanidino and/or amidino groups from the extraction mixture is much lower. Loss of compounds carrying guanidino and/or amidino groups is due to inclusion of an aqueous phase within the organic aggregates consisting of organic compounds and calcium oxide, during a aggregate initiation with calcium oxide. Furthermore, it could be shown that when using copper ion-containing solutions for the initiation of aggregation and clarification of the aqueous emulsion, the loss of compounds carrying guanidino and/or amidino groups is <10 wt % as compared to the amount of these compounds in the starting solution.

In addition, it could be shown that the separation of the aggregates by means of a filtration or a sedimentation with calcium oxide compounds in comparison to copper ions is associated with the separation of a larger amount of water. Therefore, copper ion-containing solutions are preferred for the present invention. By this means, a loss of compounds carrying guanidino and/or amidino groups from the cleared process water can be reduced to a minimum. According to the invention, the recovered process water phase contains at least 80 wt %, more preferably more than 85 wt %, and most preferably >90 wt % of compounds carrying guanidino and/or amidino groups compared to the amount of these compounds that was present in the aqueous emulsion before aggregation was initiated.

Therefore the invention relates to methods by which reprocessing and recycling of process water with compounds carrying guanidino and/or amidino groups can be achieved.

According to the invention, a reusable aqueous process solution with dissolved compounds carrying guanidino and/or amidino-groups is obtained.

Copper ions that remain in the clarified process water can also be completely removed with very simple methods if desirable. This can be accomplished easily, since—provided that the shift of the pH-value is not intentionally carried out e.g. by means of a buffer—the compounds carrying guanidino and/or amidino groups in the aqueous solution exhibit a isoelectronic charge, and thus they cannot be moved in a electrical field during a electrophoretic separation of the copper ions, so that electrodes, e.g. made of carbon, for the deposition of copper either can be placed directly in the process water or a electrophoretic separation with suitable membranes such as e.g. they are usual in the eletrodialysis, can be carried out. The electrophoretic separation can be performed by placing the electrodes directly into the process solution or by using an electrophoretic device with suitable membranes, which are unselective or selective, e.g., for separation of bivalent cations. This process step is possible with very little effort and can be carried out easily.

Even more advantageous is the separation of the dissolved copper ions through suitable cation-binding compounds. Suitable materials for this purpose are known from the prior art, such as ion exchange resins. By this means, purified aqueous solutions with compounds carrying guanidino and/or amidino groups are obtained, which can be re-used immediately for a renewed application. Therefore, this method is particularly suited with an unsurpassed ability to separate a large amount of dissolved organic compounds in a nano-emulsion with minimal effort in a very short time and to obtain aggregates of the separated organic compounds with minimal water content and, simultaneously, to recover clarified process water by simple means with almost complete recovery of dissolved compounds carrying guanidino and/or amidino groups.

A preferred embodiment of the inventive method is a procedure for clarification and purification of aqueous emulsions according to one of the embodiments of the invention, due to which an aqueous phase or process water is obtain, which is suitable for repeated use for the respective application.

Also preferred is the use of a purified process water phase with compounds carrying guanidino or amidino groups dissolved therein, for aqueous refining and/or cleaning and/or decomplexing process In addition to these surprising and beneficial effects, a very simple and therefore preferred dosing technique for the initiation of aggregation of organic compounds was found. As the aggregation of the dissolved organic compounds starts practically abruptly at a certain concentration of added copper ions, a modality for controlling the dosing of copper ions had to be found in order to avoid an unnecessary overtitration with copper ions which, in particular, has to be present in a large-scale plant.

Surprisingly, it was found that the aggregation always begins at the same colour spectrum and colour intensity of a solution according to the specific process conditions while adding and mixing a solution of copper ions. Thereafter, the aggregation process continues spontaneously and proceeds completely without need for further addition of copper ions.

A slightly green to turquoise transparent aqueous solution is obtained after complete sedimentation of aggregates or their removal by phase separation; in addition, the pH remains practically unchanged in relation to the pH of the baseline solution. This enables a precise dosage of copper ions, so that a subsequent extraction of copper ions may be carried out very economically.

For a complete precipitation of carboxylic acids from solutions with compounds carrying guanidino and/or amidino groups, which does not contain further organic compounds than these, a larger amount of copper ions is required than stoichiometrically required for a salt formation with contained carboxylic acid groups. In addition, it was shown that the initiation of aggregation according to the invention occurs independently from the amount of the carboxylic acids that were nano-emulsified in the mixture of organic substances. In the case of aqueous emulsion obtained from an aqueous refining process with a arginine solution, wherein the initiation of the aggregation has been triggered by copper ions directly or after the admixing of oleic acid, the amount of copper ions which was necessary for the complete separation of the organic compounds was only slightly higher in case of additional fatty acid than without this addition. A further investigation was carried out with the cleared aqueous solutions by adding an identical amount of oleic acid, as this was done in the previous investigation, and a renewed initiation of aggregation with copper compounds has been carried out. The required amount of copper-ions for the complete initiation of aggregation was about twice as high as the difference between the amount of added copper ions (without or with additional oleic acid) in the previous experiment.

In summary, it must be assumed that the unexpectedly effective aggregation formation, which can be achieved by the addition of copper ions, but also by addition of calcium ions and powdered forms of calcium oxide to the aqueous emulsions according to the invention, is due to a loss of the emulsifying capacity of compounds carrying guanidino and/or amidino groups towards dissolved organic constituents, preferably carboxylic acids, phospholipids, glycolipids, glyceroglycolipids, phenols, sterols, squalenes, plant dyes, such as chlorophylls and carotenes and/or sinapines, as well as flavoring substances thereby allowing self-assembly of hydrophobic or amphiphilic organic compounds, which further proceed spontaneously, thereby they separate from the aqueous phase. It must be assumed that intermolecular binding forces additionally contribute to aggregate formation between the organic compounds, and consequently a phase separation is better possible than if an adsorption of the organic compounds at an adsorbent would be performed.

Moreover, for a complete aggregation of carbonic acids, which are present in a nano-emulsified state by means of contained compounds carrying guanidino and/or amidino groups but which at the same time contains also other organic components than the said compounds, a lesser amount of copper ions for the aggregation of the organic compounds is required than for the case that only carbonic acids and said compounds carrying guanidino and/or amidino groups are present in the solution. Therefore, by the method according to the invention, an advantageous separation of solubilized carboxylic acids can be achieved with a lower need of copper ions in the simultaneous presence of other organic compounds; thus, a complete separation of the organic compounds is achieved together with the carboxylic acids.

Copper ions remaining in the process water, but also other ions listed herein, can be separated with the disclosed devices and a purified water phase can be obtained. This purification has the advantageous effect that the purified aqueous phase, which still contains compounds carrying guanidino and/or amidino groups and further compounds that are present at concentrations that do not interfere with other components in a further application, can be used directly for a renewed application, such as an aqueous refining process. Ionophoretric methods, such as electrophoresis or electrodialysis, are suitable for the removal of ions. Furthermore, ion exchange resins may be used. Therefore, a preferred method for the removal of copper ions, but also of other ions which remained in the clarified process water, is the use of adsorptive techniques or electrophoretic separation by elemental deposition or by an ion permeable membrane.

An embodiment of the method is the removal of copper (II) ions from the aqueous solution after step c).

A further preferred embodiment is the purification of the clarified water phase to obtain a re-usable process water phase. A further particularly advantageous effect of the present invention is the fact that initiation of aggregation of dissolved organic compounds takes place at ambient temperature as well as at temperatures <15° C., or until the freezing point of the solution in the same manner. This is of particularly interest when organic compounds shall be aggregated which easily hydrolyze in an aqueous or alkaline medium or degenerate or can be modified by enzymes that have been dissolved or by catalytically active substances. Due to aggregation and separation of the organic compounds under reduced temperatures such changes to can be reduced or even completely avoided.

It could be demonstrated that by this means phospholipids can be obtained that were not hydrolyzed, which derived from an aqueous extraction of vegetable oil, by using a solution with dissolved compounds carrying guanidino and/or amidino groups and mild process conditions whereby the phospholipids were aggregated in the aqueous emulsion with copper ions under cooled conditions. The fraction of phospholipids that was obtained by a solvent extraction procedure from the cooled aggregates, which took place under low temperature, exhibited virtually no hydrolysis. If the same procedure was performed at room temperature or elevated temperatures, there was a significant amount of phospholipid hydrolysis.

Therefore, the inventive method is also directed to the aggregation of readily decomposable organic compounds in order to separate and obtain these in an unchanged form from the aggregate phase.

A preferred embodiment of process step b) is the aggregation of easily decomposable organic compounds where the reaction mixture is cooled while and after initiation of aggregation.

Therefore, the inventive methods are also directed to obtain organic compounds or make them obtainable in a largely or completely unchanged form which can then be used in food, pet food, technical, cosmetic or pharmaceutical products.

In this respect, the invention relates to the use of separated organic compounds as food, pet food, technical, cosmetic, or pharmaceutical product or as a flavouring agent.

Neutral lipids, which are present in an emulsion or nano-emulsion consisting of compounds carrying guanidino and/or amidino groups and carboxylic acids and other organic compounds, cannot be separated from the nano-emulsion by physical means such as centrifugation or by increasing the temperature. In contrast, by means of the inventive method separation of the neutral lipids present in said emulsions or nano-emulsions can be obtained when the inventive initialization of aggregation is performed under elevated temperatures.

For this purpose, initiation of aggregation can be carried out as described before. However, at elevated temperatures of the emulsions containing neutral lipids are not being included in the organic aggregates and form a separate phase which floats on the aqueous phase due to the difference in their specific weight. Such separated phase of neural lipids can be easily separated from the aqueous phase consisting of compounds carrying guanidino and/or amidino groups by appropriate procedures. Therefore, a likewise particularly preferred variant of the inventive method, concerns heating of the emulsion or nano-emulsion consisting of dissolved compounds carrying guanidino and/or amidino groups and carboxylic acids as well as neutral lipids in order to separate the neutral lipids from the remaining organic compounds, wherein the neutral lipids float on top of the water phase and are recoverable as a fraction.

As expected, analysis of recovered lipid fractions has shown that they consist of neutral fats for the most part.

The separation of neutral lipids from an aqueous emulsion containing dissolved organic compounds by heating the emulsion before and/or during the initiation of aggregation according to the invention is a further preferred embodiment of the method.

Inventively is the receiving of neutral fats from an aqueous solution of organic compounds.

On the other hand, the aggregated organic compounds that were obtained under these process conditions were free of neutral fats. This can be very advantageous for the further use of the obtained organic compounds. Thus, substantially complete separation of neutral fats from extractable fractions consisting of phospholipids or glycolipids or carboxylic acid is very beneficial.

Therefore, the invention is also directed to the receiving and use of organic compounds which have only a minor content of neutral fats or contain virtually no residual neutral fats.

Further advantageous effects arise from the separation process and further use of the aggregated organic compounds. The already described effect of formation of very compact aggregation of the total organic compounds, which were present in the aqueous emulsions with compounds carrying guanidino and/or amidino groups, which causes a large displacement of the water phase and thus also the compounds carrying guanidine or amidine groups, results in the receipt of a mass of the organic compounds that is very compact and also has a low stickiness. Therefore, the separated complexed organic compounds can be further dewatered using centrifugal methods, such as a decanter and/or vibrating screens and/or filtration processes in order to obtain almost water-free organic matter. For small amounts of solids, filtration technology is favourable for complete removal of the organic aggregates. Thus, the organic aggregates can be easily removed by means of established procedures.

A preferred embodiment of process step c) is the use of decanters, separators or filter technology to separate an organic aggregate phase that contains a low proportion of water.

In organic aggregate phases, in which the content of residual water and/or the compounds carrying guanidino and/or amidino groups herein should be further reduced, it may be necessary to subject the aggregate phase obtained from the process step c) to an aqueous cleaning step. This can be done by aqueous cleaning solutions that are passed through the aggregate phase or the aggregate phase is suspended in the aqueous cleaning solution. Then, one of the methods described above can be performed to separate and compact the organic aggregate phase. The aqueous cleaning solution may be pure (preferably low ion or ion-free) water or they contain an acid or a base.

A preferred method for reducing the residual water content and/or the amount of compounds carrying guanidino and/or amidino groups from the organic aggregate phase obtained after process stage c) is an after-treatment of the organic aggregate phase with an aqueous washing step, followed by a renewed phase separation and a separation of the phases from each other.

This also improves the shelf life of the organic aggregate phase and saves energy costs for water withdrawal in case dry starting material for further processing is required. Furthermore, transportation costs can be reduced by this means.

In certain applications it can be necessary to reduce the residual water content further; in this case drying of the organic aggregation phase is performed. For this purpose, methods are available from the prior art such as vacuum drying or the passage of an inert gas (e.g., nitrogen) or a hot air that is passed through the aggregate phase.

A preferred embodiment is the drying of the organic aggregate phase subsequent to the process step c).

The shelf life of many organic compounds that are included in the organic aggregates, such as proteins, glycolipids or lipoproteins can be increased up to indefinite time when they have been dried.

Therefore, the use of organic compounds, obtained according to one of the inventive procedures, that has a long shelf life accomplished by drying of organic compounds is preferred. Preferred is the use of organic matter that is preserved by drying as food, pet food, technical, cosmetic or pharmaceutical product or as a flavouring agent.

Surprisingly, the aggregate phases that were obtained by copper ions, but also by the other ions and oxide compounds according to the invention, exhibited surprisingly good storage stability, even without drying. Aggregate phases obtained from a refining process of rapeseed oil that have been stored for more than 6 months without further preservation measures (e.g., heat application or radiation) and at room temperature in a closed vessel showed no growth of fungi or microorganisms. Furthermore, the aggregates could be fractioned by the use of solvent. Moreover, it was shown that organic components can be recovered in a largely unaltered form.

A particularly preferred embodiment of the inventive process is directed to the production of storage-stable forms of organic compounds with low water content, which have been aggregated from an aqueous emulsion.

Also preferred is the storage of organic compounds with minor or no decomposition obtained by the inventive aggregation after process step c).

Another decisive advantage is that aggregated organic compounds can be separated into individual compound classes which are in a chemically virtually unchanged form with herein disclosed methods as could be shown.

Therefore, the method according to the invention is also preferred for the gentle preparation and fractionation of organic compounds, and preferably of carboxylic acids, but also of phospholipids, glycolipids, glyceroglycolipids, phenols, sterols, squalenes, plant dyes, such as chlorophylls and carotenes and/or sinapines from lipid phases, and especially preferred of proteins, flavors, waxes, fatty alcohols, fragrances and flavoring agents, carboxylic acids, but also of phospholipids, glycolipids, glyceroglycolipids, phenols, sterols, squalenes, plant dyes, such as chlorophylls and carotenes and/or sinapines from lipid phases.

The inventive aggregation of organic compounds that can be obtained by copper ions in emulsion enables aggregation of >85 wt %, more preferably >90 wt %, and most >95 wt % and most of all to >98 wt % of the organic compounds that have been dissolved in a solution with dissolved compounds carrying guanidino and/or amidino groups; however, the beneficial aggregation initiation can also be achieved by calcium ions or calcium oxide. Among substances that release calcium ions calcium chloride ($CaCl_2$) is preferred. Among further suitable ions which permit initiation of aggregation according to the invention, magnesium (II), zinc (II) and iron (II) and iron (III) and aluminium are mentioned. In principle, these ions can be supplied as salts with any counter ion in an aqueous solution where they dissociate. Particularly advantageous and therefore preferred are chloride salts. Also preferred are salts from sulfates or acetates. Also conceivable are e.g. tartrates, oxalates, carbonates, and borates. The combination of 2 or more of these salts or compounds is possible in principle and can be useful in conditions where various organic compounds are present in the aqueous emulsion, which exhibit varying degrees in the initialization of aggregation by the agents. In such cases, the required total amount of cations or oxide compounds can be reduced by combining the aggregating agents. A combination may also be desired when one of the cations could chemically react with one of the organic compounds. The probability for such a reaction to occur can be reduced by a combination of aggregating agents, which can be applied in process step b), due to the fact that the concentrations of the single aggregating agent can be reduced.

The preferred use of the salts is in the form of aqueous solutions for the initiation of aggregation. For this purpose, they are dissolved in a preferably low-ion or ion-free water. The compounds used for initiation of aggregation are preferably completely dissolved, that means that they are in a dissociated form. The concentrations of ionic copper and calcium and magnesium compounds used for initiating the aggregation according to the invention is essentially dependent on the process parameters. If adding of a larger volume of liquid is undesirable, the ion concentration can be increased up to the respective solubility limit, or, on the other hand if it is desired to use a low amount of aggregation agents, their concentration can be set to a minimum and the liquid volume can be increased. Preferred ion concentrations are in the range between 0.001 and 3 mol/l, more preferably between 0.01 and 2 mol/l, and most preferably between 0.1 and 1 mol/l.

The salts that can be used for the inventive initiation of aggregation are also referred herein as aggregation initiators.

The temperature at which the aggregating agents are dissolved and used is irrelevant, as long as they completely dissociate. For this purpose, it may be necessary in individual cases to increase the temperature of the aqueous solution. Both the aggregation initiator-containing aqueous solution, as well as the emulsion with compounds carrying guanidino and/or amidino groups and the dissolved organic compounds can be used together at any temperature. However, preferred is a temperature between 1 and 101° C., more preferably between 15° and 75° C., more preferably between 18° and 45° C., and most preferably between 25 and 35° C.

Preferred is a method in which step b) is carried out at a maximum temperature of 75° C.

The addition of the aggregation initiator-containing aqueous solutions to emulsions with compounds carrying guanidino and/or amidino groups and the dissolved organic compounds can be performed continuously or discontinuously, e.g., by dropwise addition. Furthermore, combinations of the two dosing regimens are possible. Preferred is a combination of the dosing regimens, whereas a quantity according to experience of the dissolved aggregation initiators is added and mixed initially, followed by drop-wise application in order to detect initiation of the aggregation. The quantity of aggregation initiator that have to be added to initiate the aggregation in the emulsion with dissolved compounds carrying guanidino and/or amidino groups and organic compounds must be determined individually in any application.

The dose finding can be recognized very easily by the fact that solid material aggregates can be recognized with the naked eye, while at the same time forming a clear aqueous phase. The beginning of aggregate formation can be best appreciated in an unstirred, i.e., not agitated, emulsion. At low agitation this initiation is nevertheless also recognized. The aggregation initiation takes place even with strong agitation of the emulsion with compounds carrying guanidino and/or amidino groups and organic compounds. However, a sufficient amount of aggregation initiator which leads to a complete aggregation of the organic compounds can be poorly estimated in an agitated emulsion. Therefore, it is preferred to control the amount of dissolved aggregation initiator that is required for complete aggregation of the organic compounds by continuous process monitoring. This makes the process economically very attractive. Furthermore, it was shown that the visual impression of the formation of a free water phase can be objectified by a change in the size distribution of the particles within the emulsion. With the appearance of a clear water phase, which occurs after initialization of aggregation, the size of measurable particles initially present in the emulsion that is in the range of 10 and 1000 nm (diameter) in more than 90% of all particles, enlarges, whereby the particles/aggregates in the clear water phase have a size of >10 µm in >90% of all measurable particles. In the water phase, there are practically no particles which are less than 1000 nm, which explains the optical effect of clarification of the emulsion. This can best be illustrated by the established processing technology of dynamic laser light scattering (DLS), which is available as remote method and for continuous measurements.

In a preferred embodiment of the inventive procedure, process control is performed by means of detection of a free water phase and/or of the formation of aggregates, which are >10 µm in >90% of all measurable particles.

Process control, however, is also possible by other known techniques. Conductivity and the ion concentration of the aqueous emulsion change by addition of ionic solutions, so that process control can be accomplished by means of conductivity measurement or determining the ion concentration by using suitable measuring probes. In practical application, these parameters can be used for controlling of aqueous emulsions, in which a little variability of the dissolved compounds exists. Their determination, which can carried out, e.g., during determination of the required minimum concentration, can be done by measuring the actual values of control parameters at the time of initiation of aggregation, which leads to the complete aggregation of the organic compounds. In a large-scale application, these parameter values can then be used to control the dosing. Other measurement methods concern the viscometry of the emulsions. It has been found that the viscosity of the aqueous emulsion increases with the addition of the aggregate initiating agents. This increase is significantly greater when the aggregate initiating agent is an oxide as compared to dissolved ions. With the formation of a free water phase, the viscosity of the aqueous reaction mixture decreases; thus, the continuous measurement of the viscosity is also suitable for process control; determination of parameters that describe the process can be determined as described above. Furthermore, also the specific weight of the emulsion shows specific variations during the course of the aggregation of the organic compounds.

In a particularly preferred embodiment of the inventive initiation of aggregation, the process is controlled and monitored by determination of the change of colour and/or colour intensity and/or transparency of the reaction mixture and/or size and size distribution of particles in the forming water phase during addition of copper ions to the aqueous reaction mixture.

Using the values of the colour spectrum and/or intensity of colour and/or transparency of the reaction mixture that are present at the time of initiation of aggregation with copper ions, it can be reliably predicted whether the amount of copper ions is sufficient for a henceforth self-sustaining aggregation process of the organic compounds up to complete removal of organic compounds from the aqueous solution with compounds carrying guanidino and/or amidino groups.

Unnecessary overdosing can be avoided in this way. If the aggregation process still does not proceed to completeness, further copper ions may be added until the aggregation is complete. Moreover, analytical devices for both remote investigations but also for online process monitoring of the colour spectrum and the intensity of colour and transparency are available. Determination of the exact process parameters which must match in order to predict a complete aggregation with copper ions can be established during an investigation for determination of the minimal dosage required, as described below and in the examples.

In a further preferred embodiment of the process, in step b) analysis of the colour of the aqueous emulsion and/or colour intensity and/or its optical transparency, and/or a determination of the particle sizes or particle size distribution herein is conducted for controlling the dosage for initiation of aggregation, performed continuously or discontinuously.

Furthermore, it could be demonstrated that it is remarkably easier to dissolve copper initiated aggregates consisting of phospholipids, dyes (here especially chlorophylls), phenols among others in a organic solvent than after the precipitation of organic compounds which were achieved by the addition of an acid or by the initiation of aggregation by calcium salts or calcium oxide.

As further disclosed in the following, it is possible to separate the aggregated organic mixtures into individual classes of organic compounds.

Surprisingly, it was found that in particular in aggregates of organic compounds, which were obtained by copper ions, the organic constituents could be separated more precisely with organic solvents than in extractions performed on aggregates obtained with calcium or other cations or calcium oxide. Fractionation of organic compounds aggregated by copper ions was also much easier than was the case in organic aggregates which had been obtained after precipitation with an acid. In addition, copper ions complexed with the organic compounds can be recovered by an aqueous extraction step with the aqueous phase from an organic solvent phase with suspended or dissolved organic aggregates.

A preferred embodiment of the process is the recovery of aggregation initiators from a complexed organic aggregate phase by dissolution with organic solvents and an aqueous washing step.

Therefore, the complexation organic compounds that are present in an emulsion or nano-emulsion consisting of compounds carrying guanidino and/or amidino groups and carboxylic acids with copper ion is a particularly advantageous embodiment for the separation of dissolved organic compounds.

In another preferred embodiment, complexing of the dissolved organic constituents is achieved by alkaline earth metal oxides and metal oxides by suspending them in the aqueous medium. This is particularly advantageous if a clarification of the dissolved organic compounds in a nano-emulsion consisting of compounds carrying guanidino and/or amidino groups and carboxylic acids is desired. After a short time aggregates form and sediment spontaneously, while at the same time the process water clarifies. The final separation can be performed then, as described above, by means of decanters and/or sieving- and/or filtering techniques.

Preferred oxide compounds which are known to be not soluble in water are, e.g., calcium oxide, zinc oxide, and magnesium oxide. Despite a poor solubility in water, these compounds may decompose with time; thus, it is advantageous to perform this separation step at room temperature or under refrigerated conditions. However, this cannot prevent decomposition, so there may be formation of hydroxides, whereby the pH of the process water may increase. If only a small amount of oxides are suspended, there is only a small increase in pH; however, the aggregation reaction proceeds slowly. When an excess of the required amount of oxide is used, aggregation develops very rapidly and is complete; however, the pH rises significantly to values >13. This is not desirable and, as described above, requires a more intense purification of the process water and thus unnecessary process costs. The actual amount of oxides that is required for a complete aggregation of the organic compounds cannot be calculated and must be determined by a trial and therefore must be determined individually for every application. In order to do so, a study to determine the required minimum dosage is used, as described herein. In a preferred embodiment, these oxide compounds are applied under continuous pH control. An increase to a prespecified value, which has to be determined for each application, represents then the upper limit for the addition of the oxide compounds. In a preferred embodiment, the process is controlled by measuring the pH of the reaction mixture.

In this respect, the procedure according to the invention provides a simple and inexpensive method for purification of process water with compounds carrying guanidino and/or amidino groups, wherein preferably >95 wt. % of all organic compounds, more preferably >98 wt. % all organic compounds and most preferably >99 wt. % of all organic compounds, other than the well-soluble compounds carrying guanidino and/or amidino groups are removed from the process water. This includes in particular the separation of previously nano-emulsified carboxylic acids of which >98 wt. % and most preferably >99 wt. % are removed by aggregation from an aqueous emulsion with compounds carrying guanidino and/or amidino groups It has been shown that organic compounds which remain in a clarified or purified water phase do not deteriorate the reusability of solutions with compounds carrying guanidino and/or amidino groups in a renewed application for a nano-emulsifying or elusive cleaning or decomplexation procedure because these compounds have a very high hydrophilicity and are not taken up by or do not distribute in a lipid phase deemed to be refined.

In this regard, the inventive method also focuses on the nearly complete removal of carboxylic acids from an aqueous process medium that have been used for a refining procedure and which have been separated from a lipid phase, in order to make them obtainable.

The aggregates of organic compounds obtained after their separation from the aqueous phase have a residual water content of preferably <30 wt. %, more preferably of <20 wt. %, more preferably of <15 wt. %, and most preferably <10 wt. % and can be used immediately or after a further removal of water for a fractionation. It has been found that such fractionations can be achieved by solvents, which are known to persons skilled in the art, in a few steps. For this purpose, non-polar solvent, such as octane, hexane, heptane, petrol ether, dimethyl ether, and low polar solvents, such as $CHCl_3$ or $CH_2Cl_2$ or polar solvents, such as ethyl acetate, and alcohols, such as isopropyl alcohol, methanol, ethanol, 1-butanol, as well as small amounts of water can be used, optionally with the addition of an acid or a base. Further, combinations of the aforementioned classes of compounds are possible. In this case fractions of organic compound classes are obtained which are characterized by, e.g., a >90% solubility in a methanol phase and such that have at least a solubility >80% in petrol ether, and compounds that have a >75% solubility in an alcohol. Thereby, the organic compounds obtained from the mixture of organic substances can be separated in classes that exhibit a purity of preferably >70%, more preferably of >80% and most preferably >85% by sequential separation with one or more solvents.

Therefore, the invention relates to carboxylic acids, phospholipids, glycolipids, glyceroglycolipids, glycosphingolipids, chlorophylls, carotenoids, squalenes, phenols, sinapines, peptides, proteins, carbohydrates, lipoproteins, carbohydrates, flavoring agents, waxes and/or fatty alcohols, available to one of methods described herein, wherein the carboxylic acids, phospholipids, glycolipids, glyceroglycolipids, glycosphingolipids, chlorophylls, carotenoids, squalenes, phenols, sinapins, peptides, proteins, carbohydrates, lipoproteins, flavoring agents, waxes and/or fatty alcohols are obtained with a purity of each compound class of >75%.

Furthermore, the invention relates to methods to receive fractions of carboxylic acids, phospholipids, glycolipids, glyceroglycolipids, glycosphingolipids, chlorophylls, carotenoids, squalenes, phenols, sinapines, peptides, proteins, carbohydrates, lipoproteins, flavoring agents, waxes and/or fatty alcohols by the use of one of the methods described herein, wherein the carboxylic acids, phospholipids, glycolipids, glyceroglycolipids, glycosphingolipids, chlorophylls, carotenoids, squalenes, phenols, sinapines, peptides, proteins, carbohydrates, lipoproteins, flavoring agents, waxes and/or fatty alcohols that are obtained have a purity of each compound class of >75%.

The sequence of solvent that can be used to fraction and separate the organic compounds best can be determined for each of the obtained organic substance mixtures which contain different types and numbers of organic compounds. The same applies for the necessary proportions of solvents in relation to the mass of the organic compounds to be fractionated as well as the solvents with one another. The separation of the solvent phase can be achieved by phase separation; optionally, a centrifugal separation for increasing the separation efficiency is required. I. In principle, any acid, that is known by the skilled person in the art, for the acidification can be used, but preferred are HCl, sulfuric acid, and oxalic acid. Base-forming substances are also known to the skilled person, such as sodium hydroxide. Then the fractionated organic compounds present in the solvent phase can be obtained as a solid by evaporation of the solvents, for example, by means of vacuum evaporation.

The resulting solids can then be resuspended in suitable solvents or solvent mixtures and be further purified herewith or purification is carried out from the organic solvent phase, in which they were received. Then, fractions of organic compounds can be obtained by techniques from the prior art in which a purity of >90%, more preferably >95%, and most preferably >98%, for compounds from the classes of carboxylic acids, phospholipids, glycolipids, glyceroglycolipids, glycosphingolipids, chlorophylls, carotenoids, squalenes, phenols, sinapines, peptides, proteins, carbohydrates, lipoproteins, flavoring agents, waxes and/or fatty alcohols, available by one of methods described herein, wherein the carboxylic acids, phospholipids, glycolipids, glyceroglycolipids, glycosphingolipids, chlorophylls, carotenoids, squalenes, phenols, sinapines, peptides, proteins, carbohydrates, lipoproteins, flavoring agents, waxes, fatty alcohols and other organic compounds have been complexed by aggregation according to the invention. Further preferred is the recovery of >90%, more preferably >95% and most preferably >98% of the copper ions that have been administered during the process of aggregation formation. These separation methods can be carried out under normal temperature conditions, preferably they are between 0 and 120° C., more preferably between 10° and 50° C., and most preferably between 15° and 35° C. The exposure times are subject to the process conditions. The extractions have to be carried out under the occupational safety and accident protection guidelines, preferably in closed systems.

Thus, one embodiment of the invention relates to a process for the recovery of carboxylic acids, phospholipids, glycolipids, glyceroglycolipids, glycosphingolipids, chlorophylls, carotenoids, squalenes, phenols, sinapines, peptides, proteins, carbohydrates, lipoproteins, flavoring agents, waxes and/or fatty alcohols.

In this respect, the inventive method is also directed to the production and use of high-purity organic compounds that exhibit preferably a >90%, more preferably a >95% and most preferably a >98% chemically and structurally unaltered conformation as compared to that present in the lipid phase from which they were separated by an aqueous extraction with compounds carrying guanidino and/or amidino groups, and which can be assigned to substance classes of carboxylic acids, phospholipids, glycolipids, glyceroglycolipids, glycosphingolipids, chlorophylls, carotenoids, squalene, phenols, sinapines, peptides, proteins, carbohydrates, lipoproteins, flavoring agents, waxes and/or fatty alcohols, and other organic compounds.

It was further found that the inventive method for initiation of aggregation of organic compounds does not work or works significantly worse when an aqueous emulsion which contains the same organic compounds is used, but in which the aqueous solution used for the refining process has been prepared using a base-forming compound, such as sodium hydroxide. It should be noted that solvation of the organic compounds cannot be obtained or mostly does not occur as this is the case in aqueous emulsions with compounds carrying guanidino and/or amidino groups. There were practically no solids retrievable from aqueous emulsions that had been obtained from the refining of e.g. rapeseed and camelina oils, by a passage through a 20 μm filtration support; when the aqueous refining solution contained compounds carrying guanidino and/or amidino groups, however, a great amount of solids were present which cause clogging of such a filter, when the aqueous refining solutions were based on a base-forming compound, such as NaOH or sodium carbonate. In this respect, it can be assumed that larger aggregates of organic compounds are already present in the aqueous emulsions which have formed due to the base-forming compounds, however, the further addition of cations that have been disclosed herein, did not or insufficiently initiate aggregation of organic compounds in those aqueous emulsions.

Aqueous nano-emulsions consisting of compounds carrying guanidino and/or amidino groups and carboxylic acids are also suitable to break up and dissolve complexed mixtures of organic compounds and to dissolve them in the aqueous medium, thereby emulsions or suspensions are established. The dissolved organic compounds do have amphiphilic properties in a high proportion, but they can also be largely apolar. Such emulsions or suspensions can be prepared in a variety of industrial areas. For example, it could be shown that complexed organic compounds in biomass, which could not be dissolved by other means where dissolvable by aqueous nano-emulsions consisting of dissolved compounds carrying guanidino and/or amidino groups and carboxylic acids, which enabled separation of the dissolved organic compounds from those emulsions by one of the inventive procedures.

As an example, it could be shown that organic compounds associated to pressing residues of plants, such as plant seeds, can thus be separated. The same holds true for intermediate products or residuals in the processing of food or for carcass disposal. Furthermore, separation of organic compounds and fruit pulp, which remained on the cores or shells of plant fruits, is very easily accomplishable with such nano-emulsions. Still usable organic compounds from fermentation processes or bioreactors can be transferred into and separated with the water phase of the nano-emulsions.

The low surface tension of such nano-emulsions also results in the penetration of the water phase into hydrophobic, strongly complexed aggregates. It was shown that organic compounds enclosed in dried sewage sludge granules can be dissolved and separated for the most part from inorganic constituents by nano-emulsions. These nano-emulsions also penetrate into porous rocks and are able to dissolve complexes of organic compounds enclosed by virtually pure lipids and enable their transport into the water phase.

Surprisingly, the aggregation method according to the invention is also suitable to aggregate and separate organic compounds which have been dissolved by a nano-emulsifying treatment of complex and complexed mixtures which have been liberated from their organic or inorganic matrix. The methods described herein can be applied in the same way in such aqueous emulsions and suspensions.

A particularly preferred embodiment of the inventive aggregation process is the aggregation and separation of organic compounds from aqueous emulsions which originate from a nano-emulsifying cleaning and/or refining processes.

Aggregation of organic compound can be initiated in the same manner with copper or calcium ions, and calcium oxide in such emulsions, that is effective even after the addition of a small amount of the substances according to the invention; however, the amount of aggregation initializing agents that must be applied for an aggregation initiation which causes a complete aggregation of the dissolved organic compounds and a clear water phase which still contains the dissolved guanidine or amide group-containing compounds must be determined for the respective application. The aggregates contain very different proportions of organic compound classes according to the different origin and the area of application of aqueous nano-emulsions. For example, it was shown that a high proportion of proteins, in addition to lipoproteins, glycolipids, carbohydrates, lignins and phenols, have also been found in emulsions obtained during the aqueous extraction of press residues from plant seeds. On the other hand, organic compounds were separated during the nanoemulsive purification of sewage sludge residues by the aggregation initiation according to the invention, such as, for example, phospholipids and proteins as well as amino acids.

Therefore, the method is also directed to a process in which organic compounds can be obtained and used, which originate from a nano-emulsifying cleaning or decomplexation process or a nano-emulsifying refining process with an aqueous solution with compounds carrying guanidino and/or amidino groups or nano-emulsion of an aqueous solution containing compounds carrying guanidino and/or amidino groups and one or more carboxylic acids.

Preferred is the obtaining and use of carboxylic acids, phospholipids, glycolipids, glyceroglycolipids, glycosphingolipids, chlorophylls, carotenoids, squalenes, phenols, sinapines, peptides, proteins, carbohydrates, lipoproteins, flavours, waxes and/or fatty alcohols obtained from a nano-emulsifying cleaning and/or refining processes.

A particularly preferred embodiment of the aggregation initiation according to the invention is directed to the aggregation and separation of organic compounds from aqueous emulsions, which were obtained from a decomplexation and/or purification processes by means of nano-emulsions, composed of an aqueous solution containing dissolved compounds carrying guanidino and/or amidino groups and one or more carboxylic acids.

Methods

A Process for Producing an Aqueous Emulsion According to Process Step a):

In one embodiment of the present invention, prepurification of a lipid phase is performed before contacting the lipid phase with a solution containing compounds carrying guanidino and/or amidino groups. The prepurification is preferably executed by adding water or an aqueous solution, which has a preferred pH range between 7.0 and 14, more preferably between 9.5 and 13.5, and most preferably between 11.5 and 13.0, which is mixed with the lipid phase and a prepurified lipid phase is obtained by preferably centrifugal phase separation. In a further embodiment, the aqueous solution for pretreatment contains a base which is preferably chosen from sodium hydroxide, potassium hydroxide, ammonium hydroxide, sodium carbonate, sodium hydrogen carbonate, sodium bicarbonate, potassium carbonate and potassium hydrogen carbonate, sodium metasilicate, sodium borate.

In another embodiment, the prepurification of the lipid phase is carried out in analogy to the basic prepurification procedure using an acid or acidic solution. Acidic prepurification is carried out by the undiluted acid, or an acid-containing aqueous solution with a pH between 1.0 and 5, more preferably between 1.7 and 4, and most preferably between 3 and 3.5. Acids that can be used to adjust the pH are preferably selected from phosphoric acid, sulfuric acid, citric acid, and oxalic acid.

The appropriate concentrations and the mixing ratio of usable basic and/or acidic aqueous solutions to be used for prepurification of the oil phase can in principle be selected freely and can be easily determined by a person skilled in the art. Preferably, the concentrations of the basic solutions are between 0.1 and 3 molar, more preferably between 0.5 and 2 molar, and most preferably between 0.8 and 1.5 molar. The volume ratio of the basic water phase and the oil phase should be preferably between 0.3 and 5 vol %, more preferably between 0.3 and 4 vol %, and most preferably between 1.5 and 3 vol %.

Acids may be added undiluted or as an aqueous acid solution to the lipid phase. The undiluted acid is added preferably in a volume ratio between 0.1 and 2.0 vol %, more preferred between 0.2 and 1.0 vol %, and most preferred between 0.3 and 1.0 vol %. The aqueous acid solution is preferably added in a volume ratio between 0.5 and 5.0 vol %, more preferably between 0.8 and 2.5 vol %, and most preferably between 1.0 and 2.0 vol %.

The addition of the basic and acidic solutions for prepurification can performed continuously or in a batch process. Mixing of the two phases can be performed with stirring elements or with an intensive mixer (e.g., a rotor-stator mixer), provided that this does not lead to stable emulsions that cannot by separated by means of centrifugation. The aim of the prepurification procedure is to remove hydratable gums from the lipid phase.

The exposure time for applications in a batch process is between 1 and 30 minutes, more preferably between 4 and 25 minutes, and most preferably between 5 and 10 minutes. When a continuous mixing (so-called in-line method) is performed, the residence time of the phases to be mixed within a mixer is between 0.5 seconds and 5 minutes, more preferably between 1 second and 1 minute, and most preferably between 1.5 seconds and 20 seconds. The preferred temperatures of the lipid phase and the added mixed aqueous phase for an intensive mixture is between 15 and 45° C., more preferably between 20 and 35° C., and most preferably between 25 and 30° C. The separation of the aqueous phase from the emulsion may preferably be carried out by a centrifugal separation method, preferred is the use of centrifuges, separators, and decanters. The duration of a centrifugal separation and the separation method depend on the product specifications (water content, viscosity, etc.) and must be determined individually. Preferably, a centrifugation is carried out for 2-15 minutes, more preferably for 8-12 minutes. The residence time within a separator or decanter is preferably 2-60 seconds, more preferably 10-30 seconds. The centrifugal acceleration is preferably selected between 2,000 and 12,000×g, and more preferably between 4,000 and 10,000×g. The temperature during phase separation should be preferably between 15 and 60° C., more preferably between 20 and 45° C., and most preferably between 25 and 35° C.

The effectiveness of the prepurification can be determined by determining the phosphorus content and the amount of mucus substances that are present in the lipid phase to be refined. Suitable are preferably lipid phase that exhibit a phosphorus content of <100 ppm (or 100 mg/kg), and a content of unsaponifiable organic matter <0.5 wt %. However, also lipid phases that are above these specifications can be refined with solutions of compounds carrying guanidino and/or amidino groups. If there is a need for a prepurification process, the selection of an aqueous degumming process, which is a treatment with an acid (undiluted or as an aqueous solution) or a base can be freely selected, in principle, so there are different ways to perform a prepurification treatment: I. sole acid treatment, II. sole base treatment, III. first acid treatment then base treatment, IV. first base treatment then acid treatment, V. repeated acid treatment, VI. repeated treatment with base. Selection of the appropriate and cost-effective process can be done easily by a skilled person. Practical experience has shown, however, that if prepurification is required, the procedure should be started with the use of an aqueous acid solution, followed by, if still necessary, an aqueous base treatment, which represents the most preferred embodiment.

Aqueous Emulsions According to the Invention for the Aggregation Initiation According to Method Step a)

An essential component to accomplish the inventive aggregation of organic compounds, relays on the preparation of an aqueous phase containing one or more compounds carrying guanidino and/or amidino-groups.

The aqueous phases containing organic compounds according to the invention can in principle originate from all purification or refining processes of lipid phases. The relation between the volume of the water phase or the proportion of the herein dissolved compounds carrying guanidino and/or amidino groups and of herein dissolved organic compounds do vary from application to application. The same applies to the concentrations of compounds carrying guanidino and/or amidino groups which are required. However, the following standard operating procedures are preferred embodiments, in particular, for refining of oils and fats.

The preferable concentration of compounds carrying guanidino and/or amidino groups, which are preferably dissolved in low-ion or ion-free water, is determined in one embodiment on the basis of the actual acid value of the lipid phase to be refined, which can be determined by a methanol titration with KOH.

The number of carboxylic acid groups which can be derived therefrom can be used to calculate the amount of weight of compounds carrying guanidino and/or amidino groups. Preferably, it is desired that at least the same or a greater number of guanidino or amidino groups, which are present in free and ionized form, as carboxylic groups are present in the aqueous solutions. Thus, the determinable molar ratio between the guanidino or amidino groups and the whole of the free or releasable carboxyl groups of organic compounds or carboxylic acids is preferably >1:1. Preferably the molar ratio between the determinable carboxylic acids and guanidino and/or amidino groups should be 1:3, more preferably 1:2.2 and most preferably 1:1.3.

The molarity of the compounds carrying guanidino and/or amidino groups in the solutions are preferably 0.001 to 0.8 molar, more preferably 0.05 to 0.7 mol/l, more preferably 0.1 to 0.65 mol/l and most preferably 0.4 to 0.6 mol/l. Since the interaction of the guanidino or amidino groups is ensured even at ambient temperatures, the preferred temperature at which the addition of the aqueous solutions (containing dissolved compounds carrying guanidino and/or amidino groups) according to the invention may take place, between 10 and 50° C., more preferably between 28 and 40° C., and most preferably between 25 and 35° C. The volume ratio between the lipid phase and the aqueous phase containing compounds carrying guanidino and/or amidino groups that is admixed with an intensive mixer is in principle unimportant. To obtain the most beneficial resource-saving effects of the procedure, however, the volume of the water phase should be reduced to the minimum necessary. Therefore, in one embodiment, the volume ratio (v/v) of the aqueous solution to the lipid phase is in a range of 5 to 0.08 vol %, and more preferably 3 to 0.1 vol %.

The volume and concentration ratios may need to be adjusted, especially when emulsion-forming compounds are present in lipid phases, such as glycolipids, which can be solvated by compounds carrying guanidino and/or amidino groups with an aqueous solution, whereby these compounds are then not available for the separation of carboxylic acids. Therefore, in one embodiment it may be necessary to select a greater volume and/or concentration ratio of the aqueous solutions containing compounds carrying guanidino and/or amidino groups to the lipid phases to be refined.

In a further advantageous embodiment, mixing of the lipid phase with the aqueous solution containing compounds carrying guanidino and/or amidino groups is performed with an intensive mixing device. By this means, a nano-emulsifying mixing/cleaning process can be established. For this purpose, mixing systems that allow a high interaction rate of the two phases are suitable. Therefore systems are preferred that are used also for homogenization of liquids. The intensive mixing is applied at atmospheric pressure and a temperature in the range between 10 and 90° C., preferably between 15 and 70° C., more preferably between 20 and 60° C., and particularly preferably between 25 and 50° C. Therefore, the mixing and preferably intense mixing is performed at low temperatures of preferably below 70° C., more preferably below 65° C., more preferably below 60° C., more preferably below 55° C., still more preferably of below 50° C., and even more preferably below 45° C. By the use of low temperatures during mixing as well as during subsequent separation, done for example by centrifugation, and during subsequent processings, it can be ensured that hydrolysis of the organic compounds does not take place.

Thus, the present invention is also directed to a method to perform separations of phospholipids, glycolipids, glyceroglycolipids, vitamins as well as other organic compounds that are easily hydrolysable and originate from a lipid phase, in which no or almost no hydrolysis of those compounds takes place.

The phase separation for obtaining the aqueous emulsion of step a) is preferably performed by a centrifugal separation technique from the prior art. Preferably, phase separation is accomplished by a separator, further preferred is a through-put volume of more than 3 m$^3$/h, more preferably >100 m$^3$/h, and most preferably >0.400 m$^3$/h. In principle, the separation of the aqueous emulsion from the lipid phase can take place immediately after completion of a mixture or an intensive mixing process. On the other hand, if required by the process flow, the emulsified or nano-emulsified reaction mixture to be separated is first collected in a storage tank. The duration of storage depends solely on the chemical stability of the compounds present in the nano-emulsified reaction solution and the process conditions. Preferably, the phase separation is performed immediately subsequent to the mixing or intensive mixing process. The temperature selected during separating of the emulsified or nano-emulsified reaction mixture can in principle be the same as was selected during production of the same. However, it may also be advantageous to vary the temperature and to select a higher temperature, when thereby, e.g., the separation capacity of the separation device is increased or on the other hand to lower the temperature when, e.g., the separation efficacy of the compounds carrying guanidino and/or amidino groups is increased in those nano-emulsions. In general, a temperature range is preferred that is between 15 and 50° C., more preferably between 18 and 40° C., and most preferably between 25 and 35° C. The residence time in a separator or a centrifuge is essentially determined by the apparatus-specific properties. Generally, for economic embodiment the lowest possible residence time in a separation device is preferred; such a preferred residence time in a separator is <10 minutes, more preferably <5 minutes, and most preferably <2 minutes and for centrifuges the preferred residence time is <15 minutes, more preferably <10 minutes, and most preferably <8 minutes. The selection of the centrifugal force depends on the difference in density of the two phases to be separated and can be determined individually. Preferred are acceleration forces between 1,000 and 15,000× g, more preferably between 2,000 and 12,000×g, and most preferably between 3,000 and 10,000×g.

Preferred is a separation into an oil and a water phase in which an oil and a water phase are obtained that consist to >90 vol %, more preferably to >97 vol %, and most preferably >99 vol % of a pure oil or pure water phase.

Processes for obtaining an aqueous emulsion according to process step a) thus comprise on the one hand the direct refining of lipid phase with a solution containing compounds carrying guanidino and/or amidino groups and on the other hand, refining of lipid phases with solutions that contain compounds carrying guanidino and/or amidino groups of lipid phases that have previously undergone a prepurification procedure with an acid or basic (alkali) step or combinations thereof.

Production of Nano-Emulsions and Dosages for Nano-Emulsifying Cleanings/Refinement Procedures.

Nano-emulsions that allow nano emulsifying refinement of lipid phases or cleaning or decomplexation of organic matter complexes consist of compounds carrying guanidino and/or amidino groups fully dissolved in a preferably low-ion or ion-free water. Production of a nano-emulsion can be done with a liquid or liquefied form of a carboxylic acid, as disclosed herein. In this case, the molar ratio between the solubilizing compounds carrying guanidino and/or amidino groups and all of carboxylic acids deemed to be nano-emulsified should be in a range between 1:1 and 1:0.0001, more preferably between 1:0.9 and 1:0.001, even more preferably between 1:0.85 and 1:0.01, and most preferably between 1:0.7 and 1:0.1. The decisive factor is the solubility of the two compounds. Due to the large number of possible combinations it may therefore be necessary to select a lower concentration of the carboxylic acid in order to ensure that a nano-emulsion as defined herein is obtained. A nano-emulsion is present if a clear liquid that remains thermodynamically stable for months is obtained. Analytically, droplets or particles that have a sizes less than 100 nm, preferably less than 50 nm, more preferable less than 10 nm, and in particular less than 3 nm can be determined in such nano-emulsions, by which they are characterized. Dynamic laser beam spectroscopy (dynamic light scattering, DLS) can be used as an analytic tool. Here, the hydrodynamic diameters of the particles are measured, to which the above mentioned values refer.

Nano-emulsions can be prepared by mixing in carboxylic acids into aqueous solution with already completely dissolved compounds carrying guanidino and/or amidino groups. The resulting initial increase in viscosity, and the possible formation of solids can by completely reversed by heating the solution, while stirring continuously for up to 24 hours.

The concentration of the compounds carrying guanidino and/or amidino groups and that of the aqueous nano-emulsion can be freely selected depending on the application, provided that the solubility product is not exceeded. For arginine, for instance; this is reached at concentration of about 0.6 mol/l.

The concentration carboxylic acid(s) or a carboxylic acid mixture to be dissolved depends on the solubility of the compounds carrying guanidino and/or amidino groups. Even though the concentration of the compounds carrying guanidino and/or amidino groups is mainly determined by process conditions, and also by the individual solubility of compounds carrying guanidino and/or amidino groups, the preferred concentration range is between 0.001 and 0.8 mol/l, more preferably between 0.01 and 0.6 mol/l, and most preferably between 0.1 and 0.5 mol/l.

In one embodiment application of nano-emulsions can be performed manually or automated. This can be accomplished as described by a drop-wise addition or by a jet of the aqueous nano-emulsion that is admixed using a mixing device, for instance a high shear force mixer (homogenizer).

The nano-emulsions can be admixed to the mixture of organic compounds or to a lipid phase to be refined, respectively, in any quantity ratio. Thus, a preferred volume ratio of a nano-emulsion to the lipid phase or to an organic compound mixture is in the range between 0.5:1 and 100:1, more preferred between 0.6:1. and 10:1, even more preferable between 0.8:1 and 5:1. However, low dosages are preferable for an economic use, which are in a range between 0.49:1 and 0.0001:1, more preferred between 0.2:1 and 0.001, and most preferred between 0.1:1 and 0.01:1.

The preparation of nano-emulsions can be also accomplished with the carboxylic acids that are already in the lipid phase. A complete nano-emulsification of all carboxylic acids present in the lipid phase is a particularly preferred embodiment for the preparation of nano-emulsions to be used in a refining process. The aforementioned concentrations, volumes, and volume ratios are applicable in similar fashion. It is preferred to determine the concentration of existing and quantifiable carboxylic acids that are in the lipid phase initially, in order to set the parameters for the desired nano-emulsion. Such a determination can be done with established methods such as the determination of the acid number or by a gas chromatography. If the concentration of the carboxylic acids unknown, the aqueous solution with compounds carrying guanidino and/or amidino groups can be admixed to the lipid phase with the techniques previously mentioned as long as a liquid lipid phase has formed. The term "liquid lipid phase" herein means that the viscosity of the obtained reaction mixture is preferably in the range from 1 to $2 \times 10^4$ mPa·s, more preferably from 1.2 to $1 \times 10^4$ mPa·s and most preferably from 1.3 to $5 \times 10^3$ mPa·s.

For the production of a nano-emulsion in a lipid phase, it may be necessary to increase the temperature of the water phase with compounds carrying guanidino and/or amidino groups and/or increase the temperature of the lipid phase in order to dissolve the carboxylic acids. This allows considerable acceleration in the production of nano-emulsions and also decreases the viscosity of the resulting nano-emulsion. Provided that the nano-emulsion is produced only by an intensive mixing procedure, it may be necessary to heat the lipid phase. The preferred temperature range for preparation of such nano-emulsions is between 15 and 60° C., more preferably between 20 and 50° C., and most preferred between 25 and 40° C.

A further important parameter to be adjusted is the viscosity of separately produced nano-emulsions, i.e., an aqueous solution containing compounds carrying guanidino and/or amidino-groups, as disclosed herein, with herein nano-emulsified carboxylic acids, or of nano-emulsions produced by intensive admixture of an aqueous solution containing compounds carrying guanidino and/or amidino groups to a lipid phase that contains carboxylic acids. In principle, it can be said that the viscosity increases upon attainment of an equimolar ratio between the number of acid groups and guanidino and/or amidino groups as a function of their absolute concentrations. The resulting viscosity has to be determined specifically for the components used. For a nano-emulsifying refinement of a lipid phase, it is advantageous if the resulting nano-emulsion or emulsion is liquid, i.e. it flows easily. This property can be determined by appropriate methods, such as a falling ball viscometer. The preferred viscosity values are between 1 and $5 \times 10^3$ mPa s, more preferred between 1 and $1 \times 10^3$ mPa s, and most preferred between 1 to $1 \times 10^2$ mPa s.

Provided that the lipid phase already has a higher viscosity, the viscosity of the produced nano-emulsifying reaction mixture can be adjusted by a larger volume of the aqueous solution with the solubilizing compounds carrying guanidino and/or amidino groups or by the use of a lower concentration of the compounds carrying guanidino and/or amidino groups herein.

Preferred compounds for the preparation of the nano-emulsions that contain guanidino or amidino groups are arginine and arginine derivatives, as described herein. For the production of nano-emulsions the use of oleic acid or stearic acid is preferred. In another preferred embodiment nano-emulsions are produced with phytic acid or sinapinic acid.

The solutions or nano-emulsions usable for the refining or decomplexation may contain apart from compounds carrying guanidino or amidino groups other compounds which can cause an improvement of the refining or decomplexation properties of the solutions or nano-emulsions. For this purpose, non-ionic but also ionic tensides are preferred as well as alcohols up to a certain extent and solvents miscible with the aqueous solutions.

The emulsion that has to be provided for the process step a) is thus an aqueous emulsion that may contain a plurality of organic compounds in any composition or concentration in a soluble or suspended form, whereas the aqueous solution contains at least one base-forming compound and whereas the base-forming compound can be a compound containing guanidino and/or amidino groups. The aqueous emulsion can be a nano-emulsion, a micro-emulsion, or a macro-emulsion. It can derive from a refining/cleaning procedure of a lipid phase or from a decomplexation process and at the same time have a viscosity that allows the emulsion to flow.

Procedures for Process Control and Monitoring

The course of the inventive aggregation of organic compounds in aqueous emulsions and nano-emulsions with compounds carrying guanidino and/or amidino groups and carboxylic acids can be monitored and controlled by various methods.

A preferred embodiment is the determination of the colour reaction and colour intensity occurring by addition of copper-containing compounds for process guidance and process control.

For this purpose, a specific value of an absorption spectrum of a light beam can be used to detect the concentration of the copper ions in the reaction mixture, whereby the dosing of a solution containing copper ions can be controlled by a control technique in order to reach/match with a predefined colour scale value. Since the colour spectrum of a solution containing copper compound is also pH dependent, it is necessary to determine this value and, if necessary, a correction factor has to be incorporated into the control technology. Since the temperature can also have an effect on the colour spectrum, temperature measurements should be carried out, which can optionally be used to correct the dosing. Both, the wavelength of a transmitted or emitted light, as well as its intensity or attenuation are used for controlling the dosing of solutions containing aggregating compounds according to the invention. The applicability of the various methods depends on the particular application.

In the case of complex mixtures of substances with a high concentration of organic compounds, a transmittance of a light beam is often not possible, so that here, if necessary, a dilution must be carried out. For this purpose, a sample is taken from the reaction mixture and analyzed separately (externally) for the concentration of the copper ion present, and for the degree of turbidity or the colour spectrum.

At low concentrations and less complex mixtures of organic compounds, the transmittance of a light beam is possible through a low layer thickness of the liquid volume, so that for the determination of the colour spectrum a device for continuous spectral analysis can be used. With a greater turbidity, it is advantageous to perform a spectral analysis of the adsorption in the wavelength range of visible light and with an infrared wavelength. This allows correction of a reduced or altered colour intensity, which is caused by a corpuscular turbidity (compensation of turbidity).

Both techniques can be carried out in continuous operation mode under real-time conditions. For this purpose, an appropriate measuring instrument can be placed into the mixing reactor and brought into contact with the reaction liquid. On the other hand, it is conceivable to install a viewing panel that allows an observation of the reaction mixture, as well as the possibility to perform an analysis by light beam transmission or emission.

pH Monitoring

The colour reaction also depends on the pH that is present in the aqueous emulsions. For that reason the pH should be continuously monitored and the pH level should be used to control the dosing of solutions with the inventive compounds to initiate aggregation. pH monitoring is a preferred measurement tool for the dosing of calcium compounds and alkaline earth metal oxides and metal oxides.

Viscometry

Throughout the aggregation process the viscosity of the reaction liquids exhibits characteristic courses. After a period of latency, there is a sharp increase in viscosity to the maximum, and then the viscosity drops sharply. Reaction liquids that were centrifuged after the onset of the drop in viscosity, showed a clear supernatant. In these cases, the further addition of copper or calcium ions had no effect on the further course of aggregation. Therefore, methods for determination of viscosity, which takes place preferentially in the reaction mixture, are suitable for optimizing of process control, or to determine the required minimum amount of copper ions or calcium compounds or other cations of the invention for aggregation initiation. However, the measurement is also applicable to control aggregation initiation by oxide compounds.

Determination can be performed with suitable viscometers as known in the art. Particularly suitable are so-called process viscometers, which can also be used for continuous process monitoring and control. Suitable here are rotational, vibrational, or quartz viscometer.

Determination of Calcium Ion Concentrations

Addition of calcium ions to an aqueous emulsion initially leads to only a slow rise of the calcium ion concentration. Upon reaching the visible initiation of aggregation the ion concentration increases rapidly. The calcium ion concentration can be measured continuously with an ion-selective measuring rod sensor (e.g., CA60, SI Analytics, Germany). This procedure is therefore suitable for process monitoring and control.

The aforementioned measuring methods are suitable for the control of the dosage of aggregation agents. An individual or a plurality of measured values which allows prediction of a sufficient dosage of the aggregating agent can be determined in a study on the minimal amount of aggregation compounds required. The parameter values found there can be used for control techniques from the prior art and for an automatic dosing system.

A preferred embodiment is the determination of a minimum dose of aggregating agents due to a prior investigation, in order to optimally adjust automated dosing of the aggregation process.

Preferred is the use of an automated control and metering technology for aggregating agents for process economization.

Mixing

The ionic copper compounds are admixed in a dissolved form in an aqueous medium which has preferably a low content of ions or is preferably ion-free.

This is preferably performed in the form of a low volume addition that is performed continuously or intermittently (e.g., in a dropwise fashion). Discontinuous addition in small portions is preferred, since judgment whether a sufficient amount has been administered can be made only after mixing the reaction solution. By doing so, overdosing can be avoided.

In another procedure according to the invention in step b) discontinuous addition of the aqueous solution containing copper(II) ions and/or calcium ions to the aqueous emulsion is performed.

Mixing is preferably performed by a stirring device which exerts no high shear forces on the liquid because the initialized aggregation promotes further aggregation and breaking up of aggregates that have already formed unnecessarily increases the consumption of copper and other cations as well as oxide compounds. Thus, a preferred embodiment is the use of a stirring device for mixing of the solution containing aggregation compounds with the aqueous emulsion. Examples include helical or fork mixer in an application with a low rotational speed.

The invention relates to a method, wherein the mixing in step b) is performed with a stirring device (laminar stirrer).

The process of mixing can be performed continuously or discontinuously and depends on the process conditions.

Compounds for Initialization of Aggregation

The terms aggregation compounds, aggregating or aggregation initializing compounds are used interchangeably herein. Preferred compounds according to the invention to initialize and perform aggregation of organic compounds which are dissolved in aqueous emulsions or nano-emulsions with compounds carrying guanidino and/or amidino groups and carboxylic acids are water-soluble compounds of copper. Further preferred are calcium, magnesium, iron, zinc, and aluminium ions. Preferred are chloride salts of the aforementioned cations, but also salts with carboxylic acids such as carbonates, acetates, tartrates, oxalates. The latter are preferred when the smallest possible amount of counter ions should remain in the process water, since carboxylic acids do adhere to the complexing organic aggregates with increasing carbon chain length and thus are removed from the process water along with the aggregate phase. Suitable counter-ions also include the following: sulfate, sulfide, nitrate, phosphate, hydroxide, fluoride, selenide, telluride, arsenide, bromide, borate, oxalate, citrate, and ascorbate. Here, the use of sulfate or citrate is a preferred embodiment. The application is preferably performed with compounds in completely dissociated form in water which has preferably a low content of ions or is preferably ion-free.

The concentration has to be adapted to the amount of organic compounds to be aggregated and the viscosity of the nano-emulsion. In principle, very dilute or highly concentrated solutions can be used. Preferred are solutions that have a concentration of the cations initiating aggregation in the range between 0.001 and 3 molar, more preferably between 0.01 and 2 molar, and most preferably between 0.1 and 1 molar. When solutions of copper salts with a high concentration should be used, but also in case of the use of other/further salts, the pH of the solution should be adjusted, which should be preferably in a range between 3 and 8, more preferred between 5 and 7, and further more preferably between 6 and 7. In another embodiment, a suitable buffer may be added to achieve a pH value of the cation-containing solution, as well as the other solutions of the invention.

The required amount of cations must be determined for each reaction mixture, preferably this is done with an investigation on the required minimum dose as described herein. The quantity or mass of cations required for the aggregation initiation is preferably <5 wt %, more preferably <3 wt %, and most preferably <1 wt % based on the weight of separated organic compounds. The volume of the aqueous solution containing the aggregation initiating cations can be chosen freely. Preferably, a volume ratio of the aqueous solution to the aqueous emulsion of <8 vol % is selected, more preferred it is <5 vol %, and most preferred it is <2 vol %. Also, combinations of the salts can be used.

For aggregation initiation undissolved oxide compounds are also suitable. For this purpose, preferred oxides are oxides of calcium, magnesium, and zinc. Among these calcium oxide is preferred. The oxides can be admixed in powdered or microcrystalline form by stirring into the emulsion with the compounds carrying guanidino and/or amidino groups and carboxylic acids and dissolved organic compounds. In one embodiment the oxide compounds are applied in the form of an aqueous suspension. This may be advantageous when a great amount of oxide compounds have to be applied, since the already dispersed oxides do distribute more readily in the emulsions or nano-emulsions. When oxide compounds are applied, progressive aggregation can be initialized by forced mixing, thereafter continuous or intermittent addition and mixing are preferred. The progress of the aggregation can be followed by the change in turbidity or the formation of larger aggregates with formation of a free water phase, as well as a pH change of the reaction solution, and thus these parameters can be used to control further dosage. It is very advantageous to initially stir in the oxide powder quickly and then perform stirring only intermittently to ensure mixing of the reaction mixture. The amount of oxide compounds that is required for a sufficient initiation of aggregation must be determined individually for each reaction mixture. Preferred is an amount of oxides that has to be applied that is <15 wt %, more preferably is <10 wt %, and most preferably is <8 wt % in relation to the weight of organic compounds to be separated. Also, combinations of oxide compounds can be used.

The invention also relates to the combination of aggregation compounds selected from one or more cationic compounds present in dissolved form and/or one or more oxide compounds which are present in powdered or suspended form and are added to the reaction mixture in any sequence, combination, and mass proportions.

Separation of Aggregated Organic Compounds in Process Step c)

The aggregation initiation, which is obtained due to the substances and methods of the invention, leads to the formation of large aggregates which sediment, leaving a clear aqueous phase. In order to, condense the aggregates, the free water phase can be easily separated by a decanter. Alternatively, the entire content of the reactor can be completely separated from aggregates and possible remaining suspended solids by means of a sieve resulting in a solid phase and water phase. The aggregate initiation by calcium oxide compounds or other oxide compounds usually a little more water remain in the solid phase, so that it can be meaningful, to rinse the solid phase with a sufficient amount of a water phase which has preferably a low content of ions or is preferably ion-free in order to wash out the entrapped compounds carrying a guanidine and/or amidino groups. Washing liquids that can be used for that purpose may also contain an acid or a weak alkali, as far as the organic compounds are not deteriorated hereby. Subsequently, the water content can be removed from the solid phase by pressing or by centrifugal separation methods. The aggregated organic compounds can be dried by a moderate elevation of the temperature, e.g., by to passage of heated air through the aggregate masses. Alternatively, a vacuum drying under normal temperature can be performed.

Removal of residual water prolongs shelf life of the organic compounds and makes subsequent fractionation of organic compounds easier; therefore, drying of the solid phase to a residual water content <5 wt % is a preferred embodiment of the process. If organic aggregates contain components that may decompose at normal or elevated temperatures aggregation, separation and drying can be performed under refrigerated conditions. Thereby, "refrigerated" means a temperature between 1 and 18° C. In a preferred embodiment the aggregation initiation and the separation of the aggregate phase are performed at a temperature of 1-18° C.

Provided that neutral fats are to be separated from an aqueous emulsion, it is advantageous to heat the reaction mixture and to maintain an elevated temperature throughout the process. Elevated temperature means thereby a temperature range between 45 and 101° C. The neutral fats separate thereby from the aggregating organic compounds and form a separate phase that is visible on top of the water phase. Hereby, separation of the phase of neutral fats can be performed on an industrial scale with known techniques.

In a further preferred embodiment, the aggregation initiation and separation of the aggregate phase is performed at a temperature between 45 and 101° C.

If an aggregation according to the invention is successfully completed, the water phase of the former aqueous emulsion is optically clear and contains virtually no suspended matter. It was shown that in the situation where the visual impression of a clear water phase is present, which can be objectified by turbidimetry, no corpuscular compounds can be detected, corresponding to low values of light scattering (FTU values <10). Since virtually all organic compounds can be coagulated by lowering the emulsion pH to <1.0, acidification (pH<1.0) is a very simple method (acid test) to test whether an effective depletion of organic compounds from the aqueous emulsion has been achieved. A negative acid test means that there are no or only minimal amounts (<0.5 wt % with respect to the water phase) of organic solids are precipitated. It was shown that after successful aggregation of organic compounds, no more solids can be separated by addition of an acid to the clarified water phase. In a practical manner, a small sample (e.g. 10 ml) can be taken from the reaction mixture during a large scale process and centrifuged (e.g., 3000×g for 10 minutes). If, on the one hand, a clear water phase and, on the other hand, a compact solid phase (if organic compounds have been present in the reaction solution), are obtained, the acid test is carried out with the separated water phase. The phase separation, which takes place after a sufficient aggregation formation (negative acid test), can be carried out with the separation procedures described in the prior art. Preferred is a test to verify sufficient or complete aggregation of organic compounds in the reaction solution by an acid test prior to carrying out process step c).

Process for Decomplexation, Break Up, and Fractionation of Aggregated Organic Compounds Since the composition of the aggregated organic compounds varies from application to application, the selection of suitable organic and/or aqueous (basic or acidic) solvents as well as their order of application for decomplexation and fractionation of the organic aggregates must be determined individually. Chloroform is a preferred solvent of the aggregate phase of organic compounds, by which most of the organic compounds present can be dissolved or suspend. By addition of a polar solvent, such as methanol, polar compounds, such as phospholipids, can be dissolved and separated easily by phase separation. Addition of a small amount of an acid, such as HCl, and/or water can increase the separation efficiency. Alternatively, the aggregated mass can be suspended in a highly non-polar solvent, such as hexane or dimethyl ether initially, followed by separation of dyes using, e.g., a medium-chain alcohol, i.e., monools or diols having 2 to 6 carbon atoms, such as 1-propanol, 1-butanol, 1,2-butanediol, 1,3-butanediol, 1,4-butanediol, 1-pentanol, 1,2-pentanediol, 1,3-pentanediol, 1,4-pentanediol, or 1,5-pentanediol. The fractionation of the solvent phases is carried out by means of a continuous or discontinuous process, such as centrifugation, preservation or distillation. The various organic compounds present in the solvent phases can be separated by established techniques, such as chromatographic adsorption or evaporation of the solvent, thereby producing organic solids that can be used directly or are matter of further purification.

Separation Methods

The term "centrifugal phase separation", as used herein, refers to a separation of phases by utilizing a centrifugal acceleration. It comprises in particular methods such as centrifugation and preferably suitable devices for this purpose, such as decanters and separators that are known in the art.

Emulsions which are formed in the refining process of lipid phases with aqueous solutions containing compounds carrying guanidino and/or amidino groups must be separated into a lipid phase and an aqueous emulsion phase by the described process of centrifugal phase separation. Preference is given to separators that enable continuous separation. Separators devices consist of plates or cylinders which rotate with an even or uneven speed thereby building up pressure and tensile forces. Therefore, a particularly preferred embodiment for the phase separation of the aqueous emulsions (containing compounds carrying guanidino and/or amidino groups) from the lipid phase, is to carry out the phase separation with a separator. Under certain circumstances, it may be necessary to remove residual suspended solids from the clarified water phase by passing it through a sieve or a filter.

The aggregated organic compounds can be separated by sedimentation or filtration with devices known in the art such as sieves, filters, centrifugal phase accelerator like separators or decanters. When using filters, the selection of the nominal pore sizes depends on the size of the aggregates to be separated, in general preferred is a nominal pore sizes of <100 μm, more preferably of <50 μm, and most preferably of <20 μm which is suitable for a complete separation of the solids and suspended matter of the organic compounds. For centrifugal phase separation, the preferred centrifugal acceleration to be used is in the range between 2,000 and 12,000×g, and more preferred between 4,000 and 10,000×g. The temperature during phase separation should preferably be between 15 and 60° C., more preferably between 20 and 45° C., and most preferably between 25 and 35° C.

Purifying the Cleared Water Phase

The cleared water phases obtained after separation of the aggregated organic compounds may contain cations and anions that have not been complexed with the organic aggregates. Also a solution of cations as well as the formation of hydroxide ions in case of using the inventive oxide compounds is possible. The presence and concentration of the respective ions or oxides can be determined by methods of the prior art (for example, ICP). Oxides can be separated by using appropriate filter materials (e.g., membrane filter with a pore size of 0.04 μm). This is not the case for ions. But the separation can be carried out with established procedures, e.g., electrophoresis or electrodialysis. By this means, deposition of the cations in elemental form at a cathode is possible, or the ions are passed and separated through/by ion-selective membranes by applying an electrical field. A further possibility is an adsorption of ions by means of adsorbents, e.g. ion exchange resins are suitable for this purpose. A further possibility consists in a chemical binding of the ions. For example, calcium and magnesium ions can be aggregated by the addition of phosphoric acid to form an insoluble complex, which can easily be separated from the water phase by means of customary filters. If this is performed under pH control, removal of cations without protonation of compounds carrying guanidino and/or amidino groups can be achieved. Therefore, preferably, complexing of ions in the clarified water phase is performed under continuous pH control.

Definitions

Reaction Mixture

The term "reaction mixture", as used herein, refers to an aqueous emulsion or nano-emulsion consisting of compounds carrying guanidino and/or amidino groups and dissolved organic compounds (including carboxylic acids) that are present along with cations and/or oxide compounds, which are suitable for aggregation initiation according to the invention.

Lipid Phase

The term "lipid phase", as used herein, refers to all lipophilic organic carbon compounds of biological origin. In particular mixtures of biological origin are included, which may be obtained from plants, algae, animals, and/or microorganisms that have a water content of <10% and a content of lipophilic substances comprising of monoacylglycerides, diacylglycerols, and/or triacylglycerides which have total amounts of >70 wt % or >75 wt % or >80 wt % or >85 wt % or >90 wt % or >95 wt %. Those lipid phases may for example be extracts of oleaginous fruits, such as seeds or germs of rapeseeds, sunflower, soya, camelina, jatropha, palm, castor bean, or originate from microorganisms, e.g., from algae and microalgae or from animal fats and oils. It is irrelevant whether the lipid phase is a suspension, emulsion, or a colloidal liquid.

The lipid phase may derive from extracts or may be an extraction phase containing lipophilic compounds from a previously performed separation or extraction, which has an amount of organic solvents or hydrocarbon compounds that is >50 wt %.

Preferred lipid phases are vegetable oils, in particular pressing and extracting oils from oil plant seeds. Further preferred are animal fats. Further preferred are non-polar aliphatic or cyclic hydrocarbon compounds. These lipid phases are distinguished in that >95% of the compounds herein are non-polar.

Among the lipid phase according to the definition used herein count, inter alia, Acai oil, Acrocomia oil, almond oil, babassu oil, blackcurrant seed oil, borage seed oil, rapeseed oil, cashew oil, castor oil, coconut oil, coriander oil, corn oil, cottonseed oil, flaxseed oil, grape seed oil, hazelnut oil, other nut oils, hemp seed oil, jatropha oil, jojoba oil, macadamia nut oil, mango oil, meadowfoam seed oil, mustard oil, neat's foot oil, olive oil, palm oil, palm kernel oil, palm olein oil, peanut oil, pecan oil, pine nut oil, pistachio oil, poppy seed oil, rice bran oil, safflower oil, *camellia* oil, sesame oil, shea butter oil, soybean oil, sunflower oil, tall oil, Tsubaki oil, walnut oil, varieties of "natural" oils with altered fatty acid compositions via genetically modified organisms or traditional breeds, *Neochloris oleoabundans* oil, *Scenedesmus dimorphus* oil, *Euglena gracilis* oil, *Phaeodactylum tricornutum* oil, *Pleurochrysis carterae* oil, *Prymnesium parvum* oil, *Tetraselmis chuii* oil, *Tetraselmis suecica* oil, *Isochrysis galbana* oil, *Nannochloropsis salina* oil, *Botryococcus braunii* oil, Dunaliellatertiolecta oil Nannochloris oil, *spirulina* oil, Chlorophyceae oil, Bacilliarophyta oil, a mixture of the previously mentioned oils or animal oils (especially marine animals oils), algae oils, oils from bran recoveries e.g. rice bran oil, and biodiesel.

Cleaning and Dekomplexing Procedures with Aqueous Solutions or Nano-Emulsions

Solutions containing dissolved compounds carrying guanidino and/or amidino groups as well as nano-emulsions, as described herein, can be used for cleaning and decomplexation of organic and inorganic materials in order to decompose, delocalize, peel, hydrate, or mobilize organic compounds and to transfer them in a water phase of emulsion which is formed. Among the many applications arising inevitable therefrom, this method is particularly usable as purification process, e.g. in case of grease traps or filters, food production, plant and cell extracts or plant products, cell lysates, sewage sludge, sands, and rocks.

Refining of a Lipid Phase

The phrase "refining of a lipid phase" means in this context a process in which a lipid phase is cleaned by an aqueous solution or nano-emulsion as described herein. This also includes methods described herein where an aqueous solution containing compounds carrying guanidino and/or amidino groups is mixed with a lipid phase, and then phase separation is performed. This also includes in particular the nano-emulsifying refinings of lipid phases.

Aqueous Emulsion of the Process Step a)

The term "aqueous emulsion", as used herein, concerns water-based nano-, micro-, or macro-emulsions, as described herein, but does also include suspensions of organic compounds. These emulsions contain organic compounds as described herein, aside to compounds carrying guanidino and/or amidino groups as defined herein. The concentrations of compounds carrying guanidino and/or amidino groups and one or more organic compounds may be up to exceeding the solubility limit in the aqueous emulsion. The aqueous emulsions may be optically transparent or consist of a turbid solution. The viscosity can range from 0.5 mPa s to 3,000 mPa s, the pH can range from 5 to 14. The aqueous emulsions can contain a buffer system, solvents, or one or more co-surfactants. They can be generated artificially by adding organic compounds or originate from a refining, cleaning or decomplexing process. The organic compounds as listed herein can be present in the aqueous emulsions in a dissolved or partially complexed form.

Aggregation

Generally speaking aggregation means an accumulation or collection of atoms or molecules and/or ions that forms greater conglomerates, the aggregate. The accumulation or aggregation is caused by Van-der-Waals forces, hydrogen bonding, and/or other chemical or physico-chemical bond types.

Aggregated Phase

Aggregated phase means the precipitate or a sediment (accumulation) of aggregates which is produced by spontaneous phase separation or centrifugal separation.

Nano-Emulsion

A nano-emulsion is present when a water-based solution containing a water-soluble surfactant and an amphiphilic or lipophilic compound remains thermodynamically stable over months as a clear liquid. Droplet or particle sizes in such a nano-emulsion are less than 100 nm, preferably less than 50 nm, more preferably less than 10 nm and further preferred and in particular preferred less than 3 nm. This can be documented by means of dynamic laser beam spectroscopy (dynamic light scattering, DLS). By doing so, the hydrodynamic diameter of the particles is measured. It also relates to the above information about the sizes.

Emulsion

The term "emulsion", as used herein, referrer to all forms of liquid mixtures that consist of a water phase and an oil or fat phase. The proportion among the liquid phases is variable. A special case represents nano-emulsions. A nano-emulsion may exist within a macro-emulsion. To make it clear, an emulsion is not a transparent nano-emulsion, but instead an emulsion is created by an oil-in-water or water-in-oil mixture which has a significant turbidity; the term "macro-emulsion" is also synonymously used for the term emulsion. Emulsions may also incorporate hydrophobic organic compounds that do not match with the term lipid as defined herein, which are in a dissolved state, in an aqueous solution with compounds carrying guanidino and/or amidino-groups. In such a case, there are transitions to suspensions, in which organic compounds may also be present in the form of aggregates.

Free Water Phase

The term "free aqueous phase" or "free water phase" is characterized by an optically transparent volume of water, in which aggregates can be visualized, exhibiting sharp contours. The free water phases evolve from an aqueous emulsion or suspension, which have a turbid appearance and are opaque at a layer thickness of 3 mm. The free water phase is optically transparent at this distance. This can be objectified, e.g., by determining the size and the number of particles in the water phase, e.g., by the use of DLS. By this means, it can be observed that in the presence of a free water phase particles that are less than 1 μm are removed, then measurable particles are >than 10 μm.

Clarified Water Phase

The term "clarified water phase" or "cleared water phase", as used herein, means the aqueous phase which is obtained after the inventive aggregation of organic compounds and their separation in process step c), which is carried out in an aqueous emulsion consisting of a dissolved compounds carrying guanidino and/or amidino groups with dissolved organic compounds herein. The term "clarified" stands for an optically clear solution in which no or only few suspended solids are present. This can be quantified by means of a turbidity measurement. A value of 10 FTU is not exceeded. However, the term clarified also includes removal of dissolved organic compounds. This can be checked by an acid test, whereby the pH-value of the clarified water phase is adjusted to pH<1.0 by the addition of an acid (e.g. HCl). Organic compounds are thereby coagulated and can be separated by means of centrifugal separation techniques or filtration and quantified. Further methods can be used for quantification of organic compounds that are still herein, e.g., HPLC and/or MS.

Purified Water Phase

The term "purified water phase" is used for a clarified water phase or clarified process water phase, as defined herein, that is depleted from the added ions or oxides that have been administered to initiate aggregation, whereas a reduction of >95 wt % of the ions and/or oxides have been achieved. This can be verified by elemental analysis (e.g., ICP) or atomic absorption spectroscopy.

Organic Compounds

The term "organic compounds" includes all organic compounds of biogenic origin which can be obtained by a refining, extraction, or decomplexation procedure or a cleaning operation with one of the processes described herein from biogenic or fossil materials and which can be dissolved in an aqueous emulsion according to the invention containing dissolved compounds carrying guanidino and/or amidino groups. This includes nano-emulsions containing dissolved compounds carrying guanidino and/or amidino groups. According to the different origin of these emulsions, organic compounds of various substance groups are found that can be present as a singular substance class, but mostly, are present in various combinations and in different proportions.

In the following section only the essential material groups are listed, to which the organic compounds can be assigned, but are not limited to, waxes, wax acids, lingins hydroxy and, mycolic acids, fatty acids with cyclic hydrocarbon structures such as shikimic acid or 2-hydroxy-11-cycloheptyl undecanoic acid, mannosterylerythritol lipid, dyes such as carotene and carotenoids, chlorophylls, and their degradation products, further phenols, phytosterols, especially ß-sitosterol and campesterol and sigmasterol, sterols, sinapine, squalene. Furthermore, phytoestrogens, such as isoflavones or lignans. Furthermore, steroids and derivatives thereof, such as saponins, glycolipids and glyceroglycolipids and glycosphingolipids, rhamnolipids, sophrolipids, trehalose lipids, mannosterylerythritol lipids. Likewise, polysaccharides, pectins such as rhamnogalacturonans and polygalacturon acid ester, arabinans (homoglycans), galactans and arabinogalactan, further pectic acid and amidopectines. Furthermore, phospholipids, particularly phosphatidylinositol, phosphatides such as phosphoinositol, further one long-chain or cyclic carbon compounds, fatty alcohols, hydroxy and epoxy fatty acids. Likewise glycosides, lipoproteins, lignins, phytate or phytic acid and glucoinosilate. Proteins, including albumin, globulins, oleosines, vitamins, such as retinol (vitamin A) and derivatives, such as, retinoic acid, riboflavin (vitamin B2), pantothenic acid (vitamin B5), biotin (vitamin B7), folic acid (vitamin B9), cobalamins (vitamin B12), calcitriol (vitamin D) and derivatives, tocopherols (vitamin E) and tocotrienols, phylloquinone (vitamin K) and menaquinone. Furthermore, tannins, terpenoids, curcumanoids, xanthones. And also sugar compounds, amino acids, peptides, including polypeptides, as well as carbohydrates such as glycogen. Included are also carboxylic acids, flavours, or taste and odor compounds, dyes, phospholipids and glycolipids, waxes and wax acids and fatty alcohols that are further defined below.

Carboxylic Acids

Carboxylic acids are organic compounds which carry one or more carboxyl groups. A distinction between aliphatic, aromatic, and heterocyclic carboxylic acids can be made. Aliphatic forms of carboxylic acids, also called alkanoic acids, are fatty acids which are listed in the following.

Fatty Acids

Generally, fatty acids are aliphatic carbon chains having a carboxylic acid group. The carbon atoms may be linked with a single bond (saturated fatty acids) or with a double bond bridges (unsaturated fatty acids); these double bonds can be in a cis- or trans-configuration. As defined herein, the term fatty acid referred to fatty acids which have more than 4 consecutive carbon atoms in addition to the carboxyl group. Examples of linear saturated fatty acids are decanoic acid (capric acid), dodecanoic acid (lauric acid), tetradecanoic acid (myristic acid), hexadecanoic acid (palmitic acid), octadecanoic acid (stearic acid), n-eicosanoic acid (arachic acid), and n-docosanoic acid (behenic acid).

Examples of fatty acids that are mono-olefins are myristoleic acid, palmitoleic acid, petroselinic acid, oleic acid, elaidic acid, gondoic acid and erucic acid.

Examples of polyolefins fatty acids are linoleic acid, linolenic acid, punicic acid, arachidonic acid and nervonic acid.

Fatty acids may also carry functional groups such as vernolic acid, ricinoleic acid and lactobacillic acid. Functional groups can be also terminal cyclic carbon residues. Examples of "fatty acids" are hexanoic acid, octanoic acid, decanoic acid, dodecanoic acid, tetradecanoic acid, hexadecanoic acid, heptadecanoic acid, octadecanoic acid, eicosanoic acid, docosanoic acid, tetracosanoic acid, cis-9-tetradecenoic acid, cis-9-hexadecenoic acid, cis-6-octadecenoic acid, cis-9-octadecenoic acid, cis-11-octadecenoic acid, cis-9-eicosenoic acid, Cis-11-eicosenoic acid, cis-13-docosenoic acid, cis-15-tetracosenoic acid, t9-octadecenoic acid, t11-octadecenoic acid, t3-hexadecenoic acid, 9,12-octadecadienoic acid, 6,9,12-octadecatrienoic acid, 8,11,14 eicosatrienoic acid 5,8,11,14-eicosatetraenoic acid, 7,10,13,16-docosatetraenoic acid, 4,7,10,13,16-docosapentaenoic acid, 9,12,15-octadecatrienoic acid, 6,9,12,15 octadecatetraenoic acid, 8,11,14,17-eicosatetraenoic acid, 5,8,11,14,17-eicosapentaenoic acid, 7,10,13,16,19-docosapentaenoic acid, 4,7,10,13,16,19-docosahexaenoic acid, 5,8,11-eicosatrienoic acid, 9c11t3t-eleostearic acid, 8t10t12c-calendic acid, 9c11t13c-catalpic acid, 4,7,9,11,13,16,19-docosaheptadecanoic acid, taxoleic acid, pinolenic acid, sciadoic acid, 6-octadecinoic acid, t11-octadecen-9-inoic acid, 9-octadecinoic acid, 6-octadecen-9-inoic acid, t10-heptadecen-8-inoic acid, 9-octadecen-12-inoic acid, t7,t11-octadecadien-9-inoic acid, t8,t10-octadecadien-12-inoic acid, 5,8,11,14-eicosatetrainoic acid, retinoic acid, isopalmitic acid, pristanic acid, phytanic acid, 11,12-methylene octadecanoic acid, 9,10-methylene hexadecanoic acid, coronaric acid, (R, S) lipoic acid, (R) lipoic acid (S) lipoic acid, 6,8-(methylsulfanyl) octanoic acid, 4,6-bis-(methylsulfanyl)-hexanoic acid, 2,4-bis (methylsulfanyl) butanoic acid, 1,2-dithiolane carboxylic acid, (S)-6,8-dithian-octanoic acid, tariric acid, santalic acid, sterol acid, 6,9-octadeceninoic acid, pyrulic acid, crepenic acid, heisteric acid, t8, t10-octadecadiene-12-inoic acid, ETYA, cerebronic acid, hydroxynervic acid, ricinoleic acid, lesquerolic acid, brassylic acid, thapsic acid, phytic acid, sinapinic acid, cinnamic acid, trihydroxy acids, and phosphatidic acids.

Fatty Alcohols

Generally fatty alcohols are aliphatic carbon chains having a primary hydroxyl group. The carbon atoms may be linked with a single bond (saturated fatty acids) or with a double bond bridges (unsaturated fatty acids); these double bonds can be in a cis- or trans-configuration. In analogy to the definition of fatty acids, the term fatty alcohols refers to compounds having more than 5 consecutive carbon atoms in addition to the hydroxy group. Examples of linear saturated fatty alcohols are 1-hexanol, 1-heptanol, 1-octanol, 1-nonanol, 1-decanol, 1-undecanol, 1-dodecanol, 1-tridecaol, 1-tetradecanol, 1-pentadecaol, 1-hexadecanol, 1-heptadecanol, 1-octadecanol, 1-nonadecanol, 1-eicosanol, 1-heneicosanol, 1-docosanol, 1-tetracosanol, 1-octacosanol, 1-hentriacontaole, 1-triacontanol.

Examples for mono-olefinic fatty alcohols are cis-9-hexdecen-1-ol, cis-9-octadecene-1-ol, trans-9-octadecen-1-ol and cis-11-octadecen-1-ol. Examples of polyunsaturated fatty alcohols are all cis-9,12-octadecendien-1-ol, 5,8,11,14-eicosatetraen-1-ol.

Waxes

The term waxes refers to monoester (fatty acid ester) from a fatty acid or wax acid and a primary fatty- or wax-alcohol. Long chain carboxylic acids, starting with 22 carbon atoms, are also known as wax acids. The transitions between the fatty acids and wax acids are not clearly defined, but blurred. The long-chain primary alcohols consisting of 22 carbon atoms and more and are also called wax alcohols. Again, the transitions between the fatty alcohols and wax alcohols are not clearly defined, but blurred. Naturally occurring waxes are often mixtures. Naturally occurring wax is present as a mixture of fatty acids or wax acids, fatty alcohols and wax alcohols and a fatty acid ester.

Examples of vegetable waxes are candelilla wax, carnauba wax, Japan wax, esparto wax, cork wax, guaruma wax, rice germ oil wax, sugar cane wax, ouricury, and montan wax. Examples of animal waxes are beeswax, shellac wax, spermaceti, lanolin (wool wax), and uropygial fat. Examples of petrochemical waxes are petrolatum, paraffin waxes, and micro waxes.

Odorants and Tasting Agents

The terms "odorants" and "tasting agents", as used herein, are interchangeable with the term "flavouring agent". In virtually all organic mixtures of biogenic origin, organic compounds are present which lead to sensory perception in the sense of taste or an odor. There is an extremely large heterogeneity of organic compounds that possibly cause such a perception. Even among the strongly hydrophobic compounds that can be found in various lipid phases, the structural composition of the carbon-based compounds is not uniform. Some typical classes of such compounds are alkaloids, alcohols, aldehydes, amino acids, aromatic hydrocarbons, esters, lactones, cyclic ethers, furans, furanoids, free fatty acids, flavonols, glycosides, ketones, saturated and unsaturated hydrocarbons, enamine ketones, ketopiperazines, isoprenoids, mono-terpenes, terpenes, cyclic terpenes, triterpenes, triterpenoids, tetraterpenes, sesquiterpenes, sequesterpenoids, sterols, phytosterols, purine derivatives, phenylpropanoids, phenols and/or hydroxycinnamic acid derivatives. These classes of compounds may occur both individually and in any composition in a crude lipid phase derived from a biogenic raw material. These are in particular 1,5-octadien-3-ol, butanal, hexanal, octanal, nonenal, nonadineal, decanal, dodecanal, piperonal, cysteine, cystine, methionine, phenantrene, anthracene, pyrene, benzpyrene, 4-hydroxybutanoic acid, ethyl hexanoate, coumarin, maltol, diacetylfuran, pentylfuran, perylene, rosefuran, caprylic acid, capric acid, hydroxy fatty acids, amygdalin, progoitrin, 2-heptanone, 2-nonanone, decatrienal, 1-octen-3-on, vinylamyl ketone, 4-(4-hydroxyphenyl)-butan-2-one) mycosporine, diketopiperazine, humulones and lupulones (bitters acids), mono-terpenes: myrcene, ocimene and cosmen, linalool, myrcenol, ipsdienol, neral; citronellol and geranial, citronellal, myrcene, limonene, linalool, nerol, geraniol, terpinolene, terpine and p cymene, carvone and carvenon, thymol, dihydroxycarveol, 2 pinene, α- and β-pinene, limonene, phellandrene, menthane, camphor; fenchon, xanthophylline, bisabolane, germacrane, elemane and humulane, farnesene, rotundone, sterols, phytosterols, P-cresol, guaiacol, ferulic acid, lignin, sinapine, catechins, eugenol, vanillin, 3-butenylisothiocyanate, 4-petenylisothocyanate, 4-pentenenitrile, 5-hexenitrile, camphene, dodecane, cinnamyl alcohol, fenchyl alcohol, 1R, 2S, 5R-isopulegol, 2-ethyl fenchol, menthol, 2-(4-hydroxy-3,5-dimethoxybenzyl alcohol, (R)-(−)-Lavandulol, piperonyl alcohol, thujyl alcohol, 1,8-cineole, 4-ethyl guaiacol, —N-[[(1R,2S,5R)-5-methyl-2-(1-methylethyl)cyclohexyl]carbonyl]-glycine ethyl ester, (1R, 2S, 5R), N-cyclopropyl-5methyl-2-isopropylcyclohexanecarboxamide, L-alanine, aspartic acid, 2,4-dimethylthiazole, lenthionine, (+)-cedrol, 3-methylphenol, anisole, 1-methoxy-4-propylbenzene, 4-allyl 2,6-dimethoxyphenol, 2,6-dimethoxy-4-vinylphenol, ethyl-4-hydroxy-3-methoxybenzyl ether, vetiverol, 2-butylethyl ether, ethylgeranylether, carvacrole, 2-methylpropanal, cinnamaldehyde, p-toluenealdehyde, 2-methylbutyraldehyde, salicylaldehyde, acetic acid, lactic acid, 3-methylbutyric acid, hexanoic acid, 1-malic acid and/or anethole.

These compounds may occur both separately and in any composition in a raw lipid phase originating from a biogenic raw material.

Compounds Carrying Guanidino and/or Amidino Groups

A guanidino group (or guanidino group) is called the chemical residue H$_2$N—C(NH)—NH— and its cyclic forms and an amidino group (or amidine group) the chemical residue H$_2$N—C(NH)— (see examples below) and its cyclic forms. Preferred are guanidino compounds (herein referred as compound containing a guanidino group) which have in addition to the guanidino group at least one carboxylate group (COOH). It is also preferable that the carboxylate group(s) is/are separated from the guanidino group by at least one carbon atom within the molecule. Preferred are also amidino compounds (herein referred as compound containing a amidino group) which exhibit in addition to the amidino group at least one carboxylate group (COOH). It is also preferable if the carboxylate group(s) is/are separated by at least one carbon atom from the amidino group within the molecule.

This guanidino and amidino compounds preferably have a partition coefficient $K_{OW}$ between n-octanol and water of less than 6.3 ($K_{OW}$<6.3). Preferably, the $K_{OW}$ is <1.8 (log $K_{OW}$<0.26), more preferably <0.63 (log $K_{OW}$<-0.2), and most preferably <0.4 (log $K_{OW}$<-0.4).

Particularly preferred are arginine derivatives. Arginine derivatives are defined as compounds having a guanidino group and a carboxylate group or an amidino group and a carboxylate, wherein the carboxylate group and guanidino group or amidino group and carboxylate group are away from each other by at least one carbon atom, i.e., at least one of the following groups is between the guanidino or amidino group and the carboxylate group: —CH$_2$—, —CHR—, —CRR—, wherein R and R' independently of each other represent any chemical residues. Of course, the distance between the guanidino group and the carboxylate group or amidino group and the carboxylate group may also be more than one carbon atom, for example, due to the following groups —(CH$_2$)$_n$—, —(CHR)$_n$—, —(CRR')$_n$—, with n=2, 3, 4, 5, 6, 7, 8 or 9 as this is the case for example with amidino-propionic acid, amidino-butyric acid, guanidino-propionic acid or guanidino-butyric acid. Compounds with more than one guanidino and more than one carboxylate group are, for example, oligoarginine and polyarginine.

The following examples show preferred compounds having a guanidino or an amidino group and a carboxylate group.

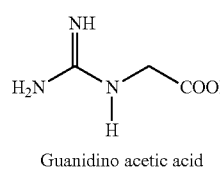
Guanidino acetic acid

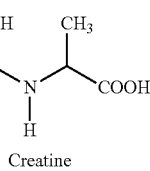
Creatine

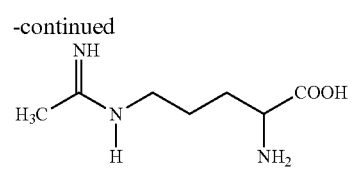
Glycocyamine

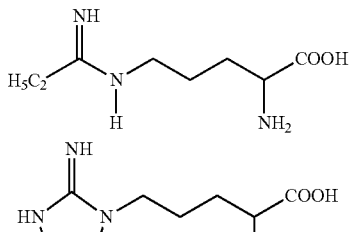

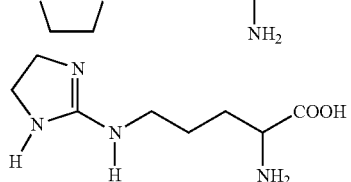

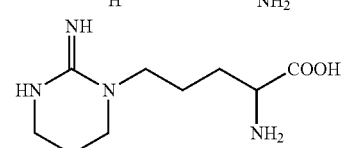

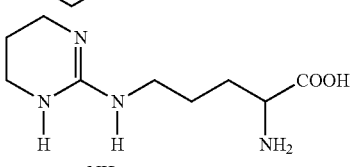

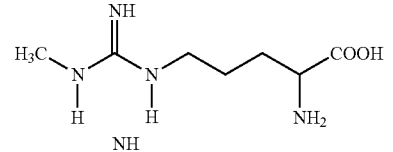

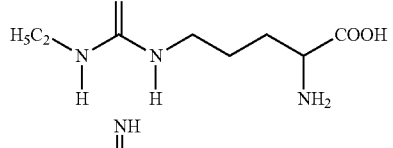

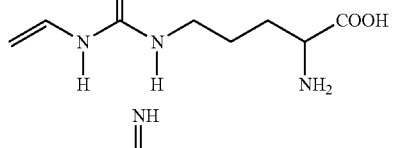

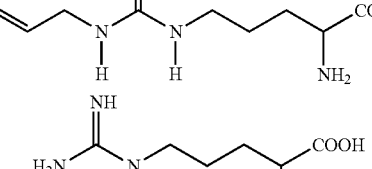

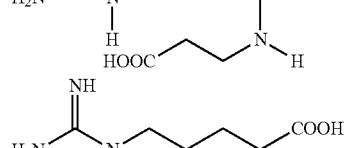

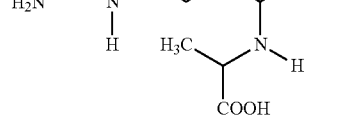

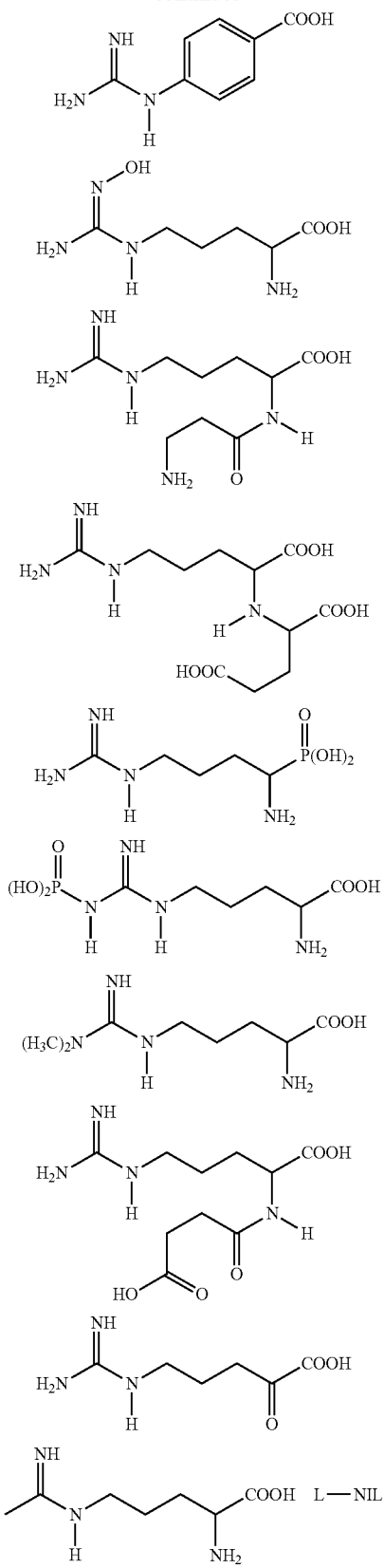

Preferred arginine derivatives are compounds of the following general formula (I) or (II)

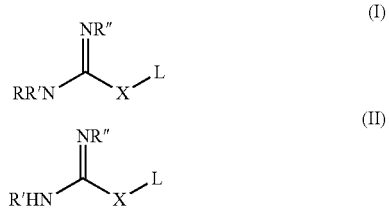

wherein
R', R", R'" and R"" mean independently from each other: —H, —OH, —CH=CH$_2$, —CH$_2$—CH=CH$_2$, —C(CH$_3$)=CH$_2$, —CH=CH—CH$_3$, —C$_2$H$_4$—CH=CH$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)s, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, cyclo-C$_3$H$_5$, cyclo-C$_4$H$_7$, cyclo-C$_5$H$_9$, cyclo-C$_6$H$_{11}$, —PO$_3$H$_2$, —PO$_3$H$^-$, —PO$_3$$^{2-}$, —NO$_2$, —C≡CH, —C≡C—CH$_3$, —CH$_2$—C≡CH, —C$_2$H$_4$—C≡CH, —CH$_2$—C≡C—CH$_3$, or R' and R" together create one of the groups: —CH$_2$—CH$_2$—, —CO—CH$_2$—, —CH$_2$—CO—, —CH=CH—, —CO—CH=CH—, —CH=CH—CO—, —CO—CH$_2$—CH$_2$—, —CH$_2$—CH$_2$—CO—, —CH$_2$—CO—CH$_2$— or —CH$_2$—CH$_2$—CH$_2$—;

X stands for —NH—, —NR""—, —O—, —S—, —CH$_2$—, —C$_2$H$_4$—, —OC$_3$H$_6$—, —C$_4$H$_8$— or —C$_5$H$_{10}$— or for one C1 to C5 carbon chains, which can be substituted by one or more residues: —F, —Cl, —OH, —OCH$_3$, —OC$_2$H$_5$, —NH$_2$, —NHCH$_3$, —NH(C$_2$H$_5$), —N(CH$_3$)$_2$, —N(C$_2$H$_5$)$_2$, —SH, —NO$_2$, —PO$_3$H$_2$, —PO$_3$H$^-$, —PO$_3$$^{2-}$, —CH$_3$, —C$_2$H$_5$, —CH=CH$_2$, —C≡CH, —COOH, —COOCH$_3$, —COOC$_2$H$_5$, —COCH$_3$, —COC$_2$H$_5$, —O—COCH$_3$, —O—COC$_2$H$_5$, —CN, —CF$_3$, —C$_2$F$_5$, —OCF$_3$, —OC$_2$F$_5$;

L represents a hydrophilic substituent, selected from a group consisting of: —NH$_2$, —OH, —PO$_3$H$_2$, —PO$_3$H$^-$, —PO$_3$$^{2-}$, —OPO$_3$H$_2$, —OPO$_3$H$^-$, —OPO$_3$$^{2-}$, —COOH, —COO$^-$, —CO—NH$_2$, —NH$_3$$^+$, —NH—CO—NH$_2$, —N(CH$_3$)$_3$$^+$, —N(C$_2$H$_5$)$_3$$^+$, —N(C$_3$H$_7$)$_3$$^+$, —NH(CH$_3$)$_2$$^+$, —NH(C$_2$H$_5$)$_2$$^+$, —NH(C$_3$H$_7$)$_2$+, —NHCH$_3$, —NHC$_2$H$_5$, —NHC$_3$H$_7$, —NH$_2$CH$_3$$^+$, —NH$_2$C$_2$H$_5$$^+$, —NH$_2$C$_3$H$_7$$^+$, —SO$_3$H, —SO$_3$$^-$, —SO$_2$NH$_2$, —CO—COOH, —O—CO—NH$_2$, —C(NH)—NH$_2$, —NH—C(NH)—NH$_2$, —NH—CS—NH$_2$, —NH—COOH,

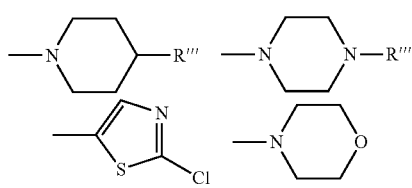

Plant Colour Pigments and Dyes
The term "dyes" summarizes all coloured or colour-giving organic compounds typically found in oils and fats of biogenic origin in varying quantities and compositions. The term "plant dyes" summarizes all coloured or colour-giving compounds that are included in lipid phases. The most dominant dye forms with by far the largest quantity that are present in vegetable oils is the group of chlorophylls and their degradation products, such as pheophyline, chlorophyllides, pheophorbides, phyropheophytine, chlorine, and rhodine purpurins. However, in addition, compounds that can be assigned to the group of carotenes or carotenoids occur. In addition, however, other classes of compounds do occur, such as the flavonoids, curcumines, anthrocyans, betaines, xanthophylls, which include carotenes and lutein, indigo, kaempferol and xantophylline, such as neoxanthin or zeaxanthin. These dyes may be present in different proportions in the lipid phase and exhibit different solubilities in water or organic solvents.

The most common representatives of plant pigments are chlorophylls. In vegetable oils chlorophylls are typically encountered in quantities between 10 and 100 ppm (or 100 mg/kg), respectively. Oils that typically have a high content of chlorophylls are particularly canola and rapeseed oils.

Chlorophylls

The term "chlorophylls", as described herein, summarizes compounds which consist of a derivatized porphyrin ring and are classified according to their organic residues in the subgroups a, b, c1, c2, and d. Furthermore, they differ in the number of double bonds between carbon atom 17 and 18.

Phospholipids

The term "phospholipids", as used herein, summarizes amphiphilic lipids which contain a phosphate group and can be assigned to the substance classes of phosphoglycerides or phosphosphingolipids. Further included are acidic glycoglycerolipids such as sulfoquinovosyldiacylglycerin or sulfoquinovosyldiacylglycerin. "Phosphoglycerides" (also referred to as glycerophospholipids or phosphoglycerolipids) consisting of a diacylglyceride, and its remaining terminal hydroxy group is attached to a phosphate residue, which is not further modified either (phosphatidic) or is esterified with an alcohol. The most common representatives of the latter group are phosphatidylcholine (also called lecithin), phosphatidylethanolamines, and phosphatidylserine. "Glycophosphatidylinositols" are compounds in which phosphatidylinositol is bound to the inositol group through a saccharideglycositol link.

Glycolipids

The term "glycolipid", as used herein, stands for compounds in which one or more monosaccharide residue(s) is/are connected via a glycosidic bond with a hydrophobic acyl group.

Glycoclycerolipids

The term "glycoglycerolipid" herein refers to both phosphoglycosphingolipids and phosphonoglycosphingolipids and glycosphingolipids, and further sulfoglycosphingolipids, sialoglycosphingolipids, and mono-, oligo-, and polyglycosylsphingoides and monomers, oligomers, and polyglycosylceramides. Further examples are rhamnolipids, sophorlipids, trehalose lipids, and lipopolysaccharides.

Fields of Application

Compounds carrying guanidino and/or amidino groups that are dissolved in water allow solubility of carboxylic acids in an aqueous medium and thereby enable their release from mixtures of organic material and transfer into the aqueous phase, forming aqueous emulsions and nano-emulsions that are provided in process step a). Thus, the inventive aggregation process is particularly suitable to aggregate and separate carboxylic acids present in such an aqueous emulsion and nano-emulsions consisting of carboxylic acids, and compounds carrying guanidino and/or amidino groups. This can be applied for cleaning procedures of lipid phases, in particular for oils and fats which contain unacceptable amounts of carboxylic acids. This also applies, in addition to oil phases of biogenic origin, to fossil lipid phases. If the carboxylic acids are complexed with other organic compounds, their liberalization is also possible, whereby through entry of water molecules, other organic compounds may also be dissolved. This phenomenon can be used to dissolve a variety of biogenic materials and mixtures. If there are no carboxylic acids present in the aggregates that can be nano-emulsified with the claimed compounds carrying guanidino and/or amidino groups, then solvation/decomplexation of the organic aggregates can also be achieved by an aqueous nano-emulsion consisting of carboxylic acids dissolved with compounds carrying guanidino and/or amidinogroups. In this way, the refining method is suitable for virtually all lipid phases, as described herein as well as for organic matter complexes.

The fields of applications from which the aqueous emulsions or nano-emulsions may originate are therefore particularly agricultural, biotechnological, or industrial processes, and procedures in which the cleaning and refining process by aqueous solutions with compounds carrying guanidino and/or amidino groups can be used, in order to transfer carboxylic acids and other organic compounds into an aqueous macro- or nano-emulsion. By the use of the inventive aggregation process, the separated carboxylic acids can be obtained in a purity of their substance class of >85%, more preferably of >95%, and most preferably of >98%. This concerns processes in the refining of vegetable oils or animal fats, process fluids in wood processing or biotechnological production of carboxylic acids, among others.

Further preferred are applications in processes in which aqueous emulsions and suspensions arise from decomplexation procedures, a purification method or an extraction method in which the aqueous solution contain compounds carrying guanidino and/or amidino groups with or without nano-emulsified carboxylic acids herein. Such applications relate, for example, to the digestion of biomass or processes in the food production or utilization, as well as in the processing of wastes, which contain organic compounds, or extractions of lipid phases or organic compounds from inorganic porous materials. It has been shown that for the provision of an aqueous emulsion according to process step a), it is irrelevant whether carboxylic acids are present in the organic compound mixture, so that the process step b) according to the invention can be carried out.

Examples of aqueous emulsions that may derive from these areas of application are, e.g., aqueous extractions of plant materials including biomasses, fermentation residues from biogas plants, condensates of fat deposition processes, for example, in slaughterhouses or in the fishing industry. Furthermore, purification of fruit seeds or skins, separating organic constituents of sewage sludge, decomplexation and release of lipid phases from rocks. Thereby, the separated organic compounds are obtainable and can be fractionated, purified, and used for the foods, animal feed, and cosmetic, pharmaceutical or chemical products. Furthermore is preferred to obtain flavouring substances besides other organic compounds from extractions by aqueous emulsion with compounds carrying guanidino and/or amidino groups, particularly from plant extraction processes. A variety of flavors can thus be obtained with purity for the substance group of at least 50%, more preferred >75%, and most preferred >90%. Examples of flavors are lemon, menthane, camphor, fenchone, xanthophyllines, bisabolanes, germacrene, elemanes and humulone, farnesene, rotundone, sterols, phytosterols, p-cresol, guaiacol, ferulic acid, lignin, sinapine, catechins, eugenol, vanillin, and anetholes.

The preferred organic compounds which can be obtained with the process according to the invention include organic dyes. Therefore, a preferred field of application is the aqueous extraction of plant extracts which were obtained by an aqueous extraction with one of the methods described herein, e.g. a nanoemulsive aqueous extraction, and which is aggregated and separated by means of the inventive method. Preferred is the extraction of plant dyes from the group of chlorophylls and carotenes. By using appropriate techniques purity of obtainable substance groups is >50%, more preferred >75%, and most preferred >90%.

Further, a preferred field of application is the extraction and recovery of fat-soluble vitamins, phytosterols, odorants, tasting agents, flavours, and dyes. These can be prepared by the previously described methods from the organic mixtures by appropriate techniques in purity for their substance groups of >50%, more preferred >75%, and most preferred >90%.

Further preferred fields of application are the extraction and recovery of polyphenols, squalene, lignins, limonene, phellandren, menthane, camphor, fenchone, xanthophyllines, bisabolanes, elemanes and humulone, farnesene, rotundon, sterols, phytosterols, p-cresol, guaiacol, ferulic acid, lignin, sinapine, catechins, eugenol, vanillin, and anethole. These can be prepared by the previously described method from the organic mixtures by appropriate techniques in purity for their substance class >50%, more preferred >75%, and most preferred >90%.

Also preferred is the separation and purification of peptides and proteins, such as albumins and globulins. They can be obtained by appropriate techniques with in purity of their substance class >50%, more preferred >75%, and most preferred >90%.

Particularly preferred is the separation and purification of so-called mucilage, particularly preferably among those are phospholipids, especially phosphotidylcholine and phosphoinositole and glycolipids and glyceroglycolipids. They can be obtained by appropriate techniques in purity of their substance class >50%, more preferred >75%, and most preferred >90%.

The inventive method for aggregation of organic compounds is particularly suitable to permit reusability of solutions with compounds carrying guanidino and/or amidino groups and the receipt of a clarified and/or purified aqueous phase that can be used for a cleaning or decomplexation process.

Use of Organic Aggregates

Possible uses of the separated organic compounds depend on both the starting material and the purity of receivable compound classes that are obtained. In principle, all classes of compounds, such as carboxylic acids, phospholipids, glycolipids, glyceroglycolipids, dyes, phenols, sinapines, squalenes, vitamins, phytosterols, amino acids, peptides, proteins, carbohydrates, lipoproteins, waxes, fatty alcohols and flavors, can be fractionated by appropriate selection of solvents.

Particularly advantageous is that the separated fraction of chlorophylls from organic compounds obtained by aggregation initiation with copper ions exhibit an intense green colour, which hardly discoloured even when the separated fraction was allowed to stand for months. Therefore, the use of chlorophylls which are chemically and structurally unaltered and recovered from a separation of an organic substance mixture, which is obtained through the inventive aggregation with copper ions, is preferred. Also particularly preferred is the receipt and use of a very pure phospholipid fraction, since these can be separated from the carboxylic acids by simple means. These phospholipids are not or only to a minor extent hydrolyzed, when they are fractionated under appropriate conditions (e.g., rapid sample processing/cooling/drying). Thus, preferred is the use of a pure phospholipid fraction that has a purity of preferably >90%, more preferably >95%, and most preferably >98%, while there is no or almost no hydrolysis present of this compound class. Further preferred is the receipt and use of chemically unaltered carboxylic acids. They are obtainable with a purity of the compound class of preferably >90%, more preferably >95%, and most preferably >98% by an appropriate solvent. Further, preferred is the extraction and use of proteins and amino acids, which can be fractionated at a purity of this substance group of preferably >70%, more preferably >85%, and most preferably >90%. Further preferred is the receipt and use of glycerosteroles, calciferol (vitamin D2), cholecalciferol (vitamin D3), and other sterol compounds.

Of particular interest are also fat-soluble vitamins and phenols which can be separated from purifications of plant extracts. With a fractionation, as described herein, a purity of this substance group can be obtained of preferably >70%, more preferably >85%, and most preferably of >90%.

Also preferred is the extraction of flavoring substances which are contained in the complexed organic compounds by fractionation, as described herein, that have a purity of this substance group of preferably >70%, more preferably >85%, and most preferably of >90%.

The obtainable organic compounds may find use in the food or feed industry, in hygiene and cosmetics products, flavoring preparations, such as seasonings, food additives, essential oils, in pharmacological or pharmaceutical preparations or in the chemical industry, as well as for the production of biopolymers.

Furthermore, the invention relates to a process for the aggregation and separation of a mixture of organic substances, which are present in an aqueous emulsion in dissolved form, characterized by the steps of:

a) providing an aqueous emulsion or nano-emulsion containing dissolved organic compounds, whereby the organic compounds are selected from carboxylic acids, phospholipids, glycolipids, glyceroglycolipids, phenols, sterols, chlorophylls and/or sinapines, and wherein the aqueous emulsion according to step a) comprises at least a compounds carrying guanidino and/or amidino groups with a $K_{ow}$<6.3.

b) mixing the emulsion of step a) with an aqueous solution containing copper(II) ions and/or calcium ions, until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide, and/or zinc oxide and/or adding to the emulsion of step a) calcium oxide, magnesium oxide and/or zinc oxide in solid form until aggregate formation.

In addition, the invention relates to a process for the aggregation and separation of an organic substance mixture, which is present in an aqueous emulsion in dissolved form, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion originates from a refining process of a lipid phase.

b) mixing the emulsion of step a) with an aqueous solution containing copper(II) ions and/or calcium ions until aggregate formation,
c) separating the aggregates from step b) by sedimentation, filtration, or centrifugation after obtaining an aggregated phase of organic compounds from step b).

Step b) of the procedure stated above may alternatively be as follows:
b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form with mixing until aggregate formation.

Thus, the invention also relates to a process for the aggregation and separation of a mixture of organic substances, which are dissolved in an aqueous emulsion, characterized by the steps of:
a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) contains at least one compound containing guanidino and/or amidino groups with a $K_{ow}$ of <6.3 and derives from a refining process of a lipid phase.
b) mixing the emulsion of step a) with an aqueous solution containing copper(II) ions and/or calcium ions until aggregate formation,
c) separating the aggregates from step b) by sedimentation, filtration, or centrifugation after obtaining an aggregated phase of organic compounds from step b).

Step b) of the procedure stated above may alternatively be as follows:
b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) with calcium oxide, magnesium oxide and/or zinc oxide in solid form with mixing until aggregate formation.

Furthermore, the invention relates to a process for the aggregation and separation of a mixture of organic substances, which are dissolved in an aqueous emulsion, characterized by the steps of:
a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) at least one compound containing guanidino and/or amidino groups with a $K_{ow}$ of <6.3.
b) mixing the emulsion of step a) with an aqueous solution containing copper(II) ions and/or calcium ions at most at 75° C. until aggregate formation,
c) separating the aggregates from step b) by sedimentation, filtration, or centrifugation after obtaining an aggregated phase of organic compounds from step b).

Step b) the method above may alternatively be as follows:
b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form at most at 75° C. until aggregate formation.

In addition, the invention relates to a process for the aggregation and separation of a mixture of organic substances, which are dissolved in an aqueous emulsion, characterized by the steps of:
a) providing an aqueous emulsion having present dissolved organic compounds, where the organic compounds are carboxylic acids, phospholipids, glycolipids, glyceroglycolipids, phenols, sterols, chlorophylls and/or sinapines, and wherein the aqueous emulsion derives from the refining process of a lipid phase.
b) mixing the emulsion of step a) with an aqueous solution containing copper(II) ions and/or calcium ions at most at 75° C. until aggregate formation,
c) separating the aggregates from step b) by sedimentation, filtration, or centrifugation after obtaining an aggregated phase of organic compounds from step b).

Step b) of the procedure stated above may alternatively be as follows:
b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form at most at 75° C. until aggregate formation.

Thus, the invention also relates to a process for the aggregation and separation of a mixture of organic substances, which are dissolved in an aqueous emulsion, characterized by the steps of:
a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) at least one compound containing guanidino and/or amidino groups with a $K_{ow}$ of <6.3 and derives from the refining process of a lipid phase.
b) mixing the emulsion of step a) with an aqueous solution containing copper(II) ions and/or calcium ions at most at 75° C. until aggregate formation,
c) separating the aggregates from step b) by sedimentation, filtration, or centrifugation after obtaining an aggregated phase of organic compounds from step b).

Step b) of the procedure stated above may alternatively be as follows
b) mixing the emulsion of step a) with an aqueous solution containing copper(III) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form at most at 75° C. until aggregate formation.

Furthermore, the invention relates to a process for the aggregation and separation of a mixture of organic substances which are dissolved in an aqueous emulsion, characterized by the steps of:
a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) contains at least one compound containing guanidino and/or amidino groups with a $K_{ow}$<6.3.
b) mixing the emulsion of step a) with an aqueous solution containing copper(II) ions and/or calcium ions with a laminar stirrer until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form by mixing with a laminar stirrer until aggregate formation.

In addition, the invention relates to a process for the aggregation and separation of a mixture of organic substances, which are dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion derives from a refining process of the lipid phase.

b) mixing the emulsion of step a) with an aqueous solution containing copper(II) ions and/or calcium ions with a laminar stirrer until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form and mixing with a laminar stirrer until aggregate formation.

Thus, the invention also relates to a process for the aggregation and separation of a mixture of organic substances, which is dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) contains at least one compound containing guanidino and/or amidino groups with a $K_{ow}$<6.3 and derives from a refining process of a lipid phase.

b) mixing the emulsion of step a) with an aqueous solution containing copper(II) ions and/or calcium ions with a laminar stirrer until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form and mixing with a laminar stirrer until aggregate formation.

Furthermore, the invention relates to a process for the aggregation and separation of an organic substance mixture, which is dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) contains at least one compound containing guanidino and/or amidino groups with a $K_{ow}$<6.3.

b) mixing the emulsion of step a) with an aqueous solution containing copper(II) ions and/or calcium ions with a laminar stirrer at a maximum temperature of 75° C. until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form and mixing with a laminar stirrer at a maximum temperature of 75° C. until aggregate formation.

In addition, the invention relates to a process for the aggregation and separation of a mixture of organic substances, which are dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion derive from a refining process of the lipid phase.

b) mixing the emulsion of step a) with an aqueous solution containing copper(II) ions and/or calcium ions with a laminar stirrer at a maximum temperature of 75° C. until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form and mixing to with a laminar stirrer at a maximum temperature of 75° C. until aggregate formation.

Thus, the invention also relates to a process for the aggregation and separation of a mixture of organic substances, which are dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, and wherein the aqueous emulsion according to step a) contains at least one compound containing guanidino and/or amidino groups with a $K_{ow}$<6.3 and derives from a refining process of a lipid phase.

b) mixing the emulsion of step a) with an aqueous solution containing copper(II) ions and/or calcium ions with a laminar stirrer at a maximum temperature of 75° C. until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) with an aqueous solution containing copper(II) ions and/or calcium ions and/or with an aqueous dispersion comprising calcium oxide, magnesium oxide and/or zinc oxide and/or adding to the emulsion of step a) calcium oxide, magnesium oxide and/or zinc oxide in solid form and mixing with a laminar stirrer at a maximum temperature of 75° C. until an aggregate formation.

Furthermore, the invention relates to a process for the aggregation and separation of a mixture of organic substance, which are dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines.

b) mixing the emulsion of step a) with an aqueous solution containing copper(II) ions until aggregate formation, c) separating the aggregates from step b) by sedimentation, filtration or centrifugation after obtaining an aggregated phase of organic compounds from step b).

d) separating said copper(II) ions from the aqueous solution.

Step b) of the procedure stated above may alternatively be as follows:

b) mixing the emulsion of step a) with an aqueous solution containing copper(II) ions and/or with an aqueous dispersion containing magnesium oxide and/or zinc oxide and/or adding to the emulsion from stage a) magnesium oxide and/or zinc oxide in solid form and mixing until aggregate formation.

Furthermore, the invention relates to a process for the aggregation and separation of a mixture of organic substances, which are dissolved in an aqueous emulsion, characterized by the steps of:

a) providing an aqueous emulsion having dissolved organic compounds, where the organic compounds are selected from carboxylic acids, phospholipids, glycolipids, glyceroglycolipids, phenols, sterols, chlorophylls and/or sinapines, b) mixing the emulsion of step a) under discontinuous addition with an aqueous solution containing copper(II) ions and/or calcium ions until aggregate formation, c) separating the aggregates from step b) by sedimentation, filtration, or centrifugation after obtaining an aggregated phase of organic compounds from step b).

Step b) of the procedure stated above may alternatively be as follows:

b) mixing the emulsion of step a) under discontinuous addition of an aqueous solution containing copper(II) ions and/or calcium ions and/or discontinuous addition with an aqueous dispersion comprising calcium oxide, magnesium oxide and/or zinc oxide and/or adding to the emulsion from step a) under discontinuous addition of calcium oxide, magnesium oxide and/or zinc oxide in solid form with mixing until aggregate formation.

EXAMPLES

Measurement Methods

The following test methods were used in the embodiments described below: Determination of the content of phosphorus, sodium, potassium, calcium, and iron in oil was carried out by means of ICP-OES (iCAP 7400, Thermo-Fisher Scientific, Germany).

The determination of the chlorophyll concentrations was performed, unless otherwise stated, on oil samples poured into 10 mm cuvettes without further dilution, by a UV-visible spectrometer (UV-1601, Shimadzu, Japan) at 630, 670, and 710 nm. The calculation of the chlorophyll pigment content was performed according to the AOCS method Cc formula of 13e-92.

The proportion of free fatty acids in the lipid phase was determined by methanolic KOH titration. Values are given in weight % (g/100 g).

The pH was determined with a glass capillary electrode (Blue Line, ProLab 2000, SI Analytics, Germany).

The concentration of benzo-a-pyrene was performed according to DGF method III 17a.

Determinations of droplet or particle sizes were done by a non-invasive laser light backscatter analysis (DLS) (Zetasizer Nano S, Malvern, UK). To this end, 2 ml of a liquid to be analyzed were poured into a measuring cuvette and placed in the measuring cell. Detection and quantification of particles or phase boundaries forming droplets runs automatically. The measuring range was between 10 μm and 0.3 nm.

The determination of turbidity of the water phases was carried out by a visual inspection. This was done by means of transparent cuvettes that had a depth of 3 mm, which were filled with the liquid to be tested. Judgment of turbidity was performed by two investigators, by viewing of image-lines through the cuvette, under standardized lighting conditions. In the presence of a distortion-free detection of the lines, the water phase was judged as transparent. The aqueous solution were judged to be slightly hazy if the view through a cuvette was not clear and there was apparent distortion of the sharpness of the line contours with reduced recognizability of image lines. A moderate turbidity was present if the visual appearance was cloudy and image-lines were still recognizable, but without sharp boundaries. Fluids were judged to be highly turbid if they were visually turbid and image-lines were no more recognizable. A fluid was classified as "milky" if the visual appearance was equal to that of milk.

Quantification of the turbidity (turbidimetry) of the water phases (aqueous emulsions) was determined by means of scattered light detection in which the re-entry of a scattered beam at 90° was detected by a measuring probe, which was immersed in a sample volume of 10 ml (InPro 8200-measuring sensor, M800 −1 transmitter, Mettler Toledo, Germany). The measuring range was 5-4,000 FTU. Each measurement was done in duplicate.

A comparison of turbidimetry measurements with the turbidity assessed by visual inspection which was carried out in parallel showed that in water phases judged to be transparent (turbidity score (TS)=1) values of the turbidimetry measurements were <10 FTU, if they were slightly hazy (TS=2) FTU values amounted 11-75, and in presence of a moderate turbidity (TS=3) FTU values ranged from 76 to 300, in highly turbid fluids (TS=4) FTU values were between 301 and 2,000 and in milky emulsions (TS=5) FTU values >2,000 were measured.

All tests were performed at atmospheric pressure (101.3 Pa) and at room temperature (25° C.), unless otherwise specified.

All solutions containing compounds carrying guanidino and/or amidino groups were dissolved in a low-ion or ion-free water phase.

All inventive ionizable compounds were completely dissolved in a low-ion water.

Example 1

Rice bran oil was subjected to a prepurification procedure I. degumming with phosphoric acid (85 wt %, volume addition 0.4 vol %, temperature 38° C., exposure time 30 minutes; II. sodium carbonate (15 wt %, volume addition 3 vol %, temperature 38° C.). Phase separations were carried out by means of a separator (OSD 1000, MKR, Germany, at a throughput of 100 l/h and a centrifugal force of 10,000×g). The separated oil was moderately turbid and examined for the oil key values: phosphorus content 14.1 ppm (or 14.1 mg/kg), calcium 28 ppm (or 28 mg/kg), iron 3.5 ppm (or 3.5 mg/kg), free fatty acids 1.2 wt % (g/100 g). Aqueous refinement of 200 liters of the oil was performed with an arginine solution (0.5 mol/l, volume addition 3 vol %) which was admixed with a propeller mixer at 35° C. for 20 minutes. The resulting emulsion had a milky appearance. Thereafter phase separation was performed as described above with the separator. Then the oil phase was almost clear and exhibited the following oil key values (determination methods are described in the section measurement methods): phosphorus content 2.1 ppm (or 2.1 mg/kg), calcium 0.05 ppm (or 0.05 mg/kg), iron 0.02 ppm (or 0.5 mg/kg), free fatty acids 0.15 wt %. The separated water phase was highly turbid and had a whitish-yellow colour, the pH was 12.5. The aqueous emulsion had an unpleasant and pungent plant odor. A 50 ml sample of the aqueous emulsion was filtered with a membrane filter having a nominal exclusion size of 0.45 μm. A microscopic analysis of filter paper showed no visible residues. To each of 100 ml samples of the aqueous emulsion the following solutions were added dropwise, while continuously mixing the solution with a magnetic stirrer (200 rpm). The aqueous solutions contained the following compounds (concentration 3 mol/l or as indicated) in dissolved form: HCl (25 wt %), iron (III) chloride (2.4 mol/l), copper(II) chloride (3.1 mol/l), copper(II) acetate, copper(II) sulfate, copper(II) citrate, calcium chloride, magnesium chloride, aluminium trichloride (2.8 mol/l), potassium chloride (3.8 mol/l) and sodium chloride (2 mol/l). Stirring was stopped every 30 seconds for 10 seconds. As soon as easily recognizable solid particles and a free water phase could be observed in the quiescent solutions, the addition of the aqueous solutions and stirring were terminated. Otherwise, the end of the test was reached when the volume addition exceeded 10 vol %. The suspensions were then allowed to stand for 10 minutes. Thereafter, phase separation was carried out using a beaker centrifuge (3,800 rpm for 5 minutes). Then the water phase and a solid phase were separated from each other by removing the water phase. The water phases were analyzed regarding turbidity (visual inspection and turbidimetry (see measurement methods)), the presence of particulate matter (visual inspection) and pH. Further, the volume of the solid phase was determined after decanting the residual liquid.

In further experiments, to each of a 100 ml sample of the aqueous emulsion powdery calcium oxide, magnesium oxide, zinc oxide, copper oxide, and titanium oxide was added in portions of 3 g that were added every 10 minutes. The solutions were mixed continuously using a magnetic stirrer (200 rpm). Once particles and a clear water phase were visible in the solution, stirring and the dosing were stopped. The suspensions were allowed to stand for 60 minutes and then phase separation was performed as described above.

The individual tests were repeated three times and the average amount of addition was calculated. The volumes of the resulting solid phases were determined and the relative ratio to the total volume of starting solution was calculated. The solid phases were subjected to vacuum drying at 60° C. for 12 hours and weighed thereafter [mass of solids 1]. In each approach, the water phase obtained after centrifugation of the aggregates that was clarified or still contained organic matter were mixed with 5 ml of a 25 vol % HCl solution in each (acid test). Then phase separation was performed by centrifugation, as described above, and pH of the free water phase was determined. The aqueous supernatants were decanted off and the solid phases vacuum dried, as described above, then the solid phases were weighed (values are given in Table 1 [mass of solids 2], acid test is considered negative if no solids were present). The obtained solid phases from aggregation with copper and calcium chloride solutions were subjected to decomplexation procedures using solvents. This involved sequential extractions with mixtures or extraction sequences with chloroform/methanol KOH, chloroform-HCl/butanol, chloroform/ethyl acetate, among others. From a fractionalized chloroform phase, gas chromatography was performed after methylation.

Results (Numerical Values are Summarized in Table 1):

Acid treatment resulted in rapid clarification of the water phase at pH values <3.0 which was complete after further addition of acid; the resulting aqueous phase then had a yellowish colour. Meanwhile there was solid formation which had a strong yellow colour and a rubbery-pasty and sticky consistency. The pH present at the moment of full clarification was 2.5. Addition of a sodium or potassium salt solution did not initiate aggregation of organic compounds up to the maximum volume ratio used (10 vol %). Addition of copper(II) chloride already initiated aggregation after a few drops. The addition was stopped after consumption of 0.007 mole of copper(II) chloride. Aggregation of the previously dissolved organic compounds developed henceforth completely. This resulted in a light blue, clear water phase. The solids collected by centrifugation consisted of a compact little crumbly mass with a green-blue colour.

Other solutions with copper(II) ions initiated aggregation in a similar manner, which also continued to completion after stopping further addition of copper ions. Addition of calcium ions to the aqueous emulsions resulted in a comparable initialization of aggregation; however, a greater amount of calcium ions was necessary to achieve a similar effect than was the case with copper ions and a slight turbidity and suspended solids remained in the water phase after complete aggregation. Further, the volume of the aggregate phase was larger than that of the aggregate phase achieved by copper ions. The same was true for the addition of iron (III) ions. By contrast, iron (II) ions as well as magnesium or aluminium ions exhibited a significantly lower effect on initializing aggregation and caused only a moderate separation efficacy in the case of $Mg^{2+}$ and $Al^{3+}$ or incomplete separation when using $Fe^{3+}$. Aggregation was initiated by addition of powdered calcium oxide, magnesium oxide, and zinc oxide. However, the aggregation initiation proceeded much slower than was the case with the addition of ionic copper(II) or calcium (II) ions. Recognizability of the initiation of aggregation was more difficult due to a haze that was caused by the oxide compounds. With the use of the above-mentioned oxides, complete separation of the organic compounds could be achieved; the solid phases, however, were more voluminous than aggregation phases obtained by aggregation with copper ions. Other oxides such as iron (II) and iron (III) oxide, CuO, and titanium oxide had no effect on aggregation initialization.

Separate samples (5 g) of the aggregate phases which had been obtained by aggregation initiation with copper chloride and copper sulfate were weighed and then subjected to vacuum drying at 60° C. for 12 hours and then reweighed again. The content of removable water was 5 wt % for both as calculated by the weight difference. The dried organic aggregate masses, which were pasty and highly viscos, but non-adhesive, were individually completely dissolvable in 50 ml of chloroform. In one approach, 15 ml of a solution consisting of methanol and water (95:5 v:v) was added to the solvent phases and mixed by shaking vigorously. This was followed by phase separation by centrifugation (4,000 rpm/ 10 minutes). The methanol layer was separated. Thin layer chromatography, performed on each sample of the methanol phases exhibited intense and well-defined bandings that could be assigned to phosphatidylcholine and phosphatidylinositol by comparison with a standard of phospholipids. There were practically no further adsorption bands recognizable. The chloroform phases were washed twice with an ethanol/water mixture (1:1 v:v), then separated by centrifugal phase separation. HCl (0.2 mmol) was added to the chloroform phases and mixed. Then 5 ml $H_2O$ was added. After centrifugation, the aqueous phase was separated. After a further washing step with water, a sample for an analysis by gas chromatography was taken. Herein, the fatty acids octanoic acid, dodecanoic acid, hexadecanoic acid, octadecanoic acid, oleic acid, and linoleic acid were detected. Further, ferulic acid and phytic acid were detectable. In another fractionation, a high concentration of tocopherol was found by RP-HPLC in an isooctane solvent fraction. In a further fractionation beta-sitosterol, which was solved in an ethanol phase, was detected by LC-GC.

The cation exchange resins Chelite P and Dowex 50WX4 (Serva, Germany) were added to samples of the free water phase (10 ml) which had been obtained after aggregation using $CuCl_2$ and $CuSO_4$, in an amount having a cation ion exchange capacity of >1 EQ/l. Applying gentle agitation, the colour of the solutions changed from light blue to a bright yellow. The exchange resins had an intense blue colour then. The pH of the supernatants (purified water phase) were identical to the pH of the starting solutions. The purified solutions were practically odorless. After separating the cation exchange resins, the pH of the solutions was adjusted to 1 by adding HCl; no precipitation was observed. There were also no measurable amounts of precipitated organic compounds in other clarified water phases, which were obtained from a successful aggregation of organic compounds, after adjusting the pH of the cleared water phases to <1.0. By contrast, organic compounds could be precipitated when the water phases were still turbid or consisted of an emulsion, by addition of an acid. This result had a close relationship with the visual appearance and the turbidity score present in the water phase obtained after the aggregation procedure.

TABLE 1

| Aggregation compound | Volume added (Vol %) | Turbidity (FTU) | Suspended matter | pH value | Volume of solids (Vol %) | Mass of solids 1 (g) | Mass of solids 2 (g) |
|---|---|---|---|---|---|---|---|
| $CuCl_2$ | 2.1 | 3 | 0 | 12.1 | 21 | 18.2 | 0 |
| $Cu(O_2CCH_3)_2$ | 2.8 | 5 | 0 | 11.3 | 23 | 18.4 | 0 |
| $CuSO_4$ | 2.6 | 4 | 0 | 11.9 | 21 | 18.3 | 0 |
| Cu citrate | 3.1 | 7 | 0 | 11.5 | 25 | 17.9 | 0 |
| $CaCl_2$ | 3.6 | 26 | 1 | 12.1 | 36 | 17.1 | 0.5 |
| $MgCl_2$ | 6.5 | 152 | 2 | 12.3 | 46 | 8.4 | 9.6 |
| $Fe(III)Cl_2$ | 5.2 | 97 | 1 | 13.1 | 29 | 9.4 | 8.6 |
| $Fe(II)Cl_3$ | >10 | 3122 | n.a. | 12.6 | 12 | 2.1 | 17.3 |
| $AlCl_3$ | 7.2 | 2544 | 2 | 11.8 | 42 | 12.5 | 7.4 |
| NaCl | >10 | 3623 | n.a. | 12.3 | n.a. | n.a. | 18.3 |
| KCl | >10 | 3177 | n.a. | 12.5 | n.a. | n.a. | 17.9 |
| HCl (25 Vol %) | 2.5 | 5 | 0 | 1.8 | 15 | 18.1 | 0 |
| CaO | 4.5 wt % | 814 | 1 | 13.2 | 45 | 22.4 | 0.4 |
| MgO | 5.8 wt % | 18 | 1 | 12.9 | 38 | 23.1 | 1.2 |
| ZnO | 7.6 wt-% | 22 | 1 | 13 | 31 | 23.8 | 1.8 |
| CuO | >10 wt % | 3256 | n.a. | 12.1 | n.a. | *) | 18.3 |
| $TiO_2$ | >10 wt % | 3644 | n.a. | 12 | n.a. | *) | 18.0 |
| $Al_2O_3$ | >10 wt % | 4122 | n.a. | 11.7 | n.a | *) | 17.8 |

Suspended matter: 0 = no, 1 = occasional, 2 = much;
n.a. = not assessable because of turbidity.
Mass of solids 1: solids in g, obtained by aggregation of the aqueous emulsion, centrifugation and drying;
Solid amount 2: solid in g, obtained from the cleared water/emulsion phase after the initial aggregation procedure and after HCl addition, phase separation and drying;
*) = The separated solid phase contained no detectable organic compounds and corresponded to the oxide used.

Example 2

Wet and oily sewage sludge (400 g) was mixed with 1000 ml of a solution mixture consisting of a nano-emulsion, which was generated by an aqueous solution containing arginine (50 mmol/l) and caproic acid (10 mmol/l), and a mixture of glycoglycerolipids (100 mg/l) which were vigorously stirred together. A 2-fold volume excess of the solution mixture was necessary to obtain a liquid suspension of the sludge. The suspension was stirred for 60 minutes at 40° C. This was followed by sedimentation over 2 hours. The supernatant (aqueous emulsion) was decanted into a separate vessel. The sediment was rinsed in a sieve and air-dried thereafter. The weight of the cleaned sediment was determined. The aqueous emulsion containing organic compounds had a deep black-brown colour and was very opaque. The pH was 11.6. In a series of otherwise identical procedures 0.5 ml of the following compounds: copper(II) chloride, copper(II) sulfate, copper(II) acetate, calcium chloride, iron (III) chloride, sodium hydroxide (in each 2 molar) and hydrochloric acid (10 wt %) or 1 gram powdered oxides of calcium and magnesium, respectively, were admixed to each 100 ml of the aqueous emulsion. The addition was repeated every 10 seconds until aggregate formation. The reaction mixture was continuous stirring (100 rpm) by using a mixer which consisted of a shaft on which several discs were aligned in parallel, thereby granting laminar shear forces. The emulsions were observed in order to detect aggregation herein. With the detection of aggregate formation and simultaneous appearance of a clear liquid phase, dosing and stirring were terminated. In those investigations where ionic compounds had been added, samples were centrifuged after 5 minutes of standing (4,000 rpm/10 minutes). Samples from investigations with oxide compounds were allowed to rest for 60 minutes, then centrifuged. The liquid supernatants were decanted after centrifugation and the turbidity of the cleared water phases was determined by visual judgment and turbidimetry. The volume of the separated solids was determined and the residual water content was evaluated according to example 1 by vacuum drying, then the dried solid masses were weighed. The dry weights are given in table 2. Aggregates of the untreated savage sludge were reduced to small particles and examined by light microscopy as well as the cleaned and dried sediment obtained after treatment with the solution mixture, in order to determine the composition and surface characteristics of the particles. An acid test was performed in all clarified water phases (experimental procedure described in Example 1).

between the original sewage sludge and the cleaned particles that had been recovered. The dry weight of the aggregate phases obtained after aggregation initiation with oxides was greater than that of the aggregate phases obtained by procedures with ionic compounds. The calculated amount of entrained and discharged water was less than 5% by weight in solid phases that are obtained by adding copper ions. The water content of the solid phase obtained after aggregation initiation with calcium or magnesium oxide-induced aggregation was slightly larger. Sodium hydroxide did not initiate aggregation of organic compounds.

The dried solid phases could be dissolved in a mixture of dichloromethane and methanol. The methanol phase could be separated by centrifugal phase separation (4,000 rpm/10 minutes). A sample of the methanol phase was used for thin layer chromatography. By this means, the presence of phospholipids could be demonstrated (experimental procedure as done in example 1).

Example 3

Fruit seeds may have adherent pulp residues; thus, in order to use the seeds for further processing, it can be beneficial to remove adhering material first. This applies in particular to avocado seeds. Residues, which are already dried, cannot be removed with water at room temperature, since they do not dissolve due to the high content of

TABLE 2

| Aggregation compound | Volume added (Vol %) | Turbidity (vis) | Turbidity (FTU) | Suspended matter | pH | Volume of solids (Vol %) | Mass of solids 1 (g) | Water content-SM |
|---|---|---|---|---|---|---|---|---|
| $CuCl_2$ | 4.6 | 0 | 3 | 0 | 11.1 | 38 | 37.5 | 4.5 |
| $Cu(O_2CCH_3)_2$ | 4.9 | 0 | 4 | 0 | 10.9 | 39 | 37.7 | 4.6 |
| $CuSO_4$ | 5 | 0 | 3 | 0 | 11 | 340 | 37.1 | 5.0 |
| $CaCl_2$ | 7 | 0 | 10 | 1 | 11.3 | 40 | 36.9 | 7.2 |
| $Fe(III)Cl_3$ | 3.6 | 1 | 52 | 1 | 11.4 | 42 | 33.1 | 9.3 |
| HCl | 6.2 | 0 | 1 | 0 | 2.1 | 36 | 37.2 | 3.3 |
| NaOH | >10 | 3 | 3,544 | n.a. | 14 | n.a. | n.a. | n.a. |

Turbidity (vis): visual assessment, where 0 = transparent, 1 = slightly, 2 = moderately, 3 = highly turbid;
Turbidity = FTU value from turbidimetry;
Suspended matter: 0 = no, 1 = occasional, 2 = much;
n.a. = not assessable because of turbidity;
Volume of solids = volume of the solid phase after centrifugation and decanting the aqueous phase in relation to the sample volume;
Mass of solids 1 = weight of the solid phase after vacuum drying;
Water content SM = Relative residual amount of water as calculated from the weight before and after drying.

Results:

Large amounts of soluble constituents could be extracted from the examined sewage sludge by the solution mixture used, generating a dark-coloured aqueous emulsion. Particles of the sludge initially had a fibrous appearance as shown in light microscopically; only occasionally surfaces were visible, which were identified as sand or quartz. However, sediments obtained after treatment with the aqueous solution mixtures consisted almost exclusively of sand- and quartz-like structures, organic components were not detectable and thus had passed into the aqueous emulsion. The mean dry weight of the cleaned sediment was 128 g.

Ionic copper(II), calcium (II) and iron (III) compounds as well as oxides of calcium, and magnesium initiated aggregation in the aqueous emulsion, which ran to complete separation and clarification of the water phase in each. The acid test was negative in all cleared water phases. All of the organic aggregate phases had a firm consistency. The dry-weight of the aggregate phases obtained after treatment with ionic compounds corresponded to the weight difference lipophilic compounds. Further, lipids and proteins adhere on shells of plant fruits and cores of seeds after extraction of the germs, which have been so far insufficiently economically utilized.

For the investigation, 6 kg of avocado seeds, in which the pulp was removed only mechanically and the pulp residues were dried, were used. They were placed in a vessel that contained 2.5 liters of a nano-emulsion consisting of an aqueous solution of 150 mmol/l arginine and 50 mmol/l caprylic acid, at a temperature of 30° C., and then, the content was continuously moved with an agitator for 30 minutes. The resultant aqueous emulsion 1 (AE 1) had a milk-like appearance with a slightly green-yellowish colour.

In a further investigation, sunflower seed husks (800 g) were added to 2 liters of a 2.0 molar arginine solution and agitated at 40° C. for 3 hours with a hook stirrer. The husks were separated from the now dark brown aqueous emulsion (AE 2) by a mesh. The husks were then placed in a screw press to separate the liquid phase bound herein, which was then added to the already separated aqueous emulsion (AE 2). Aqueous solutions of the following compounds (each 3 molar): copper chloride, copper carbonate, copper sulfate, copper acetate, were each added dropwise to 100 ml of the aqueous emulsions AE 1 and AE 2, until a clearly visible aggregation began with the formation of a free water phase. Another investigational approach was carried out with powdered calcium oxide and magnesium oxide; the metering was carried out as described in example 2. Further investigations were carried out with potassium hydroxide (3 molar) and HCl (10 vol %). The aqueous emulsion phases were mixed with a helical ribbon agitator (100 rpm); the mixing process was stopped every 30 seconds for 15 seconds. During this time, aggregation substances were not administered, and the reaction mixture was carefully inspected in order to detect the appearance of visible aggregates and a clear water phase.

In addition, the viscosity of the reaction mixture was determined using a vibration viscometer (Visco Lite d15, PCE Instruments, Germany) that was mounted on a tripod so that the measuring area of the viscometer was immersed into the upper layer of the process liquid. Measurements were performed on the resting process fluids.

In previous studies, it could be shown that relevant amounts of neutral fats (e.g., triglycerides 1-5 wt %) are present in the aqueous emulsions, obtained by decomplexation of organic complexes. The presence of neutral fats may disturb aggregation of the other organic compounds and the recognition of the aggregation process. In order to separate neutral lipids from the other organic compounds, the aqueous emulsions were heated to 90° C. for 5 minutes. Then, the aqueous solutions were admixed to the aqueous emulsions while keeping the temperature of the reaction mixture constant at 60° C. Formation of oil droplets on the liquid surface were observed at the same time as formation of aggregates and a free water phase become visible after the ionic compounds have been admixed. At this moment the addition was stopped and the reaction mixture was allowed to rest for 10 minutes when ionic compound have been administered and for 60 minutes when oxidic compounds have been admixed, at a temperature of 50° C. Thereafter phase separation was carried out by centrifugation (3,800 rpm, 10 minutes). The lipid phase was separated from the cleared aqueous phases, dried (vacuum dryer), and weight. The separated solid matter was dried and weighed thereafter. The relative weight proportions to the oil phases were calculated.

The dried oil phase was dissolved in n-hexane and an extraction was performed with a 3 wt % citric acid solution. Thereafter, phase separation was achieved by centrifugation and the organic solvent was removed by a rotary evaporator; the residual phase of neutral lipids was then weighed. The proportion of neutral lipids to the total amount of lipids that were recovered was calculated and is given in tables 3.1 and 3.2. An acid test was performed in all clarified water phases. The residual water content of the aggregate phases was determined according to Example 1. The dried aggregate phases were dissolved with organic solvents.

To this end, one aggregate phase ($CaCl_2$) which originated from the cleaning of the avocado seeds was suspended in an octanol/water mixture (95/5; v/v) and agitated at 40° C. for 10 minutes. Centrifugation (3,800 rpm, 5 min) resulted in a yellowish clear alcohol phase that was analyzed by HPLC-MS (VTM1).

In another approach the aggregate phase obtained after aggregation initiation with $CuCl_2$ was dissolved in an ethyl acetate/water mixture (80/20; v/v) and agitated at 40° C. for 10 minutes. By centrifugation at 3,800 rpm (5 min), a transparent organic phase and a clear blue water phase were obtained, while at the phase boundary there was a yellowish-whitish mass. This mass was further analyzed by the Kjeldahl procedure to determine nitrogen content (VTM2). From the transparent solvent phase, thin layer chromatography was performed for the determination of lipid fractions (VTM3).

TABLE 3.1

| AE 1 | $CuCl_2$ | $Cu(O_2CCH_3)_2$ | $CuSO_4$ | $CaCl_2$ | HCl | KOH |
|---|---|---|---|---|---|---|
| Dose volume (vol %) | 4.6 | 4.9 | 5 | 7 | 6.2 | >10 |
| Turbidity | 0 | 0 | 0 | 0 | 0 | 3 |
| Suspended matter | 0 | 0 | 0 | 1 | 0 | n.a. |
| pH | 11.1 | 10.9 | 11 | 11.3 | 2.1 | 14 |
| Water content (wt %) | 14.8 | 15.2 | 15.2 | 18.8 | 10.2 | n.a. |
| Aggregate mass (g) | 24.1 | 23.5 | 23.8 | 21.5 | 24.2 | n.a. |
| Lipid phase (g) | 3.5 | 3.1 | 3.4 | 2.1 | 0 | n.a. |
| Triglycerides in lipid phase (wt %) | 92 | 90 | 95 | 90 | n.a. | n.a. |

TABLE 3.2

| AE 2 | $CuCl_2$ | $Cu(O_2CCH_3)_2$ | $CuSO_4$ | $CaCl_2$ | HCl | KOH |
|---|---|---|---|---|---|---|
| Dose volume (vol %) | 2.3 | 3.2 | 2.5 | 5.9 | 5.2 | >10 |
| Turbidity | 0 | 0 | 0 | 0 | 0 | 3 |
| Suspended matter | 0 | 0 | 0 | 1 | 0 | n.a. |
| pH | 11.4 | 11.2 | 11.4 | 11.7 | 2.4 | 14 |
| Water content (wt %) | 13.1 | 113.8 | 13.2 | 23.1 | 7.9 | n.a. |
| Aggregate mass (g) | 8.2 | 8.4 | 8.3 | 8.6 | 8.3 | n.a. |
| Lipid phase (g) | 3.2 | 3.1 | 3.5 | 1.9 | 0 | n.a. |
| Triglycerides in lipid phase (wt %) | 96 | 95 | 95 | 93 | n.a. | n.a. |

Turbidity (visual assessment): 0 = transparent, 1 = slightly, 2 = moderately, 3 = highly turbid;
Suspended matter: 0 = no, 1 = occasional, 2 = much; n.a. = not assessable because of turbidity.

Organic aggregates obtained from purification of sunflower sleeves (aggregation with $CuSO_4$) was dissolved in a mixture of petroleum ether/isopropyl alcohol/acetic acid (85/12/3, v/v/v) and phase separation was carried out as described before. The petroleum ether was stripped and GC was performed after methylation (VTM 4). In another approach (VTM 5) (aggregation with $CaCl_2$) the dry mass was suspended in a mixture of chloroform and 5 vol % water and phase separation was obtained. The liquid phases were clear, at the phase boundary there was a solid mass which was then digested according to the procedure in the approach VTM 2.

Results: The viscosity measurements performed during the resting phases throughout the course of the aggregation initiation, exhibited a characteristic course, when the aggregation process of the organic compounds has been initialized and a complete aggregation of the organic compounds followed. The viscosity of the aqueous emulsions (AE 1: 12.1 mPa s; AE 2: 4.2 mPa s) started to rise slowly at the very beginning of the aggregation and then increased steeply up to a maximum value of 646.6 mPa s in AE1 and 85.9 mPa s in AE2 and thereafter rapidly decreased to values of 1.5 and 1.3 mPa s in the clarified WE1 and WE2, respectively. The moment in which the individual maximum value of viscosity was reached corresponded to the observation of formation of large aggregates and a clear or clarified water phase. The point in time where the criterion for termination of the addition of an aggregating agent was fulfilled corresponded to the time point where the maximum value of the viscosity was reached. The acid test was negative in all clarified water phases. These water phases had only a minimal odor.

It could be shown that highly lipophilic and apolar compounds that are constituents of the organic matter can be extracted therefrom and be separated by phase separation. Spontaneous separation of the apolar compounds with formation of a phase occurred at the moment in which the other organic compounds aggregated in processes where the reaction mixture was heated and solutions or nano-emulsions containing compounds carrying guanidino and/or amidino groups were used for decomplexing the organic matter. The separated lipid phases consisted mainly of triglycerides. The quantity of lipids that could be separated by this means was higher when ionic substances were used to initiate the inventive aggregation than was the case with the inventive use of the oxidic compounds. Accordingly, no neutral fats could be found in the aggregates, which were obtained by means of aggregation initiation with the ionic compounds according to the invention, while in the aggregates, which were obtained by oxidic compounds, still contained neutral fats. Separation of neutral fats also did not take place when the aggregation of dissolved organic compounds is accomplished by acidification of the aqueous emulsions. All solid phases had a paste-like consistency and a non-sticky and non-oily character after drying. With the exception of the solid mass obtained after acidification, the solids obtained from AE 1 had a yellow-greenish colour (with copper compounds turquoise) and an intense smell of avocado. The solid phases of AE2 were brown to blackish and had a musty smell. The residual water content of these solid phases obtained after aggregation initiation with ionic copper compounds was <15 wt %. In the solid phase, obtained by an aggregation using oxides, the water content was between 18 and 36 wt %.

Fractionation of the dried solid phase was performed with organic solvents. In the individual solvent phases could be detected: squalene (VTM1), protein compounds (VTM2, VTM5), triglycerides (VTM3), and phenolic acids such as chlorogenic acid and caffeic acid (VTM4).

Example 4

Investigation for Finding a Minimum Dose for Initiation of Aggregation and Purification of the Clarified Water Phase.

A distillate of a microbially produced biodiesel, which was obtained from organic wastes, with a content of methyl esters of >95% and of carboxylic acids of 1.2 wt %, was purified twice with an aqueous 0.5 M arginine solution. Thereafter, the two resultant aqueous emulsions, which had a milk-like appearance and a yellowish colour, were combined. In order to establish a process for the separation of the emulsified organic ingredients, the colour spectrum during a continuous dropwise addition of a copper acetate solution (concentrations: 0.5 and 2 mol/l) was continuously analyzed with slow mixing of the reaction mixture. Furthermore, spectroscopic monitoring that can be used for process control was validated for the determination of the minimum concentration of copper ions, which is required for the initiation of an aggregation that completes without further addition of aggregation substances. For this purpose, the metering and the mixing was interrupted every 30 seconds or for 15 seconds after application an amount of 0.2 vol % of the aggregation solution to allow visual analysis of the aggregation progress. During the resting periods, samples (2 ml) were withdrawn for measurement of the particle sizing distribution (methods and application see measurement methods). At the moment where formation of a free water phase and solid particles with sharp contours were recognizable, there was no further addition of the ionic solution and the samples were centrifuged after 15 minutes (4,000 rpm/10 min). If the water phase of the centrifuged sample was not transparent or the acid test (experimental procedure described in example 1) was positive, the experiment was repeated, where the total amount of the aggregation solution that was admixed was 0.2 vol % greater than the volume in the previous experiment. The volume amount which proved to allow initiation of aggregation with subsequently occurring complete separation of organic compounds as determined in 3 investigations, was defined as the minimum dosage and was used to define colour spectrum and colour intensity of the reaction mixture that is accompanied with the application of the minimal dosage of copper compounds obtained by spectroscopic measurements. Photometric measurements were performed with a rod probe immersed in the reaction liquid during these experiments. Further investigations were done using a dosage of the copper solutions that exceeded the determined minimum dose by up to 20 vol %.

In a further investigation, the minimum dosage of copper solution, according to the previous determination, was admixed to identical aqueous emulsions by three different metering modalities: a) continuous dropwise addition while the reaction mixture is continuously agitated, b) discontinuous dropwise addition between resting periods, as described above, and c) initial metering of the total volume of aqueous solution and then mixing the reaction mixture over the same duration as performed in modality a). All samples were allowed to rest for 15 minutes after finalizing the admixture of the aggregation solution and then centrifuged. All of the investigations were repeated 5 times. Spectroscopic measurements obtained during the admixture of the aggregation solution were averaged and analyzed regarding characteristic parameter values that are suitable for the detection of initiation of aggregation.

In a subsequently conducted investigation the aggregation solution was admixed with identical metering modalities as previously used, but the dosing was terminated only when the spectroscopic parameter values matched with those obtained in the previous investigation which corresponded to the application of the minimum amount of aggregation substances.

The resulting samples were centrifuged as described above and a test for completeness of separation of organic compounds, as described in example 1, was performed. Further, the clarified water phases were analyzed for the presence of carboxylic acids herein. For this purpose, samples were acidified with HCl and an extraction with hexane was performed. After methylation, gas chromatography was carried out.

The clarified process water obtained after aggregation with the determined minimum amount had a light-blue colour. An aliquot of 100 ml of the clarified aqueous phase was poured in a beaker, and 2 carbon electrodes were placed herein, which were connected to a DC voltage source. Direct current (12 V/5 mA) was applied over a period of 24 hours. The resulting aqueous phase was colourless. The carbon electrode, which served as the cathode, exhibited a slightly shiny coating which could be scraped off; this solid matter was found to contain copper. This cleaned water phase was analyzed for the concentration of arginine herein which was performed photometrically by a colour reaction with the 'coomassie' reagent. The ratio between the arginine concentrations that was present in the reaction mixture and in the cleaned aqueous phase was calculated. In 3 investigation the solid phase obtained after aggregation with copper ions was dissolved with hexane, followed by the addition of isopropyl alcohol and HCl (25 wt %), so that the ratio was 90/9/1

(v/v/v). The aggregates rapidly dissolved. After phase separation, a transparent colourless hexane phase and pale light-green alcohol-water phase was obtained. Fatty acid analysis was performed from samples of hexane phases (see test methods).

Results:

Determination of the minimum amount of solutions with solved copper ions, which is required for initiation of aggregation of organic compounds present in an arginine solution and which proceeds until all organic compounds are aggregated, with the exception of the compounds carrying guanidino and/or amidino groups, can be performed by visual inspection of the reaction mixture using a test investigation in which copper ion-containing solutions, at various concentrations, and with the use of various administration procedures are admixed to the reaction mixture. The respective amount of copper ions can be determined reproducibly by monitoring the colour spectrum or the colour intensity. Furthermore, spectroscopic parameter values are appropriate to determine when a sufficient dosage of copper ions for a complete aggregation initiation is present. In this case, matching with a defined colour scale value and colour intensity proved to be a reliable and reproducible criterion for recognizing the required dosage of the ionic compounds. Thus, a characteristic colour spectrum that can be used for prediction of complete aggregation of organic compounds could be identified. This measure criterion was also suitable for dose control when a rapid addition of the copper-containing solution is performed; the required amount of the copper ion-containing solution can be reproduced to +/−5%. The minimum amount that was determined with the performance of a continuous or a discontinuous addition of copper ion solutions varied by only 2.5%. With the use of photometric analysis to control the metering of the copper solutions, complete clarification of the reaction mixture was obtained (acid samples negative). The clarified process water had a slightly turquoise colour. Electrophoretic separation of copper ions present in the clarified water phase is possible, which is deposited as elementary copper. This process can be monitored by a complete disappearance of blue colouration. In the aqueous emulsion, there were particles that had an average size of 150 nm (peak 1) and 490 nm (peak 2) to >95%. During the addition of copper ions larger aggregates (4,000 to 6,000 nm) developed and the frequency of smaller particles decreased. Upon reaching the criterion for termination of addition of aggregation agents, particles that were smaller than 10 μm could not be detected. Virtually no carboxylic acids were detectable in the clarified process water by gas chromatography. The arginine concentration of the clarified and purified process water was only slightly lower than in the reaction mixture (minus 3+/−1.5 wt %). The averaged total loss of arginine accounted for 4.8 wt % due to a loss of process water with the aggregated organic compound mass. In the hexane phase, obtained from the extraction of the aggregate phase, a high concentration of the fatty acids, especially of oleic acid and linoleic acid was found.

Example 5

Press cake (1.5 kg) of a screw pressing of rapeseeds which has undergone hexane extraction of oil residuals, present as agglomerated solid, was dissolved in an aqueous arginine solution (10 liters/100 mmolar) and continuously stirred. After 3 hours, a mixture of an emulsion and suspended aggregates had formed. Centrifugation with a bucket centrifuge (3,800 rpm/10 minutes) was carried out. A dark brown coarse and fibrous mass and a turbid beige-yellow aqueous emulsion were obtained; the latter was decanted into a vessel. To 100 ml aliquots of the aqueous emulsion phase, aqueous solutions containing the following compounds (in each case 2 molar) were added: a) copper chloride, b) copper sulphate, c) calcium chloride, d) calcium acetate, and powdered forms of e) calcium oxide, or f) zinc oxide. The addition of the aqueous or solid forms of aggregation substances was carried out in accordance with example 1. Initiation of aggregation was accomplished by the addition of each of the aggregation compounds, respectively; the minimal amounts (determined in accordance to example 4) were 8.6 ml in a), 9.8 ml in b), 10.7 ml in c), 14.5 ml in d), 21.5 g in e), and 22.1 g in f). Furthermore, 2 samples (reference 1 and 2) were mixed with 20 ml NaCl solution (3 molar) and stirred for 20 minutes. Phase separation was conducted according to example 1. The clarified water phases were decanted. These were colourless with the exception of those obtained after aggregation with copper ions. The solid phases obtained had a pungent mustard-like odor. The reference sample 1 was subjected to ultracentrifugation (Beckman Optima XPN-90/Coulter, Germany, 960,000×g/20 minutes), reference sample 2 was stored for 3 months at 10° C. The water content of the solid phases was determined according to example 1. Samples of the dried aggregate fractions were analyzed for their ingredients. For this purpose, the solid matter of a) and b) (light-green coloured) (IIa) and c) and d) (IIb) was suspended in ethyl acetate and then water and isopropanol were added (final volume ratio 60/25/15 vol %), and the mixture was agitated for 10 minutes at 40° C. Then phase separation (3,800 rpm/5 min) was performed. The upper clear yellowish phase and the lower phase, which was greenish in IIa were decanted off; semisolid material remained in the centrifuge tube. These masses were suspended in chloroform, followed by addition of water and methanol (final volume ratio of 70/20/10 vol %). After mixing phase separation was performed as before. The liquid phases were decanted off and phase separation was performed again. Residual solid masses obtained after the first phase separation were analyzed according to the Kjeldahl procedure for determination of nitrogen. From those figures the protein content in relation to the dry weight was determined (III). Samples from transparent water/methanol phases obtained after the second separation were analyzed by thin layer chromatography for determination of phospholipids (IV).

Results:

Aqueous emulsion of a nano-emulsifying extraction from plant extracts could be cleared with ion solutions and the oxide compounds and transparent aqueous phases and compact solid masses were obtained. By means of ultracentrifugation (reference 1) only a small amount of solids could be separated. Even after a long resting time (reference 2) the emulsion was stable. After careful decanting only a slight sediment was present.

The moisture content of the aggregate phases accounted for 5 to 12 wt %. Purification and fractionation by solvents or solvent mixtures was possible. In investigation III. the obtained mass exhibited a protein content of 87 wt %. In investigation IV. a high concentration of phospholipids, particularly phosphotidylcholine and phosphatidylinositol, was found in the solvent phase.

Example 6

Cold pressed plum kernel oil was deodorized by a 3-staged refining process. The crude oil was clear and had an intense plum smell and taste. The refining was carried out by 1) an aqueous extraction by means of a 5 wt % citric acid solution (volume added 3% by volume) (agitated over 30 minutes, followed by phase separation using a centrifuge), 2) an aqueous extraction by means of a 10% sodium bicarbonate solution (volume addition 2 vol %) (homogenization with an intensive mixer for 2 minutes, then phase separation with a centrifuge), and 3) with a nanoemulsifying aqueous extraction by a 0.4 mmol/l arginine solution (adding volume 1.5 vol %) (homogenization with an intensive mixer for 5 minutes, followed by phase separation using a centrifuge (6,000×g for 10 minutes)). The oil phase was almost clear then and had almost no odor; the plum flavor was much lower than in the crude oil. The aqueous emulsion of step 3 was significantly turbid and had an intense plum smell. To each 100 ml aliquot of aqueous emulsion of the 3rd purification stage a solution containing dissolved copper tartrate (2 molar) or copper sulphate (3 molar) was added dropwise under mixing with a magnetic stirrer (100 rpm) until the formation of aggregates and a free was water phase were recognizable. Then the reaction mixture was let standing for 15 minutes and centrifuged (3,800 rpm/5 minutes). In each case, clarified water phases were obtained, which were practically odorless. After decanting the water phases, the obtained solid phases were dissolved in ethanol and stirred at 40° C. for 10 minutes. Subsequently, centrifugation was performed, as described above. Two clear liquid phases were obtained at a phase boundary. The light phase is withdrawn. The heavy phase had an oily character and a very intense plum smell.

Example 7

Investigation on Storage Stability of Aggregated Organic Compounds

A lipid phase that originated from a grease separator of a fishery was refined with a 3-stage aqueous refining process (1st stage citric acid treatment, 2nd stage treatment with a sodium hydrogen carbonate solution, 3rd stage treatment with an arginine solution (0.2 mol/l, volume ratio 4 vol %) to fish oil. The aqueous emulsion phase, which had been obtained in the third refining stage, had a milky character and an intense smell of fish. An aqueous solution of dissolved copper acetate (0.5 molar) or calcium chloride (1.5 molar) was added to the aqueous emulsion of the $3^{rd}$ stage, until aggregation formation was observed. Centrifugal phase separation was performed (3,800 rpm/5 minutes) after 30 minutes. The clarified water phase was transparent and odorless, acid tests (experimental procedure as described in example 1) of the cleared water phases were negative. An off-white compact mass was obtained after removal of the cleared water phase, which had a water content of 7.3 wt % (experimental procedure described in example 1). A sample (S1) of the solid phase was taken stored until the end of the test at minus 40° C. Another sample (S2) was placed in a vessel which was sealed and stored at about 22° C. for 6 months in a darkened room. Subsequently, the stored, and the thawed samples were examined for colour, smell, fungal or microbial colonization, protein content and characterization of fatty acids.

Furthermore, an aggregate phase obtained from an aqueous emulsion that derived from a refining of safflower oil was examined. The aqueous emulsion had been obtained by a refining step with a 0.6 mol/l arginine solution (volume addition 3 vol %) that has been centrifuged off. Aggregation was initiated with a copper(II) chloride solution (2 molar) in this emulsion. After phase separation (3,800 rpm/5 minutes) a transparent clarified water phase was obtained as well as a yellow pasty solid phase. Similarly to the previous experiment, samples of the water phase and the solid phase were taken and stored as described above. In addition to the according analyses after 6 months the content of stigmasterol, camesterol, and tocopherol was determined, and a qualitative analysis of glycolipids and phospholipids was performed by TLC.

Results:

The aggregate phase which originated from a refining of a lipid phase from fish wastes exhibited a protein content of 35 wt %; furthermore polyunsaturated fatty acids which had a proportion of 4.6 wt % as well as phospholipids with a weight fraction of 12.4 wt % were found. There was no difference in composition or the proportions by weight of the particular ingredients between the samples that have been preserved by freezing as compared to sample stored at room temperature for 6 months. In particular, there was no change in the content and proportion of polyunsaturated fatty acids. Fungal or microbial colonization was not present in any of the samples.

In the aggregate phase that originated from a refining process of vegetable oil, beta-sitosterols were detected, which corresponded to 3.2 wt % and alpha-tocopherol was present in a weight fraction of 1.8 wt %. Compared to the preserved solid sample there was no difference in the measured content of beta-sitosterol or the alpha-tocopherol during storage without preservation. Chromatography revealed sharply restricted spots, which among others corresponded to phosphatidyl choline and phospho inositol, suggesting absence of hydrolysis of those compounds.

Example 8

Large-Scale Application of the Aggregation Process.

A total of 2,000 kg of camelina-press oil, having the following contents: phosphorus 33 ppm (or 33 mg/kg), calcium 4.2 ppm (or 4.2 mg/kg), magnesium 1.7 ppm (or 1.7 mg/kg) iron 1.1 ppm (or 1.1 mg/kg), acid number 0.75 wt %, chlorophyll 6.2 ppm (or 6.2 mg/kg), was refined in the first stage with a solution of citric acid (25 wt %, volume addition 3 vol %). For this purpose the phases were brought together by two metering pumps enabling transport of defined volumes through pipelines which were combined using an in-line rotor-stator shear mixer (Fluco DMS 2.2/26-10, fluid Kotthoff, Germany) (rotor frequency 2,500 rpm, throughput volume 3 m³/h), where both phases were homogenized. The resulting water-in-oil emulsion was introduced into tank A, from which the emulsion was pumped into a plate separator (AC 1500-430 FO, Flottweg, Germany) (capacity of 3 m³/h), which was set to a drum speed of 6,600 rpm/min (centrifugal force 10,000×g). The resulting oil phase was pumped through a pipe into tank B. A second aqueous refining stage with sodium bicarbonate solution (10 wt %, volume addition 3 vol %) was performed on the oil from tank B, with the above described set up. The resulting emulsion phase after mixing was collected in tank C. Phase separation was obtained with the separator as described before and the oil phase was collected in tank D (temperature 33° C.). The refined oil had the following characteristics: phosphorus 8.2 ppm (or 8.2 mg/kg), calcium 0.21 ppm (or 0.21 mg/kg), magnesium 0.12 ppm (or 0.12 mg/kg), iron 0.09 ppm (or 0.09 mg/kg), acid number of 0.35 wt % (g/100 g), chlorophyll 3.2 ppm (or 3.2 mg/kg). In tank E 5.4 kg arginine was completely dissolved in 50 L ion-deficient water. This solution was admixed to the oil phase from tank D (volume addition 2 vol %) by means of the described dosing and mixing system. The homogenized emulsion was collected in tank F and from there it was pumped to the separator, by which phase separation was conducted at the same settings as before. The refined oil was pumped into tank G and had a temperature of 37° C. From this samples were taken for analysis. The separated aqueous emulsion was fed into tank H. At the end of the refining process, 49 liters of a yellowish-green, strongly turbid emulsion were obtained herein. The emulsion had an intense and pungent plant-smell. From tank H 200 ml of the aqueous emulsion were taken and an examination on the required minimum amount of copper(II) ions for aggregation initiation was taken out as well as a simultaneously conducted spectroscopic study of the emulsion as performed in Example 4. The parameter values for the minimal amount, the temperature and pH were recorded. The minimum volume amount of solution to be added was 0.36 vol % for a 2 molar cupric chloride solution. A fork stirrer was inserted into tank H, which rotated at a speed of 300 rpm. A continues flow of a small volume of the aqueous emulsion through an external pipe system was installed, by means of a roller pump, that enabled the solution to flow through a spectroscopy measurement cell (AF26, Optitek, Germany) at a flow rate of 50 ml/min. The aqueous emulsion was then returned to the reactor mixture. The measuring cell was connected to a converter (Control 8000, Optitek, Germany). The adsorption from a colour spectrum in the visible light and from near infrared range were determined continuously hereby. Furthermore the temperature and pH of the reaction solution were continuously monitored by appropriate probes immersed into the reaction mixture. It was ensured that the same temperature and pH conditions existed as in the investigation for determination of the minimum amount of the ion solution. By means of a roller pump, a 2 molar copper(II) chloride solution was added to tank H, initially at a rate of 50 ml/minute for 5 minutes. Thereafter, the speed of the agitator was set at 80 rpm/minute and the inlet flow was reduced to 10 ml/minute. The addition was stopped at that moment where the previously determined spectroscopic parameter values (with turbidity compensation) of the colour spectrum were matched, which has been accompanied with an initiation of aggregation. This was the case after admixture of a total volume of 210 ml. The mixing process was stopped then. The values of pH and temperature of the reaction solution were similar to those that were present at the previous screening investigation. After a standing period of 15 minutes, the content of tank H was conducted via a bottom outlet through a pipeline into a lab-scale decanter (MD80, Lemitec, Germany), hereby centrifugal separation of the solid phase (centrifugal force 4,000×g, throughput volume 80 liters/h) was carried out. The solid phase was led into container 1. The separated water phase was fed into tank I. From this, samples were taken for analysis of the turbidity and for the presence of organic compounds by using an acid test. The water phase of tank I was pumped at a flow rate of 0.5 liters/h through a 60 cm long column, which was filled with 800 g Dowex 50 WX4 ion exchange resin, and fed into the feed tank E1. Furthermore, the concentration of arginine was determined according to example 4.

A further refining was conducted using the same crude oil and procedure as described above. Deviating from this, the aqueous solution to perform the 3$^{rd}$ refining stage was taken from tank E1, which was the purified water phase from the previous refinement process. After mixing with the oils obtained from the second refining step (tank D1), the emulsion was placed in tank F1). Thereafter phase separation was performed and then the oil phase was forwarded to tank G1.

The water phase was fed into tank H1. The volume obtained herein was 45 liters. Samples were taken from storage tanks G1 and H1 for the analyses as described before. A cupric chloride solution was added to the aqueous emulsion in tank H1 under the same conditions as performed in the previous refining process. Process control was carried out by means of a continuous spectroscopic analysis of the reaction mixture as previously performed. The volume of cupric chloride solution required to match with the spectroscopic criteria to terminate addition was 201 ml. Phase separation was performed after a standing period of 15 minutes. The clarified water phase was fed into tank I1 and the solid phase into container 2. The weights of the solid phases in containers 1 and 2 were determined. Samples were taken for determination of moisture content, determined in accordance with example 1. From both solid phases 100 g were investigated for the dissolvability in organic solvents. Here, among others, they could be dissolved in chloroform (300 ml). Then, 30 ml of methanol and 10 ml water were added. After 60 minutes of stirring in a water bath (40° C.) phase separation was performed. Using a rotary evaporator, 100 ml chloroform phase was concentrated to dryness. This was followed by suspension of the dry mass in n-hexane, and after dissolution a 10% ethanol solution was added, which was acidified to pH 2 by addition of HCl Thereafter, phase separation and removal of the clear hexane phase was performed. The hexane phase was further processed for determination of free fatty acids that were contained herein; analyses were performed by gas chromatography. TLC was performed (experimental procedure as in Example 1) for detection of phospholipids from a sample of the methanol phase.

Results: The aqueous emulsion obtained after refining with an arginine solution could be clarified by a copper II ion containing solution through initiation of aggregation of organic compounds. It could be demonstrated that process control in a large scale production is possible, by spectroscopic parameters that have been obtained in a lab-scale investigation for determination of the minimum amount of aggregation substances required to initialize aggregation.

The aggregation proceeded completely, whereby phase separation was possible by means of a decanter. The water phase was transparent as determined by visual appearance and by turbidimetry (5 FTU), without suspended solids and had a light blue colour. Acidification gave no solid precipitation. After passing the clarified water phase through an ion exchange resin it was partially blue and the cleared aqueous phase had a slight light-yellowish colour. The so purified aqueous phase, which contained almost no copper ions, was successfully reused for the second time for the third aqueous refining stage which was carried out under the same conditions as before. The aqueous emulsion obtained thereby did not differ from the one previously obtained. Initiation of aggregation of the organic compounds could be performed by process control using the identical parameters as in the previously conducted aggregation process.

The solid mass obtained by separation with a decanter was comparable among both separations of organic compounds from the oil phase with the identical solution containing arginine, which amounted of 6.8 kg and 6.5 kg. The residual water content in the solid phases was 5.6 and 5.9 wt %. Clarification of the water phase was again complete after reuse and there were no organic compounds or copper ions present. The arginine concentration in the recycled arginine solution was 11.2 wt % lower compared to the concentration in the solution that had previously been used.

Oil parameter values present in the oil phases obtained after the initial refining with the arginine solution did not differ from that obtained after refinement with the reused arginine solution: phosphorus: 0.8/0.9, calcium <0.02/<0.02 mg/kg, magnesium: <0.02/<0.02 mg/kg, iron: <0.02/<0.02 mg/kg, acid number: 0.03/0.04 g/100 g, chlorophyll 0.02/0.01 mg/kg.

By dissolution of the aggregate phases with solvents, the presence of phospholipids phosphatidylcholine, and phosphatidylinositol were detected by TLC. Furthermore, high concentrations of volatile fatty acids, e.g., linoleic and linolenic acid, were identified by GC. In other solvent fractions squalenes, tocopherol, chlorophyll, and benzo[a]pyrene could be detected.

The invention claimed is:

1. A method for the aggregation and separation of a mixture of organic substances, being dissolved in an aqueous emulsion, characterized by the steps of:
   a) provision of an aqueous emulsion having organic compounds dissolved therein, wherein the organic compounds are carboxylic acids, phospholipids, glycolipids, glyceroglycolipids, phenols, sterols, chlorophylls and/or sinapines, wherein the aqueous emulsion contains at least one compound carrying guanidino or amidino groups with a $K_{ow}$<6.3,
   b) mixing the emulsion of step a) with an aqueous solution containing copper(II) ions and/or calcium ions until aggregate formation, wherein the achievement of aggregate formation signifies the beginning of the aggregation, which can be recognized with the eye,
   c) separating the aggregates from step b) by sedimentation, filtration, or centrifugation after obtaining an aggregated phase of organic compounds from step b), wherein a reusable clarified water phase containing compounds carrying guanidino- or amidino groups is obtained,
   d) reuse of the clarified water phase containing compounds carrying guanidino or amidino groups for the provision of an aqueous emulsion according to step a).

2. A method for the aggregation and separation of a mixture of organic substances, being dissolved in an aqueous emulsion, characterized by the steps of:
   a) provision of an aqueous emulsion having organic compounds dissolved therein, wherein the organic compounds are proteins, flavours, waxes, fatty alcohols, fragrances, flavouring agents, carboxylic acids, phospholipids, glycolipids, glyceroglycolipids, phenols, sterols, chlorophylls and/or sinapines, wherein the aqueous emulsion contains at least one compound carrying guanidino or amidino groups with a $K_{ow}$<6.3,
   b) mixing the emulsion of step a) with an aqueous solution containing copper(II) ions and/or calcium ions until aggregate formation, wherein the achievement of aggregate formation signifies the beginning of the aggregation, which can be recognized with the eye,
   c) separating the aggregates from step b) by sedimentation, filtration, or centrifugation after obtaining an aggregated phase of organic compounds from step b), wherein a reusable clarified water phase containing compounds carrying guanidino- or amidino groups is obtained,
   d) reuse of the clarified water phase containing compounds carrying guanidino or amidino groups for the provision of an aqueous emulsion according to step a).

3. The method according to claim 1, wherein the aqueous emulsion according to step a) originates from a refining process of a lipid phase.

4. The method according to claim 1, wherein the aqueous emulsion according to step a) originates from a cleaning or nano-emulsifying decomplexation process of organic compounds.

5. The method according to claim 1, wherein the aqueous emulsion is an aqueous nano-emulsion.

6. The method according to claim 1, wherein step b) is carried out at a maximum temperature of 75° C.

7. The method according to claim 1, wherein said copper (II) ions are separated from the aqueous solution after step c).

8. The method according to claim 1, wherein together with or instead of the aqueous solution containing the copper(II) ions and/or calcium ions in step b) calcium oxide, magnesium oxide and/or zinc oxide in solid form or dispersed form are added and admixed to the aqueous emulsion that result in aggregate formation is attained.

9. The method according to claim 1 for obtaining carboxylic acids, phospholipids, glycolipids, glyceroglycolipids, phenols, sterols, chlorophylls, and/or sinapines.

10. The method according to claim 1 to obtain proteins, flavours, waxes, fatty alcohols, fragrances, flavouring agents, carboxylic acids, phospholipids, glycolipids, glyceroglycolipids, phenols, sterols, chlorophylls, and/or sinapines.

11. The method according to claim 1, wherein a clarified and/or purified water phase obtained after step c) is used for aqueous refining.

12. The method according to claim 1 for extraction of neutral fats characterized by the steps of:
    a) provision of an aqueous emulsion having organic compounds dissolved therein, wherein the organic compounds are carboxylic acids, phospholipids, glycolipids, glyceroglycolipids, phenols, sterols, chlorophylls and/or sinapines, wherein the aqueous emulsion contains at least one compound carrying guanidino or amidino groups with a $K_{ow}$<6.3,
    b) mixing the emulsion of step a) with an aqueous solution containing copper(II) ions and/or calcium ions until aggregate formation, wherein the achievement of aggregate formation signifies the beginning of the aggregation, which can be recognized with the eye,
    c) separating the aggregates from step b) by sedimentation, filtration, or centrifugation after obtaining an aggregated phase of organic compounds from step b), wherein a reusable clarified water phase containing compounds carrying guanidino- or amidino groups is obtained,
    d) reuse of the clarified water phase containing compounds carrying guanidino or amidino groups for the provision of an aqueous emulsion according to step a).

13. The method according to claim 2, wherein the aqueous emulsion according to step a) originates from a refining process of a lipid phase.

14. The method according to claim 2, wherein the aqueous emulsion according to step a) originates from a cleaning or nano-emulsifying decomplexation process of organic compounds.

15. The method according to claim 2, wherein the aqueous emulsion is an aqueous nano-emulsion.

16. The method according to claim 2, wherein step b) is carried out at a maximum temperature of 75° C.

17. The method according to claim 2, wherein said copper(II) ions are separated from the aqueous solution after step c).

18. The method according to claim 2, wherein together with or instead of the aqueous solution containing the copper(II) ions and/or calcium ions in step b) calcium oxide, magnesium oxide and/or zinc oxide in solid form or dispersed form are added and admixed to the aqueous emulsion that result in aggregate formation is attained.

19. The method according to claim 2 for obtaining carboxylic acids, phospholipids, glycolipids, glyceroglycolipids, phenols, sterols, chlorophylls, and/or sinapines.

20. The method according to claim 2 to obtain proteins, proteins, flavours, waxes, fatty alcohols, fragrances, flavouring agents, carboxylic acids, phospholipids, glycolipids, glyceroglycolipids, phenols, sterols, chlorophylls, and/or sinapines.

21. The method according to claim 2, wherein a clarified and/or purified water phase obtained after step c) is used for aqueous refining.

22. The method according to claim 2 for extraction of neutral fats characterized by the steps of:
   a) provision of an aqueous emulsion having organic compounds dissolved therein, wherein the organic compounds are proteins, flavours, waxes, fatty alcohols, fragrances, flavouring agents, carboxylic acids, phospholipids, glycolipids, glyceroglycolipids, phenols, sterols, chlorophylls and/or sinapines, wherein the aqueous emulsion contains at least one compound carrying guanidino or amidino groups with a $K_{ow}$<6.3,
   b) mixing the emulsion of step a) with an aqueous solution containing copper(II) ions and/or calcium ions until aggregate formation, wherein the achievement of aggregate formation signifies the beginning of the aggregation, which can be recognized with the eye,
   c) separating the aggregates from step b) by sedimentation, filtration, or centrifugation after obtaining an aggregated phase of organic compounds from step b), wherein a reusable clarified water phase containing compounds carrying guanidino- or amidino groups is obtained,
   d) reuse of the clarified water phase containing compounds carrying guanidino or amidino groups for the provision of an aqueous emulsion according to step a).

* * * * *